US009182402B2

(12) United States Patent
Vasioukhin et al.

(10) Patent No.: US 9,182,402 B2
(45) Date of Patent: Nov. 10, 2015

(54) HEPSIN INHIBITORS

(71) Applicant: Fred Hutchinson Cancer Research Center, Seattle, WA (US)

(72) Inventors: Valeri I. Vasioukhin, Seattle, WA (US); John R. Chevillet, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 115 days.

(21) Appl. No.: 14/157,347

(22) Filed: Jan. 16, 2014

(65) Prior Publication Data
US 2014/0127127 A1 May 8, 2014

Related U.S. Application Data

(63) Continuation of application No. 13/874,301, filed on Apr. 30, 2013, now Pat. No. 8,664,266, which is a continuation of application No. 12/997,465, filed as application No. PCT/US2009/044905 on May 21, 2009, now Pat. No. 8,450,334.

(60) Provisional application No. 61/060,756, filed on Jun. 11, 2008.

(51) Int. Cl.
| | |
|---|---|
| *C12N 9/99* | (2006.01) |
| *A61K 31/34* | (2006.01) |
| *G01N 33/574* | (2006.01) |
| *A61K 31/40* | (2006.01) |
| *A61K 31/433* | (2006.01) |
| *A61K 31/473* | (2006.01) |
| *A61K 31/506* | (2006.01) |
| *A61K 31/536* | (2006.01) |
| *A61K 31/343* | (2006.01) |
| *A61K 49/00* | (2006.01) |
| *A61K 51/00* | (2006.01) |

(52) U.S. Cl.
CPC ............ *G01N 33/574* (2013.01); *A61K 31/343* (2013.01); *A61K 31/40* (2013.01); *A61K 31/433* (2013.01); *A61K 31/473* (2013.01); *A61K 31/506* (2013.01); *A61K 31/536* (2013.01); *A61K 49/0004* (2013.01); *A61K 49/0017* (2013.01); *A61K 51/00* (2013.01); *C12N 9/99* (2013.01)

(58) Field of Classification Search
CPC .................................. A61K 31/34; C12N 9/99
USPC ..................................... 435/184; 514/468, 470
See application file for complete search history.

(56) References Cited

U.S. PATENT DOCUMENTS

| | | | |
|---|---|---|---|
| 8,435,511 | B2 | 5/2013 | Ganesan et al. |
| 8,450,334 | B2 | 5/2013 | Vasioukhin et al. |
| 2011/0021337 | A1 | 1/2011 | Sawai et al. |
| 2013/0035250 | A1 | 2/2013 | Wirth et al. |

OTHER PUBLICATIONS

Abbenante et al., "Protease Inhibitors in the Clinic," *Medicinal Chemistry 1*:71-104, 2005.
Bauvois, "Murine thymocytes possess specific cell surface-associated exoaminopeptidase activities: preferential expression by immature CD4⁻CD8⁻ subpopulation," *Eur. J. Immunol. 20*:459-468, 1990.
Bauvois et al., "Human U937 cell surface peptidase activities: characterization and degradative effect on tumor necrosis factor-α," *Eur. J. Immunol. 22*:923-930, 1992.
Betsunoh et al., "Clinical relevance of hepsin and hepatocyte growth factor activator inhibitor type 2 expression in renal cell carcinoma," *Cancer Sci. 98*(4):491-498, 2007.
Bradford et al., "Molecular markers of prostate cancer," *Urologic Oncology: Seminars and Original Investigations 24*:538-551, 2006.
Chirgadze et al., "The crystal structure of human α-thrombin complexed with LY178550, a nonpeptidyl active site-directed inhibitor," *Protein Science 6*:1412-1417, 1997.
Dhanasekaran et al., "Delineation of prognostic biomarkers in prostate cancer," *Nature 412*:822-826, 2001.
Evans et al., "Suppression of the Invasive Capacity of Human Breast Cancer Cells by Inhibition of Urokinase Plasminogen Activator via Amiloride and B428," *The American Surgeon 66*(5):460-464, 2000.
Fear et al., "Protease inhibitors and their peptidomimetic derivatives as potential drugs," *Pharmacology & Therapeutics 113*:354-368, 2007.
Feldman et al., "The Development of Androgen-Independent Prostate Cancer," *Nature Reviews Cancer 1*:34-45, 2001.
Kirchhofer et al., "Hepsin activates pro-hepatocyte growth factor and is inhibited by hepatocyte growth factor activator inhibitor-1B (HAI-1B) and HAI-2," *FEBS Letters 579*:1945-1950, 2005.
Klezovitch et al., "Hepsin promotes prostate cancer progression and metastasis," *Cancer Cell 6*:185-195, 2004.
Magee et al., "Expression Profiling Reveals Hepsin Overexpression in Prostate Cancer," *Cancer Research 61*:5692-5696, 2001.
Matsuo et al., "Expression of the Serine Protease Hepsin and Clinical Outcome of Human Endometrial Cancer," *Anticancer Research 28*:159-164, 2008.
McGowen et al., "The Surface of Prostate Carcinoma DU145 Cells Mediates the Inhibition of Urokinase-type Plasminogen Activator by Maspin," *Cancer Research 60*:4771-4778, 2000.
Moran et al., "Pro-urokinase-type Plasminogen Activator Is a Substrate for Hepsin," *The Journal of Biological Chemistry 281*(41):30439-30446, 2006.
Raynaud et al., "Characterization of Specific Proteases Associated With the Surface of Human Skin Fibroblasts, and Their Modulation in Pathology," *Journal of Cellular Physiology 151*:378-385, 1992.

(Continued)

*Primary Examiner* — Raymond Henley, III
(74) *Attorney, Agent, or Firm* — Seed IP Law Group PLLC

(57) ABSTRACT

Compositions and methods are provided for preventing or attenuating cancer progression or blocking metastasis in prostate cancer and other cancers (e.g., ovarian carcinoma, endometrial cancer, renal cell carcinoma) that are characterized by overexpression of the type II cell surface serine protease hepsin, based on the discovery of multiple disclosed compounds having activity as specific hepsin inhibitors.

22 Claims, 7 Drawing Sheets

(56) References Cited

OTHER PUBLICATIONS

Sameni et al., "Imaging Proteolysis by Living Human Breast Cancer Cells," *Neoplasia* 2(6):496-504, 2000.

Satonin et al., "Comparison of gas chromatography and high-performance liquid chromatography for the analysis of probucol in plasma," *Journal of Chromatography* 380:401-406, 1986.

Schmidt et al., "Anti-Psoriatic Drug Anthralin Activates Transcription Factor NF-$_K$B in Murine Keratinocytes," *The Journal of Immunology* 156:4514-4519, 1996.

Sheetz et al., "MDL 29311, an Analog of Probucol, Decreases Triglycerides in Rats by Increasing Hepatic Clearance of Very-Low-Density Lipoprotein," *Metabolism* 43(2):233-240, 1994.

Somoza et al., "The Structure of the Extracellular Region of Human Hepsin Reveals a Serine Protease Domain and a Novel Scavenger Receptor Cysteine-Rich (SRCR) Domain," *Structure* 11:1123-1131, 2003.

Srikantan et al., "*HEPSIN* Inhibits Cell Growth/Invasion in Prostate Cancer Cells," *Cancer Research* 62:6812-6816, 2002.

Stamey et al., "Molecular Genetic Profiling of Gleason Grade 4/5 Prostate Cancers Compared to Benign Prostatic Hyperplasia," *The Journal of Urology* 166:2171-2177, 2001.

Tanimoto et al., "Hepsin, a Cell Surface Serine Protease Identified in Hepatoma Cells, Is Overexpressed in Ovarian Cancer," *Cancer Research* 57:2884-2887, 1997.

Tardif et al., "Effects of AGI-1067 and Probucol After Percutaneous Coronary Interventions," *Circulation* 107:552-558, 2003.

Vasioukhin, "Hepsin Paradox Reveals Unexpected Complexity of Metastatic Process," *Cell Cycle* 3(11):1394-1397, 2004.

Wu et al., "Probucol Inactivates ABCA1 in the Plasma Membrane with Respect to Its Mediation of Apolopoprotein Binding and High Density Lipoprotein Assembly and to Its Proteolytic Degradation," *The Journal of Biological Chemistry* 279(29):30168-30174, 2004.

Zacharski et al., "Expression of the Factor VII Activating Protease, Hepsin, in situ in Renal Cell Carcinoma," *Thromb. Haemost.* 79:876-877, 1998.

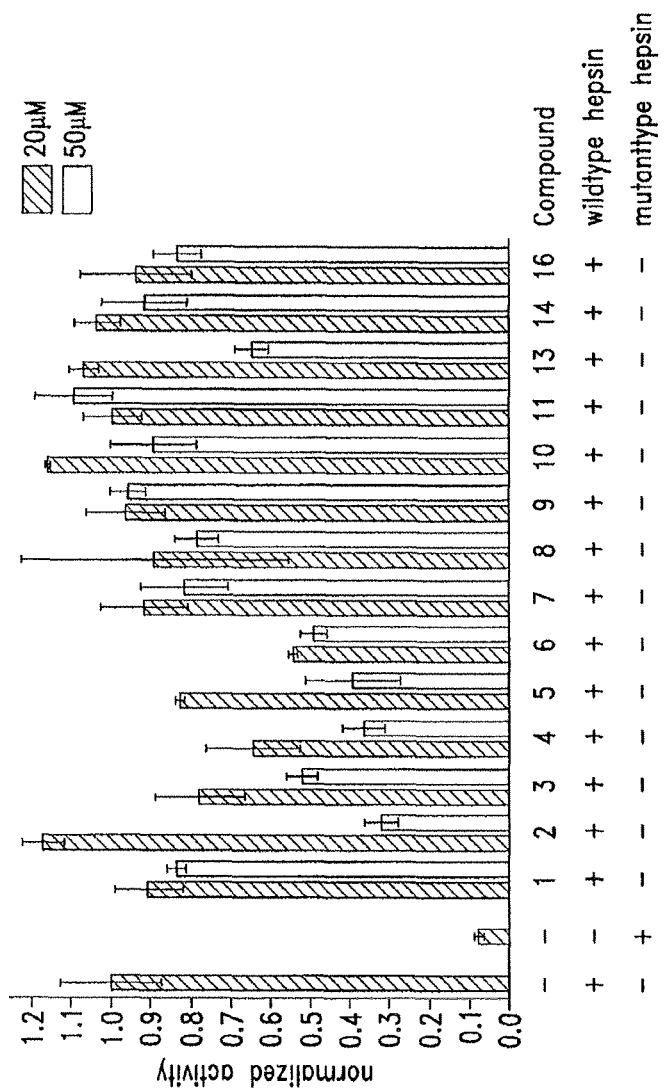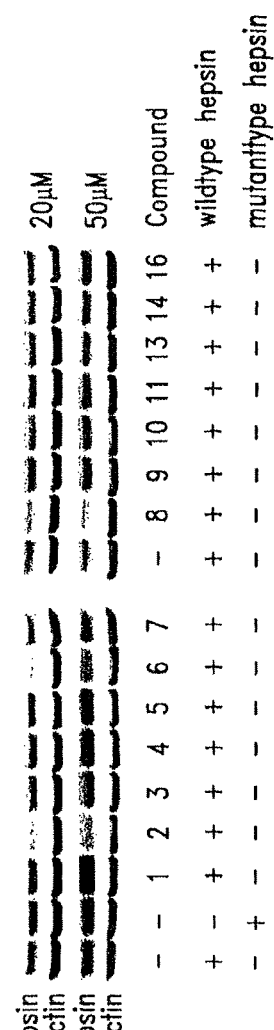
FIG. 6A
FIG. 6B

HEPSIN INHIBITORS

STATEMENT OF GOVERNMENT INTEREST

This invention was made in part with government support under Grant No. R01 CA102365 awarded by the National Cancer Institute/National Institutes of Health. The government has certain rights in this invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_401C2_SEQUENCE_LISTING.txt. The text file is 36 KB, was created on Jan. 12, 2014, and is being submitted electronically via EFS-Web.

BACKGROUND

1. Technical Field

The presently disclosed invention embodiments relate to compositions and methods for the treatment of cancer. In particular, the present embodiments relate to preventing or attenuating cancer progression or blocking metastasis in a subject known to have, or suspected of being at risk for having, prostate cancer, ovarian carcinoma, endometrial cancer, or renal cell carcinoma, by administering a hepsin inhibitor as described herein.

2. Description of the Related Art

Prostate cancer is the most common cancer in United States males, with an estimated 186,320 new cases in 2008, accounting for 25% of cancer incidence and 10% of cancer deaths (Cancer Facts and Figures, 2008, American Cancer Society, Atlant, Ga.). Prostate cancer develops slowly in the majority of cases; however progression to metastasis is highly lethal and can occur rapidly. Significant progress has been made in recent years in the understanding of molecular mechanisms responsible for prostate cancer initiation and progression, but therapeutic approaches for the treatment of prostate cancer remain limited. Treatments to prevent metastasis include radical prostatectomy and radiation therapy, both of which carry significant risk to urinary and sexual function. Metastatic prostate cancer can be treated with androgen ablation therapy, but almost uniformly results in hormone-refractory disease leading to mortality. Although localized prostate tumors are usually curable, diagnosis of prostate cancer remains a difficult, inexact process and treatment can result in side effects that significantly impact quality of life (The Prostate-Specific Antigen (PSA) Test: Questions and Answers, 2007, U.S. National Institutes of Health, Bethesda, Md.; Early Prostate Cancer: Questions and Answers, 2007, U.S. National Institutes of Health, Bethesda, Md.). Metastatic prostate cancer is highly resistant to therapeutic intervention and is almost uniformly lethal. Therefore, the development of effective novel targeted therapies to inhibit prostate cancer progression and metastasis will have a significant impact on prostate cancer mortality.

Multiple genetic and epigenetic changes take place during human prostate cancer initiation and progression (Vasioukhin, 2004 *Cell Cycle* 3, 1394-1397; Bradford et al., 2006 *Urol. Oncol.* 24, 538-551). Hepsin (HPN) is one of the most upregulated genes in human prostate cancer and encodes a type-II transmembrane serine protease that is overexpressed in up to 90% of prostate tumors with levels often increased >10 fold (Magee et al., 2001 *Cancer Res* 61, 5692-5696; Dhanasekaran et al., 2001 *Nature* 412, 822-826; Stamey et al., 2001 *J. Urol.* 166, 2171-2177). Hepsin is upregulated early in prostate cancer initiation and is maintained at high levels throughout progression and metastasis. In addition, hepsin is also overexpressed in ovarian and renal carcinomas (Tanimoto et al., 1997 *Cancer Res* 57, 2884-2887; Zacharski et al., 1998 *Thromb Haemost* 79, 876-877; Betsunoh et al., 2007 *Cancer Sci.* 98(4):491-8) and in endometrial cancer (Matsuo et al., 2008 *Anticancer Res.* 28(1A):159-64).

Significant evidence indicates that hepsin overexpression plays an important role in the promotion of prostate cancer progression and metastasis. Hepsin upregulation in a transgenic mouse model of localized prostate cancer promoted progression, causing the transition of nonmetastatic cancer into an aggressive carcinoma with metastasis to bone, liver and lung (Klezovitch et al., 2004 *Cancer Cell* 6, 185-195). The cellular context and level of hepsin expression appear to be important to the phenotype, as high levels of hepsin overexpression in a prostate cancer cell line reduced cell proliferation and invasion (Srikantan et al., 2002 *Cancer Res* 62, 6812-6816). While the molecular mechanisms responsible for hepsin function in prostate cancer in vivo are unknown, in vitro evidence indicates that hepsin can activate pro-urokinase plasminogen activator (pro-uPA) and pro-hepatocyte growth factor (pro-HGF) (Moran et al., 2006 *J Biol Chem* 281:30439-30446; Kirchhofer et al., 2005 *FEBS Lett* 579: 1945-1950). Activation of the uPA cell-surface serine protease system and HGF-Met scattering pathway may be responsible for promotion of metastasis by hepsin, and is consistent with the observed basement membrane disruption in mouse prostates overexpressing hepsin (Klezovitch et al., 2004 *Cancer Cell* 6:185-195).

Protease-targeted drugs have proven to be clinically useful for treatment of HIV and hypertension and have shown potential in the treatment of cancer, obesity, cardiovascular, inflammatory and neurodegenerative diseases (Fear et al., 2007 *Pharmacol Ther* 113:354-368). For example, WX-UK1 is a potent small-molecule inhibitor of uPA developed by Wilex and has shown potent antitumor and antimetastasis activity in a rat breast cancer model (Abbenante et al., 2005 *Med Chem* 1:71-104). WX-UK1 has completed phase Ib trials in patients with solid tumors and is currently in combination phase I trials with capecitabine in patients with breast cancer and other solid tumors.

Despite such advances as the recognition of hepsin upregulation in prostate cancer, ovarian carcinoma, endometrial cancer, and renal cell carcinoma, neither this example of cancer-related aberrant gene expression nor other potential targets for anti-cancer therapeutic intervention have yielded safe and effective therapies to block cancer progression or prevent metastasis. For example, invasive or micrometastatic prostate cancers are largely unresponsive to standard cytotoxic drugs used in other areas of oncology (e.g., DNA-binding or DNA-disrupting agents), and use of these cytotoxic agents is generally accompanied by a host of undesirable side-effects associated with their effects on normal, healthy tissues. The unusual androgen dependence of prostate tumors has made androgen ablation therapy a temporarily effective clinical strategy for management of prostate cancer, but androgen-independent tumor recurrence within a median of two to three years is common and is typically untreatable (Feldman et al., 2001 *Nat. Rev. Cancer* 1:34-45).

Clearly there remains a significant unmet need for more and better anti-cancer agents, including agents that are capable of preventing cancer progression and/or blocking metastasis, and preferably further including agents having little or no cytotoxicity toward non-malignant cells, and that can be conveniently administered. Effective agents to prevent disease progression would reduce the need for surgical or radiation-based therapies, and could have a significant impact on prostate cancer related mortality. The present invention addresses these needs and offers other related advantages.

BRIEF SUMMARY

In one aspect there is provided by the present invention a method for preventing or attenuating cancer progression or blocking metastasis in a subject known to have, or suspected of being at risk for having, prostate cancer, ovarian carcinoma, endometrial cancer or renal cell carcinoma, comprising administering to the subject a therapeutically effective amount of a hepsin inhibitor that comprises at least one compound of formulae (I)-(XIV):

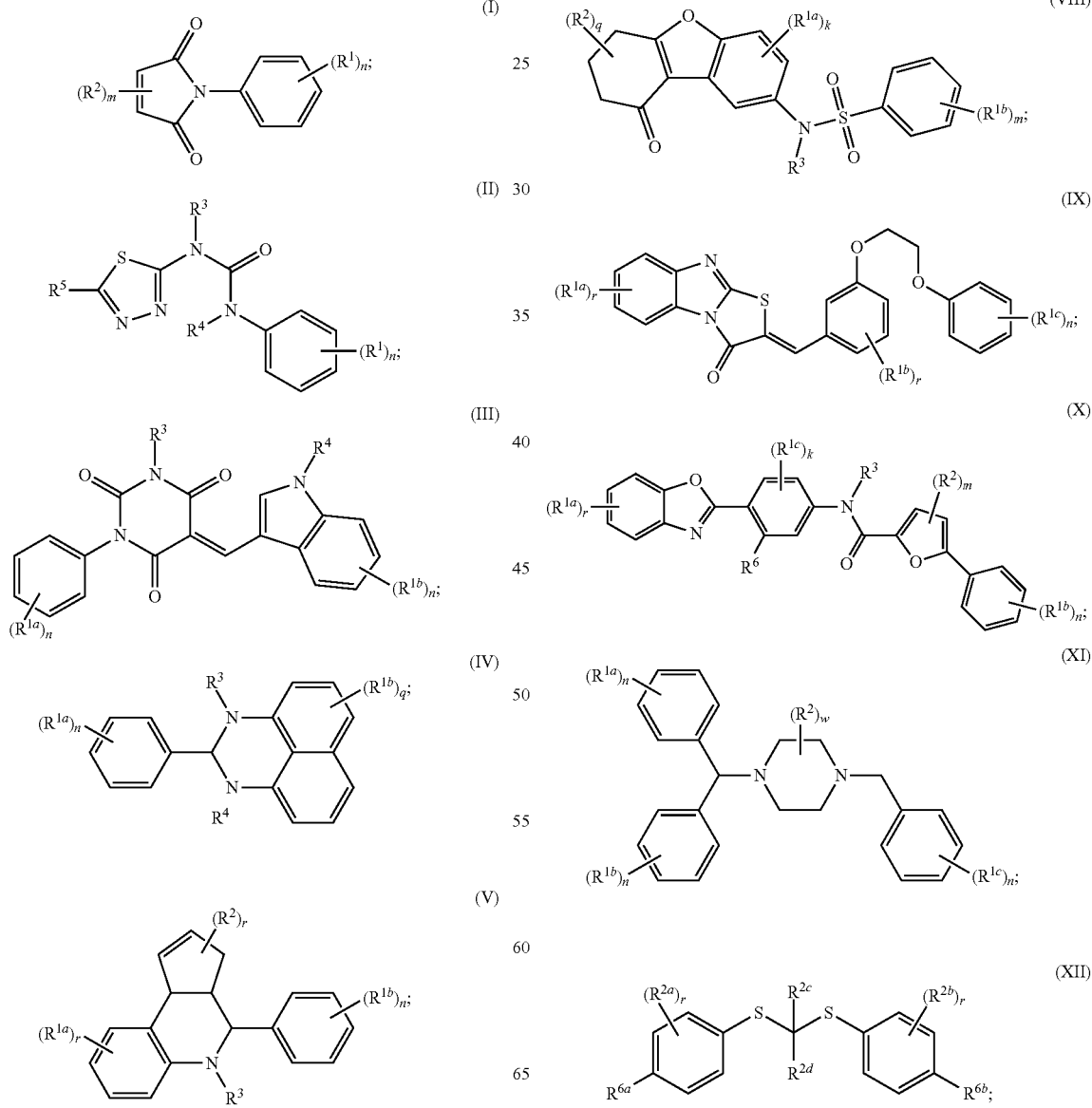

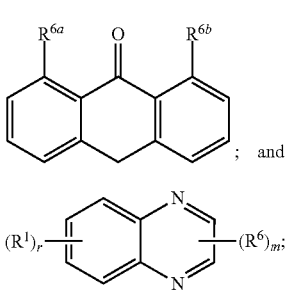

wherein:
each k is 1, 2 or 3;
each m is 1 or 2;
each n is 1, 2, 3, 4 or 5;
each r is 1, 2, 3 or 4;
q is 1, 2, 3, 4, 5 or 6;
w is 1, 2, 3, 4, 5, 6, 7 or 8;
each $R^1$, $R^{1a}$, $R^{1b}$, $R^{1c}$ and $R^{1d}$ is independently selected from the group consisting of hydrogen, alkyl, halo, haloalkyl, optionally substituted aryl, optionally substituted aralkyl, —$OR^7$, —CN, —$C(O)R^7$, —$C(O)OR^7$, —$C(O)N(R^7)R^8$, —$NO_2$, —$N(R^7)R^8$, —$N(R)C(O)R^8$, and —$N(R^7)C(O)OR^8$;
each $R^2$, $R^{2a}$, $R^{2b}$, $R^{2c}$ and $R^{2d}$ is independently selected from the group consisting of hydrogen, alkyl, halo, haloalkyl, optionally substituted aryl and optionally substituted aralkyl;
each $R^3$ and $R^4$ is independently selected from the group consisting of hydrogen, alkyl, optionally substituted aryl and optionally substituted aralkyl;
$R^5$ is selected from the group consisting of hydrogen, optionally substituted aryl, optionally substituted aralkyl and —$R^9$—$OR^7$;
each $R^6$, $R^{6a}$ and $R^{6b}$ is independently selected from the group consisting of hydrogen and —$OR^7$;
each $R^7$ and $R^8$ is independently selected from the group consisting of hydrogen, alkyl, optionally substituted aryl and optionally substituted aralkyl; and
$R^9$ is a straight or branched alkylene chain;
as a single stereoisomer or a mixture thereof;
or a pharmaceutically acceptable salt thereof.

According to certain embodiments, cancer progression or metastasis is substantially impaired. In certain embodiments the subject has or is suspected of being at risk for having prostate cancer. In certain further embodiments the subject has prostatic intraepithelial neoplasia, prostate-confined non-invasive low grade cancer, prostate-confined invasive cancer, or metastatic prostate cancer. In certain other embodiments the subject has or is suspected of being at risk for having ovarian cancer. In certain further embodiments the subject has stage I, stage II, stage III, stage IV or recurrent ovarian cancer. In certain other embodiments the subject has or is suspected of being at risk for having renal cell carcinoma. In certain further embodiments the subject has stage I, stage II, stage III, or stage IV renal cell carcinoma. In certain other embodiments the subject has or is suspected of being at risk for having endometrial cancer. In certain further embodiments the subject has stage I, stage II, stage III, or stage IV endometrial cancer.

In certain embodiments the hepsin inhibitor is administered orally, parenterally, intraperitoneally, intravenously, intraarterially, transdermally, sublingually, subcutaneously, intramuscularly, rectally, transbuccally, intranasally, liposomally, via inhalation, intraoccularly, via local delivery, subcutaneously, intraadiposally, intraarticularly or intrathecally.

In another embodiment there is provided a method of inhibiting hepsin proteolytic activity on a cell surface, comprising contacting (i) a cell that comprises a cell surface hepsin polypeptide and (ii) a hepsin inhibitor, under conditions and for a time sufficient for the hepsin inhibitor to interact specifically with the cell surface hepsin polypeptide, and thereby inhibiting hepsin proteolytic activity on the cell surface, wherein the cell surface hepsin polypeptide is selected from the group consisting of (i) a cell surface polypeptide comprising the amino acid sequence set forth in any one of SEQ ID NOS:1-3, 6 and 9 (NP_892028; NP_002142; BC025716; AAI38810; AAB4221), (ii) a cell surface polypeptide comprising an amino acid sequence that is at least 85%, 90% or 95% identical to the polypeptide of (i) and that is capable of specific enzymatic cleavage of a chromogenic serine protease substrate that comprises L-pyroglutamyl-L-prolyl-L-arginine-p-nitroaniline hydrochloride (Glu-Pro-Arg-pNA), and (iii) a cell surface polypeptide that comprises a hepsin catalytic domain or a functional fragment thereof, the hepsin catalytic domain or functional fragment thereof comprising an amino acid sequence that is at least 80%, 85%, 90% or 95% identical to the amino acid sequence set forth in any one of SEQ ID NOS:5, 8 and 11 and that is capable of specific enzymatic cleavage of a chromogenic serine protease substrate that comprises L-pyroglutamyl-L-prolyl-L-arginine-p-nitroaniline hydrochloride (pyroGlu-Pro-Arg-pNA), and wherein the hepsin inhibitor comprises at least one compound of forumulae (I)-(XIV) as described above. In a further embodiment the cell is a cancer cell that is selected from a prostate cancer cell, an ovarian carcinoma cell, an endometrial cancer cell and a renal carcinoma cell.

In another embodiment there is provided a method of inhibiting hepsin proteolytic activity, comprising contacting a hepsin polypeptide and a hepsin inhibitor under conditions and for a time sufficient for the hepsin inhibitor to interact specifically with the hepsin polypeptide, wherein the hepsin polypeptide is selected from (i) a polypeptide comprising the amino acid sequence set forth in any one of SEQ ID NOS:1-3, 6 and 9 (NP_892028; NP_002142; BC025716; AAI38810; AAB4221), (ii) a polypeptide comprising an amino acid sequence that is at least 85%, 90% or 95% identical to the polypeptide of (i) and that is capable of specific enzymatic cleavage of a chromogenic serine protease substrate that comprises L-pyroglutamyl-L-prolyl-L-arginine-p-nitroaniline hydrochloride (Glu-Pro-Arg-pNA), and (iii) a polypeptide that comprises a hepsin catalytic domain or a functional fragment thereof, said hepsin catalytic domain or functional fragment thereof comprising an amino acid sequence that is at least 80%, 85%, 90% or 95% identical to the amino acid sequence set forth in any one of SEQ ID NOS:5, 8 and 11 and that is capable of specific enzymatic cleavage of a chromogenic serine protease substrate that comprises L-pyroglutamyl-L-prolyl-L-arginine-p-nitroaniline hydrochloride (pyroGlu-Pro-Arg-pNA), and wherein the hepsin inhibitor comprises at least one compound of formulae (I)-(XIV) as described above.

In certain further embodiments of the methods described herein, the subject is a human. In certain other embodiments the subject is a mammal, which in certain further embodiments is selected from a non-human primate, a mouse, a rat, a rabbit, a dog, a cat, a hamster, a gerbil, a guinea pig, a goat, a sheep, a bovine, a swine and a horse.

These and other aspects of the invention will be evident upon reference to the following detailed description and attached drawings. All of the U.S. patents, U.S. patent application publications, U.S. patent applications, foreign patents, foreign patent applications and non-patent publications referred to in this specification and/or listed in the Application Data Sheet, are incorporated herein by reference in their entirety, as if each was incorporated individually. Aspects of the invention can be modified, if necessary, to employ concepts of the various patents, applications and publications to provide yet further embodiments of the invention.

BRIEF DESCRIPTION OF THE SEVERAL VIEWS OF THE DRAWINGS

(FIG. 1A) Chromatographically purified recombinant human hepsin was produced in *P. pastoris* and analyzed by silver stain of SDS-PAGE gel and immunoblotting with anti-hepsin catalytic domain antibodies. (FIG. 1B) Purified hepsin was proteolytically active. 0.4 nM purified hepsin was incubated with the chromogenic serine protease substrate Glu-Pro-Arg-pNA and enzyme activity was observed as a linear increase in absorbance at 405 nm over time.

FIG. 3 shows inhibition of hepsin activity by compounds identified in FIG. 2.

FIG. 5 shows hepsin-dependent pericellular serine protease assay and cellular toxicity of identified hepsin inhibitors.

FIG. 6 shows attenuation of hepsin-dependent pericellular protease activity by the identified hepsin inhibitors (FIG. 6A) HEK 293FT cells expressing wild-type murine hepsin (SEQ ID NO:9) were incubated for 24 hours with 20 µM (white bars) or 50 µM (grey bars) of biochemically identified hepsin inhibitors and pericellular proteolytic activity was determined as described for FIG. 5A. As some of the hepsin inhibitors significantly impacted the hepsin expression in HEK 293FT cells, data are displayed as pericellular proteolytic activity/expression level as percentage relative to vehicle treated wild-type hepsin expressing cells. (FIG. 6B) Immunoblot analysis of hepsin expression levels in HEK 293FT cells expressing wild-type and inactive hepsin and treated for 24 hours with indicated hepsin inhibitors. Loading was verified via immunoblot against β-actin.

DETAILED DESCRIPTION

Figure 1:
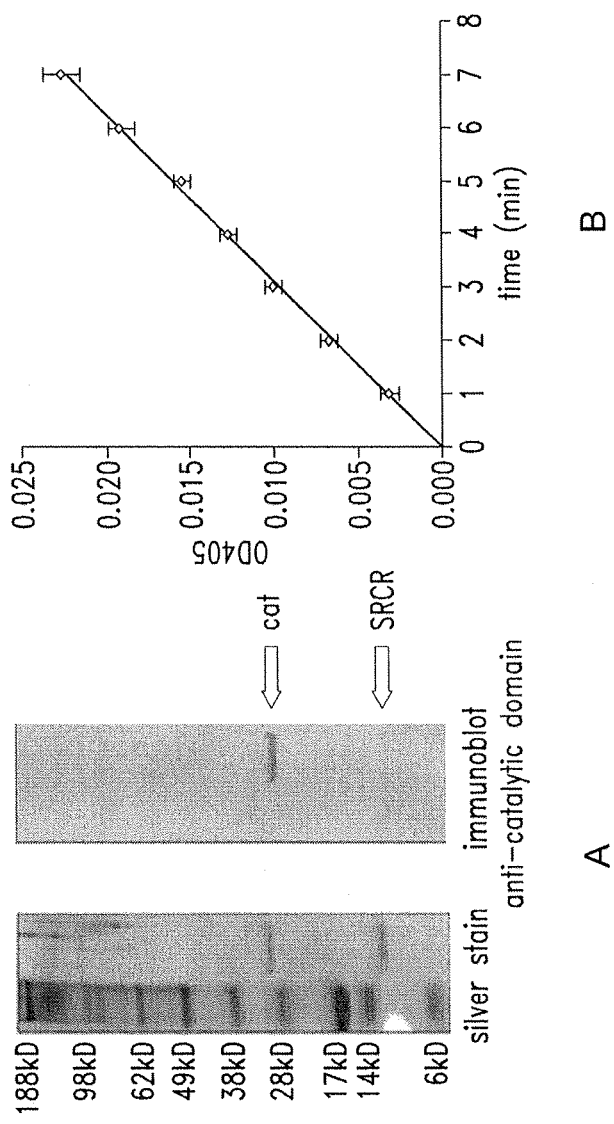
FIG. 1 shows characterization of recombinant active hepsin.

The presently disclosed invention embodiments relate to the first identification of small molecule compounds that specifically inhibit hepsin catalytic activity and that may be used as therapeutic agents and/or as lead compounds to develop targeted drugs to prevent or attenuate cancer progression or to block metastasis in a cancer that is characterized by hepsin overexpression (e.g., hepsin expression levels that are increased in a statistically significant manner relative to the expression levels in corresponding cells or tissues that are known to be disease-free). Preferred embodiments thus relate to prostate cancer, ovarian carcinoma, endometrial cancer and/or renal cell carcinoma, in each of which, as noted above, hepsin overexpression has been detected.

As described in greater detail hereinbelow, sixteen compounds have unexpectedly been identified that potently and specifically inhibit hepsin proteolytic activity, including four compounds that are able to attenuate hepsin dependent pericellular proteolytic activity with low or no general cellular toxicity, and two compounds that surprisingly are already established drugs for human use with known oral dosing strategies for indications entirely unrelated to cancer. These newly identified small molecules may find use as cancer therapeutics, and/or as lead compounds for generation of potent and specific drugs for the treatment of human cancers, and in particular for treating prostate cancer and/or other cancers that are characterized by hepsin overexpression, such as ovarian carcinoma, endometrial cancer and/or renal cell carcinoma.

Definitions

Certain chemical groups named herein may be preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

In addition to the foregoing, as used in the specification and appended claims, unless specified to the contrary, the following terms have the meaning indicated:

"Amino" refers to the —$NH_2$ radical.
"Cyano" refers to the —CN radical.
"Hydroxy" refers to the —OH radical.
"Imino" refers to the =NH substituent.

"Nitro" refers to the —NO$_2$ radical.

"Oxo" refers to the =O substituent.

"Thioxo" refers to the =S substituent.

"Trifluoromethyl" refers to the —CF$_3$ radical.

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$ (where t is 1 to 2), —S(O)$_t$OR$^{16}$ (where t is 1 to 2), —S(O)$_p$R$^{16}$ (where p is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$ (where t is 1 to 2), —S(O)$_t$OR$^{16}$ (where t is 1 to 2), —S(O)$_p$R$^{16}$ (where p is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl.

"Alkynyl" refers to a straight or branched hydrocarbon chain radical group comprising solely of carbon and hydrogen atoms, containing at least one triple bond, optionally containing at least one double bond, having from two to twelve carbon atoms, preferably two to eight carbon atoms and which is attached to the rest of the molecule by a single bond, for example, ethynyl, propynyl, butynyl, pentynyl, hexynyl, and the like. Unless stated otherwise specifically in the specification, an alkynyl group may be optionally substituted by one or more of the following substituents: alkyl, alkenyl, halo, haloalkenyl, cyano, nitro, aryl, cycloalkyl, heterocyclyl, heteroaryl, oxo, trimethylsilanyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$ (where t is 1 to 2), —S(O)$_t$OR$^{16}$ (where t is 1 to 2), —S(O)$_p$R$^{16}$ (where p is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$ (where t is 1 to 2), —S(O)$_t$OR$^{16}$ (where t is 1 to 2), —S(O)$_p$R$^{16}$ (where p is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$ (where t is 1 to 2), —S(O)$_t$OR$^{16}$ (where t is 1 to 2), —S(O)$_p$R$^{16}$ (where p is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl.

"Alkynylene" or "alkynylene chain" refers to a straight or branched divalent hydrocarbon chain linking the rest of the molecule to a radical group, consisting solely of carbon and hydrogen, containing at least one triple bond and having from two to twelve carbon atoms, e.g., propynylene, n-butynylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, an alkynylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$^{14}$, —OC(O)—R$^{14}$, —N($R^{14}$)$_2$, —C(O)$R^{14}$, —C(O)O$R^{14}$, —C(O)N($R^{14}$)$_2$, —N($R^{14}$)C(O)O$R^{16}$, —N($R^{14}$)C(O)$R^{16}$, —N($R^{14}$)S(O)$_t$$R^{16}$ (where t is 1 to 2), —S(O)$_t$O$R^{16}$ (where t is 1 to 2), —S(O)$_p$$R^{16}$ (where p is 0 to 2), and —S(O)$_t$N($R^{14}$)$_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{16}$ is alkyl, haloalkyl, cycloalkyl, cycloalkylalkyl, aryl, aralkyl, heterocyclyl, heterocyclylalkyl, heteroaryl or heteroarylalkyl.

"Alkoxy" refers to a radical of the formula —O$R_a$ where $R_a$ is an alkyl radical as defined above containing one to twelve carbon atoms. The alkyl part of the alkoxy radical may be optionally substituted as defined above for an alkyl radical.

"Alkoxyalkyl" refers to a radical of the formula —$R_b$—O—$R_a$ where $R_b$ is an alkylene chain as defined above and $R_a$ is an alkyl radical as defined above. The oxygen atom may be bonded to any carbon in the alkylene chain and in the alkyl radical. The alkyl part of the alkoxyalkyl radical may be optionally substituted as defined above for an alkyl group. The alkylene chain part of the alkoxyalkyl radical may be optionally substituted as defined above for an alkylene chain.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may included fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals optionally substituted by one or more substituents independently selected from the group consisting of alkyl, akenyl, halo, haloalkyl, haloalkenyl, cyano, nitro, aryl, heteroaryl, heteroarylalkyl, —$R^{15}$—O$R^{14}$, —$R^{15}$—OC(O)—$R^{14}$, —$R^{15}$—N($R^{14}$)$_2$, —$R^{15}$—C(O)$R^{14}$, —$R^{15}$—C(O)O$R^{14}$, —$R^{15}$—C(O)N($R^{14}$)$_2$, —$R^{15}$—N($R^{14}$)C(O)O$R^{16}$, —$R^{15}$—N($R^{14}$)C(O)$R^{16}$, —$R^{15}$—N($R^{14}$)S(O)$_t$$R^{16}$ (where t is 1 to 2), —$R^{15}$—N=C(O$R^{14}$)$R^{14}$, —$R^{15}$—S(O)$_t$O$R^{16}$ (where t is 1 to 2), —$R^{15}$—S(O)$_p$$R^{16}$ (where p is 0 to 2), and —$R^{15}$—S(O)$_t$N($R^{14}$)$_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. The alkylene chain part of the aralkyl radical may be optionally substituted as described above for an alkylene chain. The aryl part of the aralkyl radical may be optionally substituted as described above for an aryl group.

"Aralkenyl" refers to a radical of the formula —$R_d$—$R_e$ where $R_d$ is an alkenylene chain as defined above and $R_c$ is one or more aryl radicals as defined above. The aryl part of the aralkenyl radical may be optionally substituted as described above for an aryl group. The alkenylene chain part of the aralkenyl radical may be optionally substituted as defined above for an alkenylene group.

"Aralkynyl" refers to a radical of the formula —$R_e$$R_c$ where $R_e$ is an alkynylene chain as defined above and $R_c$ is one or more aryl radicals as defined above. The aryl part of the aralkynyl radical may be optionally substituted as described above for an aryl group. The alkynylene chain part of the aralkynyl radical may be optionally substituted as defined above for an alkynylene chain.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, the term "cycloalkyl" is meant to include cycloalkyl radicals which are optionally substituted by one or more substituents independently selected from the group consisting of alkyl, alkenyl, halo, haloalkyl, haloalkenyl, cyano, nitro, oxo, aryl, aralkyl, cycloalkyl, cycloalkylalkyl, heterocyclyl, heterocyclylalkyl, heteroaryl, heteroarylalkyl, —$R^{15}$—O$R^{14}$, —$R^{15}$—OC(O)—$R^{14}$, —$R^{15}$—N($R^{14}$)$_2$, —$R^{15}$—C(O)$R^{14}$, —$R^{15}$—C(O)O$R^{14}$, —$R^{15}$—C(O)N($R^{14}$)$_2$, —$R^{15}$—N($R^{14}$)C(O)O$R^{16}$, —$R^{15}$—N($R^{14}$)C(O)$R^{16}$, —$R^{15}$—N($R^{14}$)S(O)$_t$$R^{16}$ (where t is 1 to 2), —$R^{15}$—N=C(O$R^{14}$)$R^{14}$, —$R^{15}$—S(O)$_t$O$R^{16}$ (where t is 1 to 2), —$R^{15}$—S(O)$_p$$R^{16}$ (where p is 0 to 2), and —$R^{15}$—S(O)$_t$N($R^{14}$)$_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl.

"Cycloalkylalkyl" refers to a radical of the formula —$R_b$$R_g$ where $R_b$ is an alkylene chain as defined above and $R_g$ is a cycloalkyl radical as defined above. The alkylene chain and the cycloalkyl radical may be optionally substituted as defined above.

"Cycloalkylalkenyl" refers to a radical of the formula —$R_d$$R_g$ where $R_d$ is an alkenylene chain as defined above and $R_g$ is a cycloalkyl radical as defined above. The alkenylene chain and the cycloalkyl radical may be optionally substituted as defined above.

"Cycloalkylalkynyl" refers to a radical of the formula —$R_e$$R_g$ where $R_e$ is an alkynylene radical as defined above and $R_g$ is a cycloalkyl radical as defined above. The alkynylene chain and the cycloalkyl radical may be optionally substituted as defined above.

"Fused" refers to any ring system described herein which is fused to an existing ring structure in the compounds of the invention. When the fused ring system is a heterocyclyl or a heteroaryl, any carbon atom on the existing ring structure which becomes part of the fused ring system may be replaced with a nitrogen atom.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Haloalkenyl" refers to an alkenyl radical, as defined above, that is substituted by one or more halo radicals, as defined above. The alkenyl part of the haloalkyl radical may be optionally substituted as defined above for an alkenyl group.

"Haloalkynyl" refers to an alkynyl radical, as defined above, that is substituted by one or more halo radicals, as defined above. The alkynyl part of the haloalkyl radical may be optionally substituted as defined above for an alkynyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrrolidinonyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{16}$, $-R^{15}-N(R^{14})C(O)R^{16}$, $-R^{15}-N(R^{14})S(O)_tR^{16}$ (where t is 1 to 2), $-R^{15}-N=C(OR^{14})R^{14}$, $-R^{15}-S(O)_tOR^{16}$ (where t is 1 to 2), $-R^{15}-S(O)_pR^{16}$ (where p is 0 to 2), and $-R^{15}-S(O)_tN(R^{14})_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical may be optionally substituted as described above for heterocyclyl radicals.

"Heterocyclylalkyl" refers to a radical of the formula $-R_bR_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. The alkylene chain of the heterocyclylalkyl radical may be optionally substituted as defined above for an alkyene chain. The heterocyclyl part of the heterocyclylalkyl radical may be optionally substituted as defined above for a heterocyclyl group.

"Heterocyclylalkenyl" refers to a radical of the formula $-R_dR_h$ where $R_d$ is an alkenylene chain as defined above and $R_h$ is a heterocyclyl radical as defined above, and if the heterocyclyl is a nitrogen-containing heterocyclyl, the heterocyclyl may be attached to the alkenylene chain at the nitrogen atom. The alkenylene chain of the heterocyclylalkenyl radical may be optionally substituted as defined above for an alkenylene chain. The heterocyclyl part of the heterocyclylalkenyl radical may be optionally substituted as defined above for a heterocyclyl group.

"Heterocyclylalkynyl" refers to a radical of the formula $-R_eR_h$ where $R_e$ is an alkynylene chain as defined above and $R_h$ is a heterocyclyl radical as defined above, and if the heterocyclyl is a nitrogen-containing heterocyclyl, the heterocyclyl may be attached to the alkynyl radical at the nitrogen atom. The alkynylene chain part of the heterocyclylalkynyl radical may be optionally substituted as defined above for an alkynylene chain. The heterocyclyl part of the heterocyclylalkynyl radical may be optionally substituted as defined above for a heterocyclyl group.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, or tricyclic ring system, which may include fused or bridged ring systems; and any nitrogen, carbon or sulfur atom in the heteroaryl radical may be optionally oxidized; and any nitrogen atom may be optionally quaternized. For purposes of this invention, the aromatic ring of the heteroaryl radical need not contain a heteroatom, as long as one ring of the heteroaryl radical contains a heteroatom. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, 2-thioxobenzimidazolyl, triazolyl, tetrazolyl, triazinyl, and thiophenyl (i.e. thienyl). Unless stated otherwise specifically in the specification, the term "heteroaryl" is meant to include heteroaryl radicals as defined above which are optionally substituted by one or more substituents selected from the group consisting of alkyl, alkenyl, alkoxy, halo, haloalkyl, haloalkenyl, cyano, oxo, thioxo, nitro, thioxo, aryl, aralkyl, cycloalkyl, cycloalkylalkyl, heterocyclyl, heterocyclylalkyl, heteroaryl, heteroarylalkyl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{16}$, $-R^{15}-N(R^{14})C(O)R^{16}$, $-R^{15}-N(R^{14})S(O)_tR^{16}$ (where t is 1 to 2), $-R^{15}-N=C(OR^{14})R^{14}$, $-R^{15}-S(O)_tOR^{16}$ (where t is 1 to 2), —R$^{15}$—S(O)$_p$R$^{16}$ (where p is 0 to 2), and —R$^{15}$—S(O)$_t$N(R$^{14}$)$_2$ (where t is 1 to 2) where each R$^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each R$^{15}$ is independently a direct bond or a straight or branched alkylene or alkenylene chain; and each R$^{16}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical may be optionally substituted as described above for heteroaryl radicals.

"Heteroarylalkyl" refers to a radical of the formula —R$_b$R$_i$ where R$_b$ is an alkylene chain as defined above and R$_i$ is a heteroaryl radical as defined above. The heteroaryl part of the heteroarylalkyl radical may be optionally substituted as defined above for a heteroaryl group. The alkylene chain part of the heteroarylalkyl radical may be optionally substituted as defined above for an alkylene chain.

"Heteroarylalkenyl" refers to a radical of the formula —R$_d$R$_i$ where R$_d$ is an alkenylene chain as defined above and R$_i$ is a heteroaryl radical as defined above. The heteroaryl part of the heteroarylalkenyl radical may be optionally substituted as defined above for a heteroaryl group. The alkenylene chain part of the heteroarylalkenyl radical may be optionally substituted as defined above for an alkenylene chain.

"Heteroarylalkynyl" refers to a radical of the formula —R$_e$R$_i$ where R$_e$ is an alkynylene chain as defined above and R$_i$ is a heteroaryl radical as defined above. The heteroaryl part of the heteroarylalkynyl radical may be optionally substituted as defined above for a heteroaryl group. The alkynylene chain part of the heteroarylalkynyl radical may be optionally substituted as defined above for an alkynylene chain.

"Hydroxyalkyl" refers to an alkyl radical, as defined above, substituted by one or more hydroxy groups.

The invention disclosed herein is also meant to encompass all pharmaceutically acceptable compounds of the invention being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action on the selected target, or binding affinity to pharmacologically important site of action on the selected target. Certain isotopically-labelled compounds of the invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of the invention can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising contacting a compound of this invention with a mammal for a period of time sufficient to yield a metabolic product thereof. Such products are typically are identified by administering a radiolabelled compound of the invention in a detectable dose to an animal, such as a rat, mouse, guinea pig, monkey, or to a human, allowing sufficient time for metabolism to occur, and isolating its coversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans, and also includes domesticated animals such as laboratory animals, livestock and household pets (e.g., cats, dogs, swine, cattle, sheep, goats, horses, rabbits), and also includes non-domesticated animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. When a functional group is described as "optionally substituted," and in turn, substitutents on the functional group are also "optionally substituted" and so on, for the purposes of this invention, such iterations are limited to five.

"Pharmaceutically acceptable excipient, carrier, or diluent" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of a disease or condition of interest in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest (e.g., cancer, cancer progression and/or metastasis) in a mammal, preferably a human, known to have or suspected of being at risk for having the disease or condition of interest, and includes:

(i) preventing the disease or condition from occurring in a mammal, in particular, when such mammal is predisposed to the condition or suspected of being at risk for the condition, but has not yet been diagnosed as having it, and whereby the disease or condition cannot be detected according to existing accepted criteria for determining whether a specific disease or condition is present;

(ii) inhibiting the disease or condition, i.e., arresting its development, for instance, preventing progression of a cancer from an early defined stage to a more advanced defined stage, or attenuating progression (e.g., decreasing the frequency of such progression events in a statistically significant manner, or increasing the timeframe in which such progression occurs in a statistically significant manner), or interfering with one or more metastatic events to completely or partially block or attenuate metastasis, for instance, to substantially impair cancer progression or metastasis, which may refer to substantial and statistically significant, but not necessarily complete, inhibition of progression or metastasis, e.g., at least 50%, 60%, 70%, 80%, 85%, 90%, 95% or greater inhibition relative to appropriate untreated controls;

(iii) relieving the disease or condition, i.e., causing regression of the disease or condition; or (iv) relieving the symptoms resulting from the disease or condition, i.e., relieving pain without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians. In preferred embodiments the present invention contemplates methods of treating cancer that is characterized by hepsin overexpression in cancer cells, such as prostate cancer, ovarian carcinoma, endometrial cancer and renal cell carcinoma.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The chemical naming protocol and structure diagrams used herein are a modified form of the I.U.P.A.C. nomenclature system. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

Thus, by way of a non-limiting example, a compound of formula (II), as set forth above in the Summary of the Invention, wherein n is 2, each $R^1$ is chloro, $R^3$ and $R^4$ are both hydrogen and $R^5$ is 4-bromophenyl, e.g., a compound of the following formula (II-2):

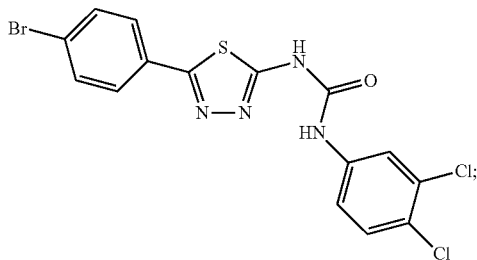

(II-2)

is named herein as N-[5-(4-bromophenyl)-1,3,4-thiadiazol-2-yl]-N'-(3,4-dichlorophenyl)urea.

Embodiments of the Invention

Of the various aspects of the invention set forth above in the Summary of the Invention, certain embodiments are preferred.

In another embodiment, the hepsin inhibitor utilized in the methods of the invention comprises a compound of formula (I), as set forth above in the Summary of the Invention:

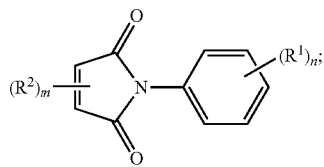

(I)

wherein:
m is 1 or 2;
n is 1, 2, 3, 4 or 5;
each $R^1$ is independently selected from the group consisting of hydrogen, alkyl, halo, haloalkyl, optionally substituted aryl, optionally substituted aralkyl, —$OR^7$, —CN, —C(O)$R^7$, —C(O)$OR^7$, —C(O)N($R^7$)$R^8$, —$NO_2$, —N($R^7$)$R^8$, —N($R^7$)C(O)$R^8$, and —N($R^7$)C(O)$OR^8$;
each $R^2$ is independently selected from the group consisting of hydrogen, alkyl, halo, haloalkyl, optionally substituted aryl and optionally substituted aralkyl; and
each $R^7$ and $R^8$ is independently selected from the group consisting of hydrogen, alkyl, optionally substituted aryl and optionally substituted aralkyl;
as a single stereoisomer or a mixture thereof;
or a pharmaceutically acceptable salt thereof.

In another embodiment of the invention, the hepsin inhibitor utilized in the methods of the invention comprises a compound of formula (I), as set forth above, wherein:
m is 1 or 2;
n is 1;
$R^1$ is selected from the group consisting of hydrogen, —$NO_2$, —N($R^7$)$R^8$, —N($R^7$)C(O)$R^8$, and —N($R^7$)C(O)$OR^8$;
$R^2$ is selected from the group consisting of hydrogen and alkyl; and
each $R^7$ and $R^8$ is independently selected from the group consisting of hydrogen and alkyl.

In another embodiment of the invention, the hepsin inhibitor utilized in the methods of the invention comprises a compound of formula (I) having the following formula (I-1):

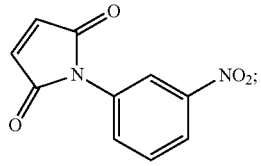

(I-1)

as a single stereoisomer or a mixture thereof; or a pharmaceutically acceptable salt thereof. Compound (I-1) is named herein as 1-(3-nitrophenyl)-1H-pyrrole-2,5-dione.

In another embodiment, the hepsin inhibitor utilized in the methods of the invention comprises a compound of formula (II), as set forth above in the Summary of the Invention:

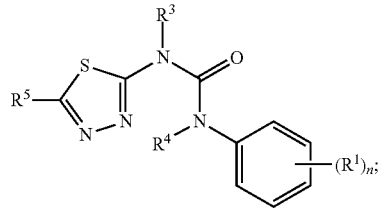

(II)

wherein:
n is 1, 2, 3, 4 or 5;
each $R^1$ is independently selected from the group consisting of hydrogen, alkyl, halo, haloalkyl, optionally substituted aryl, optionally substituted aralkyl, —$OR^7$, —CN, —C(O)$R^7$, —C(O)$OR^7$, —C(O)N($R^7$)$R^8$, —$NO_2$, —N($R^7$)$R^8$, —N($R^7$)C(O)$R^8$, and —N($R^7$)C(O)$OR^8$;
$R^3$ and $R^4$ are each independently selected from the group consisting of hydrogen, alkyl, optionally substituted aryl and optionally substituted aralkyl;
$R^5$ is selected from the group consisting of hydrogen, optionally substituted aryl, optionally substituted aralkyl and —$R^9$—$OR^7$;
each $R^7$ and $R^8$ is independently selected from the group consisting of hydrogen, alkyl, optionally substituted aryl and optionally substituted aralkyl; and
$R^9$ is a straight or branched alkylene chain;
as a single stereoisomer or a mixture thereof;
or a pharmaceutically acceptable salt thereof.

In another embodiment of the invention, the hepsin inhibitor utilized in the methods of the invention comprises a compound of formula (II), as set forth above, wherein:

n is 1 or 2, 3, 4 or 5;
each $R^1$ is independently selected from the group consisting of hydrogen and halo;
$R^3$ and $R^4$ are each independently selected from the group consisting of hydrogen and alkyl;
$R^5$ is selected from the group consisting of —$R^9$—$OR^7$ and phenyl optionally substituted with one or more substituents selected from the group consisting of alkyl, halo and haloalkyl;
$R^7$ is phenyl optionally substituted with one or more substituents selected from the group consisting of alkyl, halo and haloalkyl; and
$R^9$ is a straight alkylene chain.

In another embodiment of the invention, the hepsin inhibitor utilized in the methods of the invention comprises a compound of formula (II), as set forth above, wherein:
n is 1 or 2, 3, 4 or 5;
each $R^1$ is chloro;
$R^3$ and $R^4$ are each independently selected from the group consisting of hydrogen and alkyl;
$R^5$ is —$CH_2$—$OR^7$ or phenyl optionally substituted with one or more halo;
$R^7$ is phenyl optionally substituted with one or more alkyl; and
$R^9$ is a methylene chain.

In another embodiment of the invention, the hepsin inhibitor utilized in the methods of the invention comprises a compound of formula (II) having the following formula (II-1):

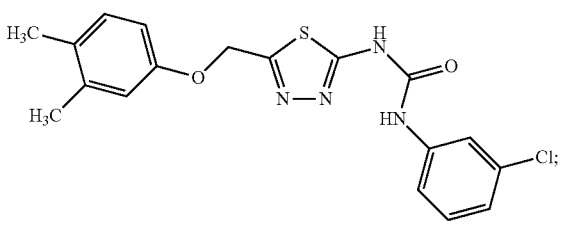

(II-1)

as a single stereoisomer or a mixture thereof; or a pharmaceutically acceptable salt thereof. Compound (II-1) is named herein as N-(3-chlorophenyl)-N'-{5-[(3,4-dimethylphenoxy)methyl]-1,3,4-thiadiazol-2-yl}urea.

In another embodiment of the invention, the hepsin inhibitor utilized in the methods of the invention comprises a compound of formula (II) having the following formula (II-2):

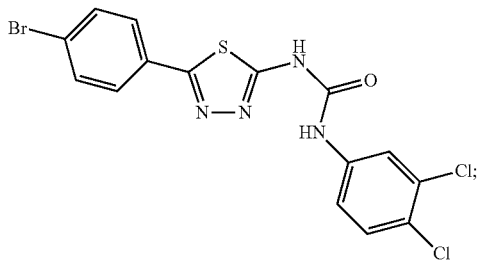

(II-2)

as a single stereoisomer or a mixture thereof; or a pharmaceutically acceptable salt thereof. Compound (II-2) is named herein as N-[5-(4-bromophenyl)-1,3,4-thiadiazol-2-yl]-N'-(3,4-dichlorophenyl)urea.

In another embodiment, the hepsin inhibitor utilized in the methods of the invention comprises a compound of formula (III), as set forth above in the Summary of the Invention:

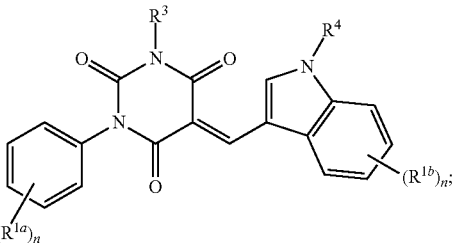

(III)

wherein:
each n is 1, 2, 3, 4 or 5;
each $R^{1a}$ and $R^{1b}$ is independently selected from the group consisting of hydrogen, alkyl, halo, haloalkyl, optionally substituted aryl, optionally substituted aralkyl, —$OR^7$, —CN, —$C(O)R^7$, —$C(O)OR^7$, —$C(O)N(R^7)R^8$, —$NO_2$, —$N(R^7)R^8$, —$N(R^7)C(O)R^8$, and —$N(R^7)C(O)OR^8$;
$R^3$ and $R^4$ are each independently selected from the group consisting of hydrogen, alkyl, optionally substituted aryl and optionally substituted aralkyl; and
each $R^7$ and $R^8$ is independently selected from the group consisting of hydrogen, alkyl, optionally substituted aryl and optionally substituted aralkyl;
as a single stereoisomer or a mixture thereof;
or a pharmaceutically acceptable salt thereof.

In another embodiment of the invention, the hepsin inhibitor utilized in the methods of the invention comprises a compound of formula (III), as set forth above, wherein:
each n is 1;
$R^{1a}$ and $R^{1b}$ are each independently selected from the group consisting of hydrogen, alkyl, halo and haloalkyl; and
$R^3$ and $R^4$ are each independently selected from the group consisting of hydrogen and alkyl.

In another embodiment of the invention, the hepsin inhibitor utilized in the methods of the invention comprises a compound of formula (III) having the following formula (III-1):

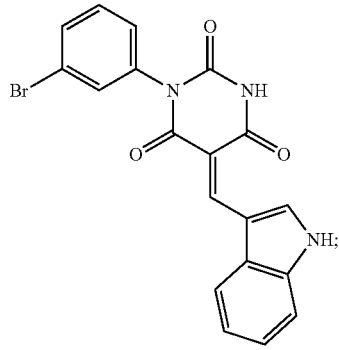

(III-1)

as a single stereoisomer or a mixture thereof; or a pharmaceutically acceptable salt thereof. Compound (III-1) is named herein as 1-(3-bromophenyl)-5-(1H-indol-3-yl)methylene)-2,4,6(1H,3H,5H)pyrimidinetrione.

In another embodiment, the hepsin inhibitor utilized in the methods of the invention comprises a compound of formula (IV), as set forth above in the Summary of the Invention:

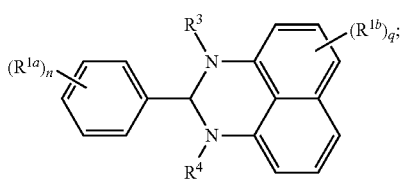
(IV)

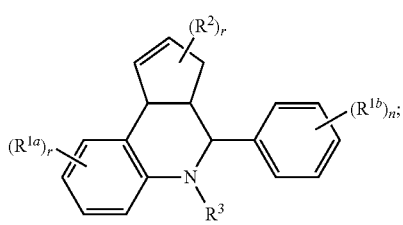
(V)

wherein:

n is 1, 2, 3, 4 or 5;

q is 1, 2, 3, 4, 5 or 6;

each $R^{1a}$ and $R^{1b}$ is independently selected from the group consisting of hydrogen, alkyl, halo, haloalkyl, optionally substituted aryl, optionally substituted aralkyl, —$OR^7$, —CN, —$C(O)R^7$, —$C(O)OR^7$, —$C(O)N(R^7)R^8$, —$NO_2$, —$N(R^7)R^8$, —$N(R^7)C(O)R^8$, and —$N(R^7)C(O)OR^8$;

$R^3$ and $R^4$ are each independently selected from the group consisting of hydrogen, alkyl, optionally substituted aryl and optionally substituted aralkyl; and each $R^7$ and $R^8$ is independently selected from the group consisting of hydrogen, alkyl, optionally substituted aryl and optionally substituted aralkyl;

as a single stereoisomer or a mixture thereof;

or a pharmaceutically acceptable salt thereof.

In another embodiment of the invention, the hepsin inhibitor utilized in the methods of the invention comprises a compound of formula (IV), as set forth above, wherein:

n is 1;

q is 1, $R^{1a}$ and $R^{1b}$ are each independently selected from the group consisting of hydrogen and alkyl; and $R^3$ and $R^4$ are each independently selected from the group consisting of hydrogen and alkyl.

In another embodiment of the invention, the hepsin inhibitor utilized in the methods of the invention comprises a compound of formula (IV) having the following formula (IV-1):

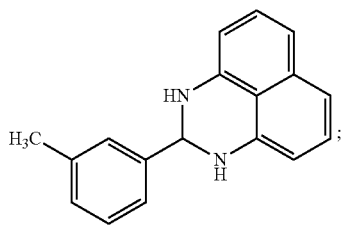
(IV-1)

as a single stereoisomer or a mixture thereof; or a pharmaceutically acceptable salt thereof. Compound (IV-1) is named herein as 2-(3-methylphenyl)-2,3-dihydro-1H-perimidine.

In another embodiment, the hepsin inhibitor utilized in the methods of the invention comprises a compound of formula (V), as set forth above in the Summary of the Invention:

wherein:

n is 1, 2, 3, 4 or 5;

each r is 1, 2, 3 or 4;

each $R^{1a}$ and $R^{1b}$ is independently selected from the group consisting of hydrogen, alkyl, halo, haloalkyl, optionally substituted aryl, optionally substituted aralkyl, —$OR^7$, —CN, —$C(O)R^7$, —$C(O)OR^7$, —$C(O)N(R^7)R^8$, —$NO_2$, —$N(R^7)R^8$, —$N(R^7)C(O)R^8$, and —$N(R^7)C(O)OR^8$;

each $R^2$ is independently selected from the group consisting of hydrogen, alkyl, halo, haloalkyl, optionally substituted aryl and optionally substituted aralkyl;

$R^3$ is selected from the group consisting of hydrogen, alkyl, optionally substituted aryl and optionally substituted aralkyl; and each $R^7$ and $R^8$ is independently selected from the group consisting of hydrogen, alkyl, optionally substituted aryl and optionally substituted aralkyl;

as a single stereoisomer or a mixture thereof;

or a pharmaceutically acceptable salt thereof.

In another embodiment of the invention, the hepsin inhibitor utilized in the methods of the invention comprises a compound of formula (V), as set forth above, wherein:

n is 1;

each r is 1;

$R^{1a}$ and $R^{1b}$ are each independently selected from the group consisting of hydrogen, halo, haloalkyl and —$NO_2$;

$R^2$ is selected from the group consisting of hydrogen and alkyl; and $R^3$ is selected from the group consisting of hydrogen and alkyl.

In another embodiment of the invention, the hepsin inhibitor utilized in the methods of the invention comprises a compound of formula (V) having the following formula (V-1):

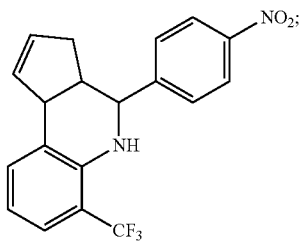
(V-1)

as a single stereoisomer or a mixture thereof; or a pharmaceutically acceptable salt thereof. Compound (V-1) is named herein as 4-(4-nitrophenyl)-6-(trifluoromethyl)-3a,4,5,9b-tetrahydro-3H-cyclopenta[c]quinoline.

In another embodiment of the invention, the hepsin inhibitor utilized in the methods of the invention comprises a compound of formula (V) having the following formula (V-2):

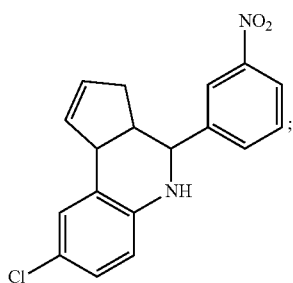

(V-2)

as a single stereoisomer or a mixture thereof; or a pharmaceutically acceptable salt thereof. Compound (V-2) is named herein as 8-chloro-4-(3-nitrophenyl)-3a,4,5,9b-tetrahydro-3H-cyclopenta[c]quinoline.

In another embodiment, the hepsin inhibitor utilized in the methods of the invention comprises a compound of formula (VI), as set forth above in the Summary of the Invention:

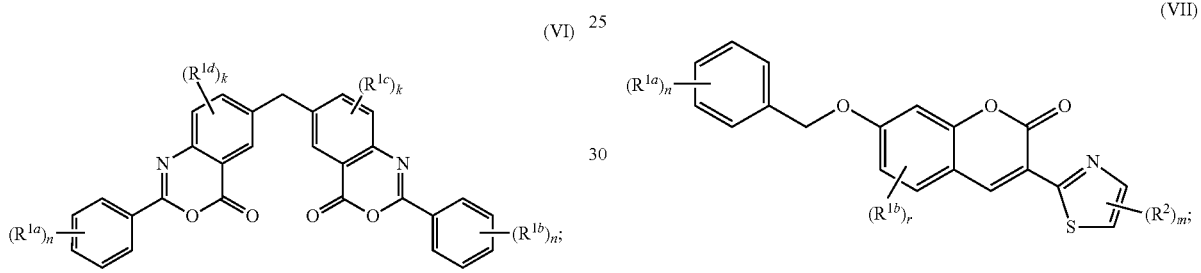

(VI)

wherein:

each k is 1, 2 or 3;

each n is 1, 2, 3, 4 or 5;

each $R^{1a}$, $R^{1c}$ and $R^{1d}$ is independently selected from the group consisting of hydrogen, alkyl, halo, haloalkyl, optionally substituted aryl, optionally substituted aralkyl, —$OR^7$, —CN, —$C(O)R^7$, —$C(O)OR^7$, —$C(O)N(R^7)R^8$, —$NO_2$, —$N(R^7)R^8$, —$N(R^7)C(O)R^8$, and —$N(R^7)C(O)OR^8$; and each $R^7$ and $R^8$ is independently selected from the group consisting of hydrogen, alkyl, optionally substituted aryl and optionally substituted aralkyl;

as a single stereoisomer or a mixture thereof;

or a pharmaceutically acceptable salt thereof.

In another embodiment of the invention, the hepsin inhibitor utilized in the methods of the invention comprises a compound of formula (VI), as set forth above, wherein:

each k is 1;

each n is 1; and each $R^{1a}$, $R^{1b}$, $R^{1c}$ and $R^{1d}$ is independently selected from the group consisting of hydrogen and halo.

In another embodiment of the invention, the hepsin inhibitor utilized in the methods of the invention comprises a compound of formula (VI) having the following formula (VI-1):

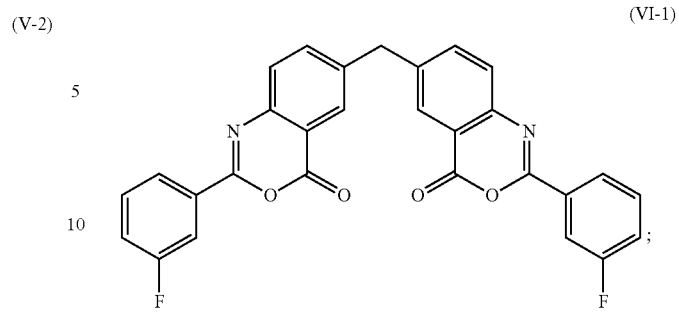

(VI-1)

as a single stereoisomer or a mixture thereof; or a pharmaceutically acceptable salt thereof. Compound (VI-1) is named herein as 6,6'-methylenebis[2-(3-fluorophenyl)-4H-3,1-benzooxazin-4-one].

In another embodiment, the hepsin inhibitor utilized in the methods of the invention comprises a compound of formula (VII), as set forth above in the Summary of the Invention:

(VII)

wherein:

m is 1 or 2;

n is 1, 2, 3, 4 or 5;

r is 1, 2, 3 or 4;

each $R^{1a}$ and $R^{1b}$ is independently selected from the group consisting of hydrogen, alkyl, halo, haloalkyl, optionally substituted aryl, optionally substituted aralkyl, —$OR^7$, —CN, —$C(O)R^7$, —$C(O)OR^7$, —$C(O)N(R^7)R^8$, —$NO_2$, —$N(R^7)R^8$, —$N(R^7)C(O)R^8$, and —$N(R^7)C(O)OR^8$;

each $R^2$ is independently selected from the group consisting of hydrogen, alkyl, halo, haloalkyl, optionally substituted aryl and optionally substituted aralkyl; and each $R^7$ and $R^8$ is independently selected from the group consisting of hydrogen, alkyl, optionally substituted aryl and optionally substituted aralkyl;

as a single stereoisomer or a mixture thereof;

or a pharmaceutically acceptable salt thereof.

In another embodiment of the invention, the hepsin inhibitor utilized in the methods of the invention comprises a compound of formula (VII), as set forth above, wherein:

m is 1;

n is 5;

r is 1;

each $R^{1a}$ is halo and $R^{1b}$ is independently selected from the group consisting of hydrogen and alkyl; and $R^2$ is selected from the group consisting of hydrogen, alkyl, haloalkyl.

In another embodiment of the invention, the hepsin inhibitor utilized in the methods of the invention comprises a compound of formula (VII) having the following formula (VII-1):

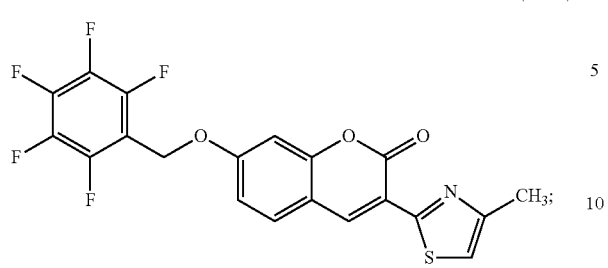

(VII-1)

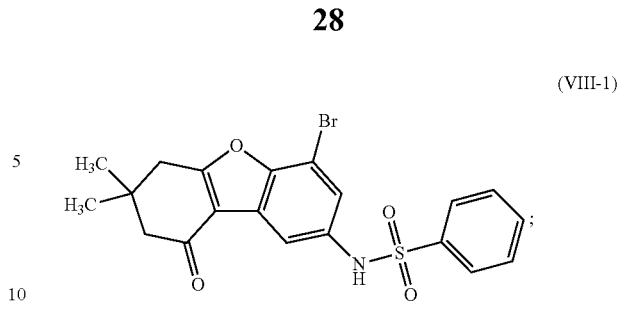

(VIII-1)

as a single stereoisomer or a mixture thereof; or a pharmaceutically acceptable salt thereof. Compound (VII-1) is named herein as 3-(4-methyl-1,3-thiazol-2-yl)-7-[(pentafluorobenzyl)oxy]-2H-chromen-2-one.

In another embodiment, the hepsin inhibitor utilized in the methods of the invention comprises a compound of formula (VIII), as set forth above in the Summary of the Invention:

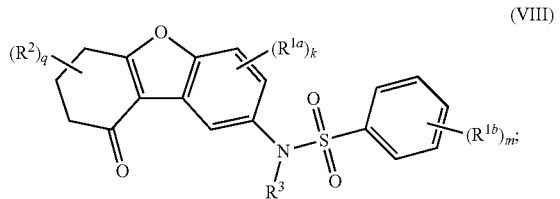

(VIII)

wherein:
k is 1, 2 or 3;
m is 1 or 2;
q is 1, 2, 3, 4, 5 or 6;
each $R^{1a}$ and $R^{1b}$ is independently selected from the group consisting of hydrogen, alkyl, halo, haloalkyl, optionally substituted aryl, optionally substituted aralkyl, —$OR^7$, —CN, —C(O)$R^7$, —C(O)O$R^7$, —C(O)N($R^7$)$R^8$, —$NO_2$, —N($R^7$)$R^8$, —N($R^7$)C(O)$R^8$, and —N($R^7$)C(O)O$R^8$;
each $R^2$ is independently selected from the group consisting of hydrogen, alkyl, halo, haloalkyl, optionally substituted aryl and optionally substituted aralkyl;
$R^3$ is selected from the group consisting of hydrogen, alkyl, optionally substituted aryl and optionally substituted aralkyl; and
each $R^7$ and $R^8$ is independently selected from the group consisting of hydrogen, alkyl, optionally substituted aryl and optionally substituted aralkyl;
as a single stereoisomer or a mixture thereof;
or a pharmaceutically acceptable salt thereof.

In another embodiment of the invention, the hepsin inhibitor utilized in the methods of the invention comprises a compound of formula (VIII), as set forth above, wherein:
k is 1;
m is 1;
q is 2;
$R^{1a}$ and $R^{1b}$ are each independently selected from the group consisting of hydrogen and halo;
each $R^2$ is alkyl; and
$R^3$ is selected from the group consisting of hydrogen and alkyl.

In another embodiment of the invention, the hepsin inhibitor utilized in the methods of the invention comprises a compound of formula (VIII) having the following formula (VIII-1):

as a single stereoisomer or a mixture thereof; or a pharmaceutically acceptable salt thereof. Compound (VIII-1) is named herein as N-(4-bromo-7,7-dimethyl-9-oxo-6,7,8,9-tetrahydrodibenzo[b,d]furan-2-yl)benzenesulfonamide.

In another embodiment, the hepsin inhibitor utilized in the methods of the invention comprises a compound of formula (IX), as set forth above in the Summary of the Invention:

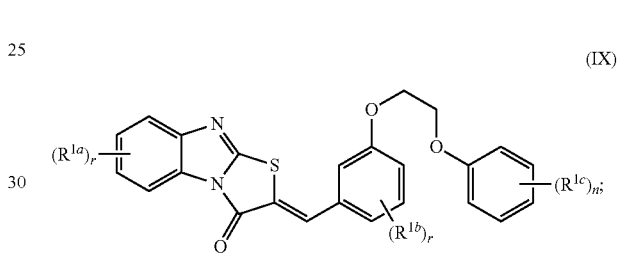

(IX)

wherein:
n is 1, 2, 3, 4 or 5;
each r is 1, 2, 3 or 4;
each $R^{1a}$, $R^{1b}$ and $R^{1b}$ is independently selected from the group consisting of hydrogen, alkyl, halo, haloalkyl, optionally substituted aryl, optionally substituted aralkyl, —$OR^7$, —CN, —C(O)$R^7$, —C(O)O$R^7$, —C(O)N($R^7$)$R^8$, —$NO_2$, —N($R^7$)$R^8$, —N($R^7$)C(O)$R^8$, and —N($R^7$)C(O)O$R^8$; and
each $R^7$ and $R^8$ is independently selected from the group consisting of hydrogen, alkyl, optionally substituted aryl and optionally substituted aralkyl; and
as a single stereoisomer or a mixture thereof;
or a pharmaceutically acceptable salt thereof.

In another embodiment of the invention, the hepsin inhibitor utilized in the methods of the invention comprises a compound of formula (IX), as set forth above, wherein:
n is 1;
each r is 1;
each $R^{1a}$ and $R^{1b}$ is independently selected from the group consisting of hydrogen, alkyl, halo and haloalkyl;
$R^{1c}$ is —$OR^7$; and
$R^7$ is selected from the group consisting of hydrogen and alkyl.

In another embodiment of the invention, the hepsin inhibitor utilized in the methods of the invention comprises a compound of formula (IX) having the following formula (IX-1):

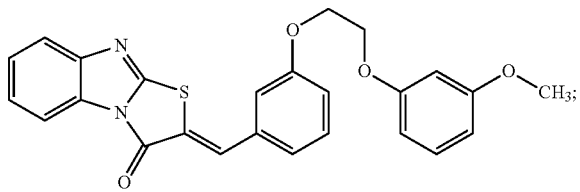

(IX-1)

as a single stereoisomer or a mixture thereof; or a pharmaceutically acceptable salt thereof. Compound (IX-1) is named herein as 2-{3-[2-(3-methoxyphenoxy)ethoxy]benzylidene}[1,3]thiazolo[3,2-a]benzimidazol-3(2H)-one.

In another embodiment, the hepsin inhibitor utilized in the methods of the invention comprises a compound of formula (X), as set forth above in the Summary of the Invention:

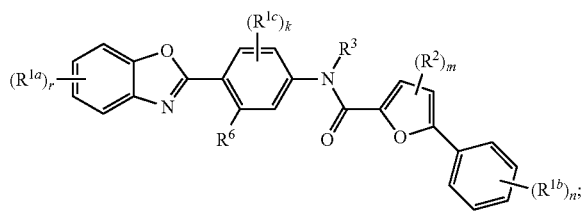

(X)

wherein:
k is 1, 2 or 3;
m is 1 or 2;
n is 1, 2, 3, 4 or 5;
r is 1, 2, 3 or 4;
each $R^{1a}$, $R^{1b}$ and $R^{1c}$ is independently selected from the group consisting of hydrogen, alkyl, halo, haloalkyl, optionally substituted aryl, optionally substituted aralkyl, —$OR^7$, —CN, —$C(O)R^7$, —$C(O)OR^7$, —$C(O)N(R^7)R^8$, —$NO_2$, —$N(R^7)R^8$, —$N(R^7)C(O)R^8$, and —$N(R^7)C(O)OR^8$;
each $R^2$ is independently selected from the group consisting of hydrogen, alkyl, halo, haloalkyl, optionally substituted aryl and optionally substituted aralkyl;
$R^3$ is selected from the group consisting of hydrogen, alkyl, optionally substituted aryl and optionally substituted aralkyl;
$R^6$ is selected from the group consisting of hydrogen and —$OR^7$; and
each $R^7$ and $R^8$ is independently selected from the group consisting of hydrogen, alkyl, optionally substituted aryl and optionally substituted aralkyl; and
as a single stereoisomer or a mixture thereof;
or a pharmaceutically acceptable salt thereof.

In another embodiment of the invention, the hepsin inhibitor utilized in the methods of the invention comprises a compound of formula (X), as set forth above, wherein:
k is 1;
m is 1;
n is 1;
r is 1;
$R^{1a}$ and $R^{1b}$ are each independently selected from the group consisting of hydrogen, alkyl, halo and haloalkyl;
$R^{1b}$ is selected from the group consisting of hydrogen, —$NO_2$ and —$N(R^7)R^8$;

$R^2$ is selected from the group consisting of hydrogen and alkyl;
$R^3$ is selected from the group consisting of hydrogen and alkyl;
$R^6$ is —$OR^7$; and
each $R^7$ and $R^8$ is independently selected from the group consisting of hydrogen and alkyl.

In another embodiment of the invention, the hepsin inhibitor utilized in the methods of the invention comprises a compound of formula (X) having the following formula (X-1):

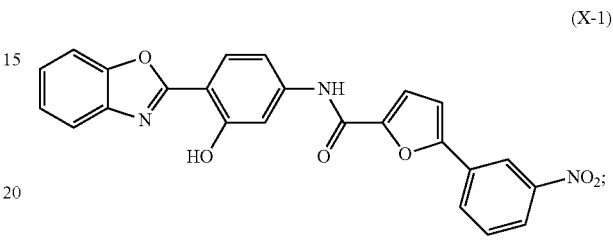

(X-1)

as a single stereoisomer or a mixture thereof; or a pharmaceutically acceptable salt thereof. Compound (X-1) is named herein as N-[4-(1,3-benzoxazol-2-yl)-3-hydroxyphenyl]-5-(3-nitrophenyl)-2-furamide.

In another embodiment, the hepsin inhibitor utilized in the methods of the invention comprises a compound of formula (XI), as set forth above in the Summary of the Invention:

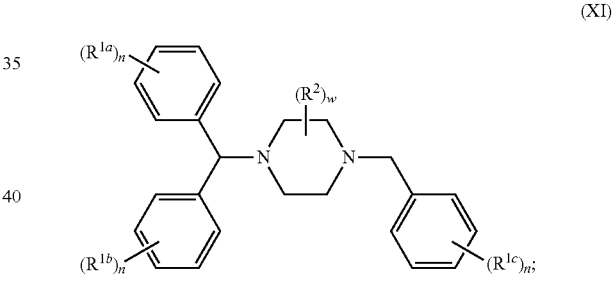

(XI)

wherein:
each n is 1, 2, 3, 4 or 5;
w is 1, 2, 3, 4, 5, 6, 7 or 8;
each $R^{1a}$, $R^{1b}$ and $R^{1c}$ is independently selected from the group consisting of hydrogen, alkyl, halo, haloalkyl, optionally substituted aryl, optionally substituted aralkyl, —$OR^7$, —CN, —$C(O)R^7$, —$C(O)OR^7$, —$C(O)N(R^7)R^8$, —$NO_2$, —$N(R^7)R^8$, —$N(R^7)C(O)R^8$, and —$N(R^7)C(O)OR^8$;
each $R^2$ is independently selected from the group consisting of hydrogen, alkyl, halo, haloalkyl, optionally substituted aryl and optionally substituted aralkyl; and
each $R^7$ and $R^8$ is independently selected from the group consisting of hydrogen, alkyl, optionally substituted aryl and optionally substituted aralkyl;
as a single stereoisomer or a mixture thereof;
or a pharmaceutically acceptable salt thereof.

In another embodiment of the invention, the hepsin inhibitor utilized in the methods of the invention comprises a compound of formula (XI), as set forth above, wherein:
each n is 1;
w is 1 or 2;

$R^{1a}$, $R^{1b}$ and $R^{ic}$ are each independently selected from the group consisting of hydrogen, alkyl and halo; and each $R^2$ is independently selected from the group consisting of hydrogen and alkyl.

In another embodiment of the invention, the hepsin inhibitor utilized in the methods of the invention comprises a compound of formula (XI) having the following formula (XI-1):

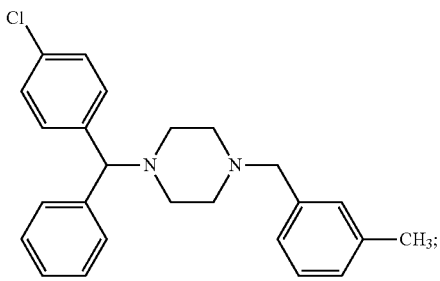
(XI-1)

as a single stereoisomer or a mixture thereof; or a pharmaceutically acceptable salt thereof. Compound (XI-1) is named herein as 1-[(4-chlorophenyl)(phenyl)methyl]-4-(3-methylbenzyl)piperazine.

In another embodiment, the hepsin inhibitor utilized in the methods of the invention comprises a compound of formula (XII), as set forth above in the Summary of the Invention:

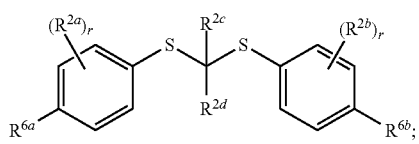
(XII)

wherein:
each r is 1, 2, 3 or 4;
each $R^{2a}$ and $R^{2b}$ is independently selected from the group consisting of hydrogen, alkyl, halo, haloalkyl, optionally substituted aryl and optionally substituted aralkyl;
$R^{2c}$ and $R^{2d}$ are each independently selected from the group consisting of hydrogen, alkyl, halo, haloalkyl, optionally substituted aryl and optionally substituted aralkyl;
$R^{6a}$ and $R^{6b}$ are each independently selected from the group consisting of hydrogen and —$OR^7$; and
$R^7$ is selected from the group consisting of hydrogen, alkyl, optionally substituted aryl and optionally substituted aralkyl;
as a single stereoisomer or a mixture thereof;
or a pharmaceutically acceptable salt thereof.

In another embodiment of the invention, the hepsin inhibitor utilized in the methods of the invention comprises a compound of formula (XII), as set forth above, wherein:
each r is 1 or 2;
each $R^{2a}$ and $R^{2b}$ is independently selected from the group consisting of hydrogen and alkyl;
$R^{2c}$ and $R^{2d}$ are each independently selected from the group consisting of hydrogen and alkyl;
$R^{6a}$ and $R^{6b}$ are each —$OR^7$; and
$R^7$ is selected from the group consisting of hydrogen and alkyl.

In another embodiment, the hepsin inhibitor utilized in the methods of the invention comprises a compound of formula (XII) having the following formula (XII-1):

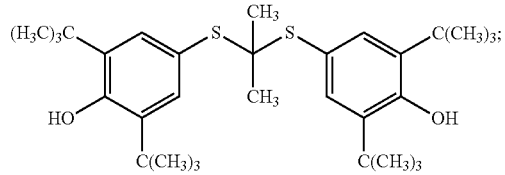
(XII-1)

as a single stereoisomer or a mixture thereof; or a pharmaceutically acceptable salt thereof. Compound (XII-1) is named herein as 4,4'-[propane-2,2-diylbis(sulfanediyl)]bis (2,6-di-tert-butylphenol).

In another embodiment, the hepsin inhibitor utilized in the methods of the invention comprises a compound of formula (XIII), as set forth above in the Summary of the Invention:

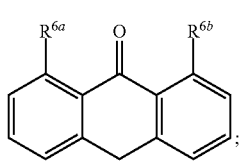
(XIII)

wherein:
$R^{6a}$ and $R^{6b}$ are each —$OR^7$; and
$R^7$ is selected from the group consisting of hydrogen, alkyl, optionally substituted aryl and optionally substituted aralkyl; and
as a single stereoisomer or a mixture thereof;
or a pharmaceutically acceptable salt thereof.

In another embodiment of the invention, the hepsin inhibitor utilized in the methods of the invention comprises a compound of formula (XIII), as set forth above, wherein:
$R^{6a}$ and $R^{6b}$ are each —$OR^7$; and
$R^7$ is selected from the group consisting of hydrogen and alkyl.

In another embodiment of the invention, the hepsin inhibitor utilized in the methods of the invention comprises a compound of formula (XIII) having the following formula (XIII-1):

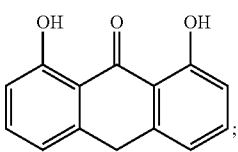
(XIII-1)

as a single stereoisomer or a mixture thereof; or a pharmaceutically acceptable salt thereof. Compound (XIII-1) is named herein as 1,8-dihydroxyanthracen-9(10H)-one.

In another embodiment, the hepsin inhibitor utilized in the methods of the invention comprises a compound of formula (XIV), as set forth above in the Summary of the Invention:

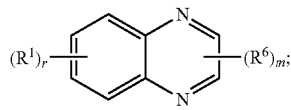

wherein:
m is 1 or 2;
r is 1, 2, 3 or 4;
each $R^1$ is independently selected from the group consisting of hydrogen, alkyl, halo, haloalkyl, optionally substituted aryl, optionally substituted aralkyl, $-OR^7$, $-CN$, $-C(O)R^7$, $-C(O)OR^7$, $-C(O)N(R^7)R^8$, $-NO_2$, $-N(R^7)R^8$, $-N(R^7)C(O)R^8$, and $-N(R^7)C(O)OR^8$;
each $R^6$ is independently selected from the group consisting of hydrogen and $-OR^7$; and
each $R^7$ and $R^8$ is independently selected from the group consisting of hydrogen, alkyl, optionally substituted aryl and optionally substituted aralkyl;
as a single stereoisomer or a mixture thereof;
or a pharmaceutically acceptable salt thereof.

In another embodiment of the invention, the hepsin inhibitor utilized in the methods of the invention comprises a compound of formula (XIV), as set forth above, wherein:
m is 2;
r is 2;
each $R^1$ is independently selected from the group consisting of halo and haloalkyl;
each $R^6$ is independently selected from the group consisting of hydrogen and $-OR^7$; and
each $R^7$ is independently selected from the group consisting of hydrogen and alkyl.

In another embodiment of the invention, the hepsin inhibitor utilized in the methods of the invention comprises a compound of formula (XIV) having the following formula (XIV-1):

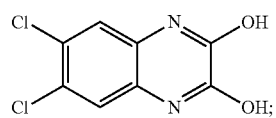

as a single stereoisomer or a mixture thereof; or a pharmaceutically acceptable salt thereof. Compound (XIV-1) is named herein as 2,3-dihydroxy-6,7-dichloroquinoxaline.

In another embodiment, the hepsin inhibitor utilized in the methods of the invention comprises a compound selected from the group consisting of:
1-(3-nitrophenyl)-1H-pyrrole-2,5-dione;
N-(3-chlorophenyl)-N'-{5-[(3,4-dimethylphenoxy)methyl]-1,3,4-thiadiazol-2-yl}urea;
N-[5-(4-bromophenyl)-1,3,4-thiadiazol-2-yl]-N'-(3,4-dichlorophenyl)urea;
1-(3-bromophenyl)-5-(1H-indol-3-yl)methylene)-2,4,6(1H,3H,5H)pyrimidinetrione;
2-(3-methylphenyl)-2,3-dihydro-1H-perimidine;
4-(4-nitrophenyl)-6-(trifluoromethyl)-3a,4,5,9b-tetrahydro-3H-cyclopenta[c]quinoline;
8-chloro-4-(3-nitrophenyl)-3a,4,5,9b-tetrahydro-3H-cyclopenta[c]quinoline;
6,6'-methylenebis[2-(3-fluorophenyl)-4H-3,1-benzooxazin-4-one];
3-(4-methyl-1,3-thiazol-2-yl)-7-[(pentafluorobenzyl)oxy]-2H-chromen-2-one;
N-(4-bromo-7,7-dimethyl-9-oxo-6,7,8,9-tetrahydrodibenzo[b,d]furan-2-yl)benzenesulfonamide;
2-{3-[2-(3-methoxyphenoxy)ethoxy]benzylidene}[1,3]thiazolo[3,2-a]benzimidazol-3(2H)-one;
N-[4-(1,3-benzoxazol-2-yl)-3-hydroxyphenyl]-5-(3-nitrophenyl)-2-furamide;
1-[(4-chlorophenyl)(phenyl)methyl]-4-(3-methylbenzyl)piperazine;
4,4'-[propane-2,2-diylbis(sulfanediyl)]bis(2,6-di-tert-butylphenol);
1,8-dihydroxyanthracen-9(10H)-one; and
2,3-dihydroxy-6,7-dichloroquinoxaline.

Of the various embodiments of the compounds of formulae (I)-(XIV), as set forth above, it is understood that various embodiments of these formulae are not specifically described herein and that such embodiments are considered to be within the scope of the invention.

Utility and Testing of the Invention

As also noted above, certain presently disclosed embodiments are directed to a method for preventing or attenuating cancer progression or blocking metastasis in a subject known to have, or suspected of being at risk for having, a cancer characterized by hepsin overexpression, such as prostate cancer, ovarian carcinoma, endometrial cancer or renal cell carcinoma. Certain illustrative examples are described herein with reference to prostate cancer as a preferred embodiment, but the invention is not intended to be so limited and may also find uses in the treatment of other cancers that are characterized by hepsin overexpression.

The presence of cancer or of a malignant condition in a subject refers to the presence of dysplastic, cancerous and/or transformed cells in the subject, including, for example neoplastic, tumor, non-contact inhibited or oncogenically transformed cells, or the like (e.g., prostate cancer or endometrial cancer or ovarian cancer or carcinomas such as adenocarcinoma, renal cell carcinoma, squamous cell carcinoma, small cell carcinoma, oat cell carcinoma, etc., sarcomas such as chondrosarcoma, osteosarcoma, etc., melanoma) which are known to the art and for which criteria for diagnosis and classification are established, as are signs and symptoms and/or risk factors according to which an individual may be identified as having, or as suspected of being at risk for having (or progressing to) a particular type of cancer or malignant condition. (e.g., Roulston, J. E. and Bartlett, J. M. S. (Eds.), Molecular Diagnosis of Cancer: Methods and Protocols (2$^{nd}$ Ed.), 2004, Humana Press, Totowa, N.J.; Hayat, M. A. (Ed.), Cancer Imaging, 2007, Academic Press, NY; Skarin, Atlas of Diagnostic Oncology, 2002, Mosby/Elsevier, Philadelphia, Pa.; Nakamura, R. M. et al., Cancer Diagnostics, 2004, Humana Press, Totowa, N.J.; etc.) These and related criteria are thus known and may further include determination of cancer progression and of metastasis or metastatic disease, i.e., the spread of one or a plurality of cancer cells from an initial or primary tumor site in a tissue or organ, to one or more distinct secondary sites where tumor cells lodge and proliferate to form secondary tumors having deleterious clinical consequences for the subject.

In preferred embodiments contemplated by the present invention, for example, such cancer cells are neoplastically transformed epithelial cells such as carcinoma cells. Certain particularly preferred embodiments contemplate application of the compositions and methods described herein for the treatment of a cancer that is characterized by cancer cells in which hepsin overexpression is present.

Prostate cancers may be classified according to recognized stages in the progression of disease, e.g., as prostatic intraepithelial neoplasia (PIN), prostate-confined non-invasive low-grade cancer, prostate-confined invasive cancer, metastatic prostate cancer, etc., as described in, e.g., Vasioukhin, 2004 *Cell Cycle* 3:1394. Prostate cancers may also be graded according to the Tumor-Node-Metastasis (TNM) staging system (e.g., Chang et al., 2008 *CA Cancer J Clin* 58:54-59).

As is presently practiced in the art, early stages of prostate cancer such as prostatic intraepithelial neoplasia (PIN) and/or prostate-confined non-invasive low-grade cancer, represent early steps in the progression of disease wherein current clinical practices include so-called "watchful waiting" as a management strategy. In "watchful waiting", periodic assessment of disease progression is made but no major invasive procedures (e.g., surgery) are undertaken so long as the cancer remains confined to the prostatic epithelium without disrupting the underlying basement membrane.

Because many of the sequelae of surgical intervention to remove prostate tissue containing invasive and/or metastatic prostate cancer cells include undesirable but frequently unavoidable side-effects that negatively impact the patient's quality of life (e.g., chronic pain, discomfort, incontinence, loss of sexual function), it may be desirable according to certain herein disclosed embodiments to prevent or attenuate cancer progression or to block metastasis, by treatments that prevent progression of prostate cancer to invasive and/or metastatic stages, i.e., to maintain the "watchful waiting" status. Accordingly and without wishing to be bound by theory, certain herein disclosed embodiments relate to maintenance of cancer in a subject at such, a pre-invasive, pre-metastatic stage, by administering one or more of the herein disclosed hepsin inhibitor compounds in a manner that interferes with cancer progression and thereby precludes the need for surgery.

Hepsin overexpression in prostate cancer cells, and implication of hepsin in cancer progression and metstasis (including a possible role in the disruption of basement membranes underlying prostatic epithelia, leading to tumor invasion of the basement membrane and progressing to metastatic disease), have been reported (Klezovitch et al., 2004 *Cancer Cell* 6:185; Srikantan et al., 2002 *Cancer Res.* 62:6812). The inability of hepsin-overexpressing metastatic prostate cancer cell lines to invade laminin matrigels in vitro, however (Srinkantan et al., 2002), suggests unappreciated complexity of hepsin's role in metastatic mechanisms. Moreover, prior to the present application, no specific hepsin inhibitor compounds such as the ones described herein had been identified for use according to certain present embodiments.

Similar staging paradigms are established for ovarian cancer progression, for instance, that of the International Federation of Gynecology and Obstetrics (FIGO) according to which, generally, epithelial ovarian cancer stages I (occurrence of cancer cells limited to intraovarian sites), II (intraovarian plus pelvic cancer cells), III (occurrence of cancer cells limited to intraovarian, pelvic, and abdominal or proximate regional sites), and IV (as III plus involvement of other (distal) organs as cancer sites), and recurrent ovarian cancer, have been classified (TNM Classification of Malignant Tumours, Sixth Edition, UICC, 2002). Endometrial cancer progression has also been classified by stages in like fashion (see, e.g., NIH/NCI PDQ® cancer information database, National Cancer Institute, Frederick, Md.): stage I (confined to occurrence of cancer cells within uterus only), II (cancer detected in uterus and cervix), III (cancer cells beyond uterus and cervix but restricted to pelvic region), and IV (cancer detected beyond pelvis, including bladder, bowel, abdominal or groin lymph nodes or beyond).

Renal cell carcinoma progression has also been defined according to the TNM staging system (American Joint Committee on Cancer (AJCC), TNM Classification of Malignant Tumours, Sixth Edition, UICC, 2002). Hence, stage I renal cell carcinoma involves intrarenal tumors of no more than seven centimetres in diameter, stage II involves intrarenal tumors in excess of seven centimetres, stage III involves confinement of tumors to renal (Gerota's) fascia and up to one lymph node in the vicinity of the affected kidney, and in stage IV renal carcinoma cancer cells have invaded tissues beyond the renal fascia as evidenced by cancer in more than one lymph node in the vicinity of the affected kidney, or in at least one distal site.

As described herein, there are identified for the first time as specific hepsin inhibitors 16 small molecule compounds that can be structurally assigned to one of 14 generic structures. Based on the identification herein of these specific inhibitors and of the corresponding generic structures for which some or all of these inhibitors may have value as lead compounds, it is contemplated that certain embodiments of the present invention will be of major value in high throughput screening; i.e., in automated testing or screening of a large number of additional candidate hepsin inhibitors, for example, in screening synthetic or natural product libraries for additional structurally related, active compounds.

Typically, and in certain preferred embodiments such as for high throughput drug screening, candidate agents (e.g., candidate hepsin inhibitors belonging to a hepsin inhibitor structural genus as herein disclosed) are provided as "libraries" or collections of compounds, compositions or molecules. Such molecules typically include compounds known in the art as "small molecules" and having molecular weights less than $10^5$ daltons, preferably less than $10^4$ daltons and still more preferably less than $10^3$ daltons.

Candidate agents further may be provided as members of a combinatorial library, which preferably includes synthetic agents prepared according to a plurality of predetermined chemical reactions performed in a plurality of reaction vessels. For example, various starting compounds may be prepared employing one or more of solid-phase synthesis, recorded random mix methodologies and recorded reaction split techniques that permit a given constituent to traceably undergo a plurality of permutations and/or combinations of reaction conditions. The resulting products comprise a library of structurally related compounds that can be screened followed by iterative selection and synthesis procedures, such as a synthetic combinatorial library that may include small molecules as provided herein (see e.g., PCT/US94/08542, EP 0774464, U.S. Pat. No. 5,798,035, U.S. Pat. No. 5,789,172, U.S. Pat. No. 5,751,629).

Accordingly in these and related embodiments there is provided a method of inhibiting hepsin proteolytic activity, comprising contacting a hepsin polypeptide and a hepsin inhibitor (e.g., a compound having a structure that is within one of the structures of formulae I-XIV as provided herein) under conditions and for a time sufficient for the hepsin inhibitor to interact specifically with the hepsin polypeptide. As described herein in the illustrative examples, such contacting may typically involve a method whereby the hepsin polypeptide and the hepsin inhibitor are afforded an opportunity physically to contact one another (e.g, by exposing, introducing, admixing, incubating or otherwise bringing into close and unhindered proximity), and these and related embodiments further contemplate determining inhibition of the proteolytic activity of the hepsin polypeptide, for example, by detecting a level of enzymatic cleavage by the hepsin polypeptide of a detectable serine protease substrate (e.g., a chromogenic substrate) in the absence of the hepsin inhibitor that differs (with statistical significance) from the level of enzymatic cleavage by the hepsin polypeptide of the detectable serine protease substrate (e.g., a chromogenic substrate) in the presence of the hepsin inhibitor.

Operable conditions, including solution conditions, temperature, and incubation times, for determining serine protease activity such as the ability of a hepsin polypeptide to cleave a serine protease substrate as provided herein (e.g., pyroGlu-Pro-Arg-pNA), are known to persons familiar with the art (e.g., Somoza et al., 2003 Structure 11:1123) and/or can be readily identified using only routine experimentation, based on existing knowledge in enzymology generally, and specifically with regard to serine proteases. These and related embodiments may afford identification from amongst the presently disclosed hepsin inhibitors of those having particularly desirable properties, depending on intended uses such as, e.g., formulations for particular routes of administration or having one or more hepsin inhibitors of particular efficacies, potencies and/or physicochemical or pharmacokinetic properties. As also described herein, the compounds identified herein as hepsin inhibitors exhibit significant selectivity toward hepsin as contrasted with inhibitory activity against other serine proteases such as trypsin and thrombin (e.g., Table 1), such that any specific one of the present hepsin inhibitors should have an $IC_{50}$ value when tested against hepsin that is lower (i.e., in a statistically significant manner) than the $IC_{50}$ value when tested against trypsin or thrombin. Preferred are hepsin inhibitors that exhibit at least 10-fold, 20-fold, 30-fold, 40-fold, 50-fold, 60-fold, 70-fold, 75-fold, 80-fold or greater selectivity for hepsin relative to either or both of trypsin and thrombin.

The mammalian cell surface type-II transmembrane serine protease hepsin is a well known polypeptide. The human hepsin polypeptide, for example, (e.g., Genbank Acc. Nos. NP_892028; NP_002142; BC025716; SEQ ID NOS:1-3) comprises an extracellular region (e.g., from amino acid positions serine-46 to leucine-417 in Genbank BC025716 and set forth in SEQ ID NO:4) that includes the scavenger receptor cysteine-rich (SRCR) domain and hepsin catalytic domain (e.g., amino acid positions 163 to 400, SEQ ID NO:5) having serine protease activity (Somoza et al., 2003 Structure 11:1123). As further examples, at least two highly similar murine hepsin polypeptide sequences have been identified (Genbank Acc. Nos. AAI38810, SEQ ID NO:6; and AAB84221, SEQ ID NO:9). The amino acid sequence set forth in SEQ ID NO:9, for instance, is about 88% identical to the human hepsin sequence (SEQ ID NO:1, 2 or 3) and has a hepsin catalytic domain (amino acids 162-400, SEQ ID NO:11) that is about 91% identical to the corresponding human hepsin catalytic domain (SEQ ID NO:5). The extracellular region of SEQ ID NO:9 comprises amino acids serine-45 to proline 416 and has the sequence set forth in SEQ ID NO:10. Similarly, the corresponding extracellular region of SEQ ID NO:6 comprises amino acids serine-65 to proline-435 and has the sequence set forth in SEQ ID NO:7, and the hepsin catalytic domain (amino acids 182-419) of SEQ ID NO:6 has the sequence set forth in SEQ ID NO:8.

Criteria for determining hepsin protease activity are well established and include specific cleavage by the enzyme of any of a number of serine protease substrate peptides having defined sequences, but not of peptides having irrelevant sequences. A suitable substrate for hepsin protease activity may therefore be, for instance, the chromogenic serine protease substrate L-pyroglutamyl-L-prolyl-L-arginine-p-nitroaniline (pyroGlu-Pro-Arg-pNA), available as L-pyroglutamyl-L-prolyl-L-arginine-p-nitroaniline hydrochloride (Diapharma Inc., West Chester, Ohio, Cat. No. S-2366).

A hepsin polypeptide for use in certain embodiments contemplated herein may therefore comprise the amino acid sequence set forth in any one of Genbank Acc. Nos. NP_892028, NP_002142, and BC025716 [SEQ ID NOS:1-3], AAB4221 and AAI38810 [SEQ ID NOS:9 and 6, respectively] and, and may in certain other embodiments comprise a hepsin polypeptide variant comprising a polypeptide that is at least 85%, 90%, 95%, 96%, 97%, 98% or 99% identical to such polypeptides and that is capable of specific enzymatic cleavage of a serine protease substrate such as the chromogenic serine protease substrate L-pyroglutamyl-L-prolyl-L-arginine-p-nitroaniline (pyrGlu-Pro-Arg-pNA). In certain other embodiments a hepsin polypeptide may comprise a polypeptide that comprises a hepsin catalytic domain or a functional fragment thereof or variant thereof, the hepsin catalytic domain or functional fragment thereof or variant thereof comprising an amino acid sequence that is at least 80%, 85%, 90% or 95% identical to the amino acid sequence set forth in SEQ ID NO:5 (amino acids 163-400 of BC025716 (SEQ ID NO:3)), SEQ ID NO:8 (amino acids 182-419 of AAI38810 (SEQ ID NO:6)) or SEQ ID NO:11 (amino acids 162-400 of AAB4221 (SEQ ID NO:9)) and that is capable of specific enzymatic cleavage of a chromogenic serine protease substrate that comprises pyroGlu-Pro-Arg-pNA.

Polypeptide variants of a hepsin polypeptide or of a hepsin catalytic domain or a functional fragment thereof may contain one or more amino acid substitutions, additions, deletions, and/or insertions relative to a native hepsin polypeptide sequence such as the amino acid sequence set forth in any one of Genbank Acc. Nos. NP_892028, NP_002142, and BC025716 [SEQ ID NOS:1-3], AAB4221 and AAI38810 (SEQ ID NOS:9 and 6) (e.g. wildtype, or a predominant or naturally occurring allelic form). Variants preferably exhibit at least about 75%, 78%, 80%, 85%, 87%, 88% or 89% identity and more preferably at least about 90%, 92%, 95%, 96%, 97%, 98%, or 99% identity to a portion of a native hepsin polypeptide sequence. The percent identity may be readily determined by comparing sequences of the polypeptide variants with the corresponding portion of a full-length polypeptide. Some techniques for sequence comparison include using computer algorithms well known to those having ordinary skill in the art, such as Align or the BLAST algorithm (Altschul, J. Mol. Biol. 219:555-565, 1991; Henikoff and Henikoff, PNAS USA 89:10915-10919, 1992), which is available at the NCBI website (see [online] Internet: <URL: http://www/ncbi.nlm.nih.gov/cgi-bin/BLAST). Default parameters may be used.

Furthermore, computer algorithms are available in the art that enable the skilled artisan to predict the three-dimensional structure of a protein or peptide, in order to ascertain functional variants of a particular polypeptide. For instance, variants can be identified wherein all or a portion of the three-dimensional structure is not substantially altered by one or more modification, substitution, addition, deletion and/or insertion. (See, for example, Bradley et al., Science 309: 1868-1871 (2005); Schueler-Furman et al., Science 310:638 (2005); Dietz et al., Proc. Nat. Acad. Sci. USA 103:1244 (2006); Dodson et al., Nature 450:176 (2007); Qian et al., Nature 450:259 (2007)). In this way, one of skill in the art can readily determine whether a particular hepsin polypeptide variant or a hepsin catalytic domain or a functional fragment thereof is capable of specific enzymatic cleavage of a serine protease substrate such as pyroGlu-Pro-Arg-pNA.

Methodologies for the design, production and testing of hepsin polypeptides and polypeptide variants and of hepsin catalytic domains and functional fragments thereof as provided herein are all available by minor modification to existing knowledge in the art, for example, using conventional methods of virology, immunology, microbiology, molecular biology and recombinant DNA techniques, which are explained fully in the literature. See, e.g., Sambrook, et al. *Molecular Cloning: A Laboratory Manual* (2nd Edition, 1989); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984).

According to these and related methodologies and based on the disclosure herein, there are also contemplated certain embodiments wherein the hepsin polypeptide as described herein may comprise a cell surface hepsin polypeptide. Those skilled in the art will be familiar with criteria for determining whether a particular polypeptide, such as a hepsin polypeptide, is present on a cell surface, including detection via radiological imaging or fluorescence magnetic resonance imaging or immunofluorescence or immunohistologic imaging or other immunologic detection, or by biochemical (including enzymological) or histochemical or other cell surface localization detection means. The cell surface hepsin polypeptide may be present on a cell surface naturally or as a result of genetic engineering, or in response to another artificial stimulus.

The cell surface hepsin polypeptide may be present on a cell in vivo according to certain embodiments, and according to certain other embodiments the cell surface hepsin polypeptide may be present on a cell ex vivo or in vitro. In certain preferred embodiments, the cell surface hepsin polypeptide is present on the surface of a cell that is selected from a prostate cancer cell, an ovarian carcinoma cell, an endometrial cancer cell and a renal carcinoma cell. In certain related preferred embodiments, the cell surface hepsin polypeptide is present on the surface of a prostate cancer cell of a subject having prostatic intraepithelial neoplasia or prostate-confined non-invasive low-grade cancer. As described herein, such a subject may be a member of the "watchful waiting" cohort for which these and related embodiments may be particularly useful. In certain of these and other embodiments described herein as may relate to a method for inhibiting hepsin proteolytic activity on a cell surface, it will be appreciated that therapeutic and/or diagnostic benefits to the subject may be obtained. For example, by way of illustration and not limitation, it is contemplated that by the practice of these and related embodiments, cancer progression may be prevented or attenuated, or metastasis blocked, as described herein.

There is thus provided a method of inhibiting hepsin proteolytic activity on a cell surface, comprising contacting a cell that comprises a cell surface hepsin polypeptide and a hepsin inhibitor (e.g., a compound having a structure that is within one of the structures of formulae I-XIV as provided herein) under conditions and for a time sufficient for the hepsin inhibitor to interact specifically with the hepsin polypeptide, and thereby inhibiting hepsin proteolytic activity on the cell surface. As described herein in the illustrative examples, such contacting may typically involve a method whereby the hepsin polypeptide and the hepsin inhibitor are afforded an opportunity physically to contact one another (e.g, by exposing, introducing, admixing, incubating or otherwise bringing into close and unhindered proximity), and these and related embodiments also contemplate administration of the inhibitor to the cell in vivo according to any administrative route such as those described herein.

Pharmaceutical Compositions of the Invention and Administration

The present invention also relates in certain embodiments to pharmaceutical compositions containing the compounds of the invention disclosed herein. In one embodiment, the present invention relates to a pharmaceutical composition comprising compounds of the invention in a pharmaceutically acceptable excipient, carrier or diluent and in an amount effective to prevent or attenuate cancer progression or block metastasis, when administered to an animal, preferably a mammal, most preferably a human.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, intranasal, intraperitoneal, intravenous, intraarterial, transdermal, sublingual, subcutaneous, intramuscular, rectal, transbuccal, intranasal, liposomal, via inhalation, intraoccular, via local delivery, subcutaneous, intraadiposal, intraarticularly or intrathecally. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *The Science and Practice of Pharmacy*, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 Kg mammal) from about 0.001 mg/Kg (i.e., 0.07 mg) to about 100 mg/Kg (i.e., 7.0 g); preferably a therapeutically effective dose is (for a 70 Kg mammal) from about 0.01 mg/Kg (i.e., 0.7 mg) to about 50 mg/Kg (i.e., 3.5 g); more preferably a therapeutically effective dose is (for a 70 Kg mammal) from about 1 mg/kg (i.e., 70 mg) to about 25 mg/Kg (i.e., 1.75 g).

The ranges of effective doses provided herein are not intended to be limiting and represent preferred dose ranges. However, the most preferred dosage will be tailored to the individual subject, as is understood and determinable by one skilled in the relevant arts. (see, e.g., Berkowet al., eds., The Merck Manual, $16^{th}$ edition, Merck and Co., Rahway, N.J., 1992; Goodman et al., eds., Goodman and Gilman's The Pharmacological Basis of Therapeutics, $10^{th}$ edition, Pergamon Press, Inc., Elmsford, N.Y., (2001); Avery's Drug Treatment: Principles and Practice of Clinical Pharmacology and Therapeutics, 3rd edition, ADIS Press, LTD., Williams and Wilkins, Baltimore, Md. (1987), Ebadi, Pharmacology, Little, Brown and Co., Boston, (1985); Osolci al., eds., Remington's Pharmaceutical Sciences, $18^{th}$ edition, Mack Publishing Co., Easton, Pa. (1990); Katzung, Basic and Clinical Pharmacology, Appleton and Lange, Norwalk, Conn. (1992)).

The total dose required for each treatment can be administered by multiple doses or in a single dose over the course of the day, if desired. Generally, treatment is initiated with smaller dosages, which are less than the optimum dose of the compound. Thereafter, the dosage is increased by small increments until the optimum effect under the circumstances is reached. The diagnostic pharmaceutical compound or composition can be administered alone or in conjunction with other diagnostics and/or pharmaceuticals directed to the pathology, or directed to other symptoms of the pathology. The recipients of administration of compounds and/or compositions of the invention can be any vertebrate animal, such as mammals. Among mammals, the preferred recipients are mammals of the Orders Primate (including humans, apes and monkeys), Arteriodactyla (including horses, goats, cows, sheep, pigs), Rodenta (including mice, rats, rabbits, and hamsters), and Carnivora (including cats, and dogs). Among birds, the preferred recipients are turkeys, chickens and other members of the same order. The most preferred recipients are humans.

For topical applications, it is preferred to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The compositions of the invention can be formulated so as to provide quick, sustained or delayed release of the active ingredient after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al., *Regional Anesthesia* 22 (6): 543-551 (1997), all of which are incorporated herein by reference.

The compositions of the invention can also be delivered through intra-nasal drug delivery systems for local, systemic, and nose-to-brain medical therapies. Controlled Particle Dispersion (CPD)™ technology, traditional nasal spray bottles, inhalers or nebulizers are known by those skilled in the art to provide effective local and systemic delivery of drugs by targeting the olfactory region and paranasal sinuses.

The invention also relates to an intravaginal shell or core drug delivery device suitable for administration to the human or animal female. The device may be comprised of the active pharmaceutical ingredient in a polymer matrix, surrounded by a sheath, and capable of releasing the compound in a substantially zero order pattern on a daily basis similar to devises used to apply testosterone as described in PCT Published Patent No. WO 98/50016.

Current methods for ocular delivery include topical administration (eye drops), subconjunctival injections, periocular injections, intravitreal injections, surgical implants and iontophoresis (uses a small electrical current to transport ionized drugs into and through body tissues). Those skilled in the art would combine the best suited excipients with the compound for safe and effective intraoccular administration.

The most suitable route will depend on the nature and severity of the condition being treated. Those skilled in the art are also familiar with determining administration methods (e.g. oral, intravenous, inhalation, sub-cutaneous, rectal, etc.), dosage forms, suitable pharmaceutical excipients and other matters relevant to the delivery of the compounds to a subject in need thereof.

Unless the context requires otherwise, throughout the specification and claims which follow, the word "comprise" and variations thereof, such as, "comprises" and "comprising" are to be construed in an open, inclusive sense, that is as "including, but not limited to".

Reference throughout this specification to "one embodiment" or "an embodiment" or "an aspect" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Preparation of the Compounds Used in the Methods of the Invention

The compounds used in the methods of the invention can be prepared according to methods known to one skilled in the art or are commercially available, for example, from ChemBridge Corporation (San Diego, Calif.) or MicroSource Discovery Systems (Gaylordsville, Conn.). All the compounds used in the methods of the invention which exist in free base or acid form may be converted to their pharmaceutically acceptable salt by treatment with the appropriate inorganic or organic base or acid by methods known to one skilled in the art. Salts of the compounds may be converted to their free base or acid by standard techniques known to one skilled in the art.

The following Examples, which include assays that can be utilized to determine the efficacy of the compounds in the methods of the invention, are provided as a guide to assist in the practice of the invention, and are not intended as a limitation on the scope of the invention.

BIOLOGICAL EXAMPLE 1

Experimental Methods

A. Reagents. The DIVERSet™ and NINDS II compound libraries and reordered hit compounds from those libraries were purchased from Chembridge Corporation (San Diego, Calif.) and MicroSource Discovery Systems, Inc. (Gaylordsville, Conn.), respectively. The chromogenic peptide pyro-Glu-Pro-Arg-pNA (S-2366) was purchased through Diapharma Group, Inc. (West Chester, Ohio). Rabbit anti-human hepsin polyclonal antibody was purchased from Cayman Chemical (Ann Arbor, Mich., #100022) and goat-anti-rabbit Ig secondary antibody was purchased from Jackson ImmunoResearch (West Grove, Pa.). Molecular biology grade DMSO was purchased from Fluka (Sigma-Aldrich, St. Louis, Mo.). Trypsin was purchased from ICN (MP Biomedicals, Solon, Ohio, #103140). Thrombin was purchased from Sigma (St. Louis, Mo., T-3399).

B. Recombinant Hepsin Expression and Purification.

Recombinant expression and chromatographic purification of human hepsin was performed as described previously (Somoza et al., 2003 Structure 11:1123).

C. Compound Library Screening. The DIVERSet™ 10,000 compound and NINDS II 1040 compound libraries were diluted from 20 and 10 µM stock plates in DMSO (respectively) to 20 µM 10× solutions in 10% DMSO. Purified hepsin was incubated with 2 µM compounds in 30 mM Tris-HCl, 30 mM imidazole, 200 mM NaCl and 1% DMSO for 30 minutes at room temperature. Chromogenic peptide was added and the reactions allowed to proceed for 3 hours. Endpoint absorbance was measured using a VersaMax™ microplate reader (Molecular Devices Inc., Sunnyvale, Calif.), corrected for background and residual activity observed relative to solvent controls on each plate.

D. Hepsin, Trypsin and Thrombin Activity Assays. Titration of the chromogenic substrate pryoGlu-Pro-Arg-pNA was performed for each enzyme and the resulting substrate-velocity data fit with nonlinear regression using GraphPad Prism 4 software (GraphPad, La Jolla, Calif.) to calculate Vmax and Km. Enzyme assay concentration and observed Km: 0.4 nM hepsin, Km=170 µM, 0.4 nM trypsin, Km=78.6 µM, thrombin 188mU/mL, Km=106.2 µM. Inhibitor activity was determined by incubating the individual enzymes with increasing concentrations of compounds in the library screen buffer for 30 minutes at room temperature followed by addition of the substrate at the observed Km. The reactions were then followed using a kinetic microplate reader and the linear rates of increase in absorbance at 405 nm expressed as percent activity (100%×vi/vo). At least three independent experiments were performed for each enzyme. The $IC_{50}$ was calculated by fitting the data to a four-parameter non-linear regression using GraphPad Prism 4.

E. Cell Culture. LNCaP, HepG2 and HEK 293FT cells were purchased from ATCC (Manassas, Va.). The spontaneously transformed mouse prostate epithelial cell line MP-1 was established by passaging C57/B6 primary mouse prostate epithelial cells. Cell culture components and suppliers were as follows: DMEM, F12 and RPMI base medias (Invitrogen, Carlsbad, Calif.), hydrocortisone (Calbiochem/EMD, San Diego, Calif.), insulin, T3 and cholera toxin (Sigma, St. Louis, Mo.). Cells were incubated in a humidified (37° C., 5% $CO_2$) incubator and passaged at 80% confluence with trypsin/EDTA. Mouse prostate epithelial cells MP-1 were maintained in E-media containing: 3:1 DMEM/F12, 37 mM sodium bicarbonate, 0.42n/mL hydrocortisone, 0.89 ng/mL cholera toxin, 5.3 µg/mL insulin, 5.3 µg/mL transferrin, 2.1×10-11M T3, 16 pen/strep and L-glutamine with 15% FCS. LNCaP cells were maintained in RPMI supplemented with 10% FCS and pen/strep. HepG2 cells were maintained in DMEM supplemented with 10% FCS and pen/strep. 293FT cells were maintained in DMEM supplemented with 10% FCS, L-glutamine, non-essential amino-acids and pen/strep.

F. Cell Cytotoxicity Assay. The general cytotoxicity of the compounds was determined using the CellTiter-Glo™ Assay from Promega (Madison, Wis.). Mouse prostate epithelial, LNCaP and HepG2 cells were seeded in 96-well black culture plates at 2×104 cells per well and allowed to attach. Media was aspirated and compounds were administered at 20 µM in the appropriate media and media with compounds was changed at 24 and 48 hours. CellTiter-Glom' reagent was added to the cells and ATP-coupled luciferase activity recorded on a microplate luminometer.

G. Pericellular Serine Proteolytic Activity Assay. Plasmids containing cDNA encoding full-length wild-type murine hepsin (Genbank Acc. No. AAB84221, SEQ ID NO:9) (Vu et al., 1997 J. Biol. Chem. 272:31315; Wu et al., 1998 J. Clin. Invest 101:321; Kawamura et al., 1999 Eur. J. Bioch. 262: 755), or an active-site serine-to-alanine mutation at amino acid position 352 of SEQ ID NO:9 (catalytically inactive S352A mutant hepsin, SEQ ID NO:12), or the empty pLNCX2 vector, were transfected into HEK 293FT cells using a calcium phosphate protocol. After 3.5 hrs, transfection media was replaced with fresh media containing 20 µM or 50 µM of test compounds or solvent control (0.5% DMSO in media) and cells incubated overnight. Attached cell monolayers were then washed twice with PBS and once with assay buffer (5% $CO_2$ equilibrated phenol-red free DMEM with 1% BSA) to remove residual serum proteases/inhibitors. Cells were then incubated in assay buffer containing 20 or 50 µM compounds for 30 minutes at 37° C. Peptide substrate was then added to a final concentration of 369 µM (observed Km in this system) and the reactions allowed to proceed at 37° C. Samples were withdrawn at 20, 40 and 60 minutes, quenched into an equal volume of 7% acetic acid and absorbance at 405 nm measured with a microplate reader. Percent inhibition was calculated as residual activity relative to solvent control. Matched samples were used in parallel to determine toxicity of the test compounds to HEK 293FT cells in this system using the CellTiter-Glo™ assay.

H. Immunoblotting. Total protein lysates from transfected, compound treated HEK 293FT cells were separated on SDS-PAGE and transferred to Immobilon-P™ membrane (Millipore, Billerica, Mass.). The membrane was blocked overnight in TBST buffer containing: 5% non-fat milk, 2% normal goat serum in 50 mM Tris-HCl, pH 8.0, 100 mM NaCl, 0.1% Tween-20. The membrane was then incubated in 3% BSA in TBST with polyclonal anti-hepsin antibody (1:1000) for two hours at room temperature, washed 3×5 minutes with TBST and incubated for one hour in 0.1% BSA in TBST containing goat-anti-rabbit-HRP secondary antibody (1:2000), washed 3×5 minutes in TBST and developed with ECL (Pierce Chemicals, Rockford, Ill.). Protein loading was confirmed by stripping the membrane and reprobing with anti-β-actin antibodies. Expression levels were quantified by densitometry using ImageQuantTL™ (GE Healthcare Life Sciences, Piscataway, N.J.).

BIOLOGICAL EXAMPLE 2

Identification of Specific Hepsin Inhibitors

A. Expression and Purification of the Recombinant Extracellular Region of Hepsin.

In the human hepsin polypeptide (e.g., Genbank Acc. No. BC025716 [SEQ ID NO:3]) the extracellular region has been identified as residues Ser46 to Leu417 (SEQ ID NO:4) and contains the catalytic and scavenger receptor cysteine-rich (SRCR) domain. The yeast *P. pastoris* was stably transfected with the hepsin expression construct and the secreted 41 kD hepsin zymogen was purified from the media using several steps of affinity and ion exchange chromatography. During purification to homogeneity, the enzyme spontaneously activated as previously reported (Somoza et al., 2003 *Structure* 11:1123). Protein identity was confirmed by silver staining of SDS-PAGE separated samples and immunoblotting with anti-hepsin catalytic domain polyclonal antibodies (FIG. 1A). The purified hepsin was enzymatically active (FIG. 1B), cleaving the chromogenic serine protease substrate pyroGlu-Pro-Arg-pNA.

Figure 2:
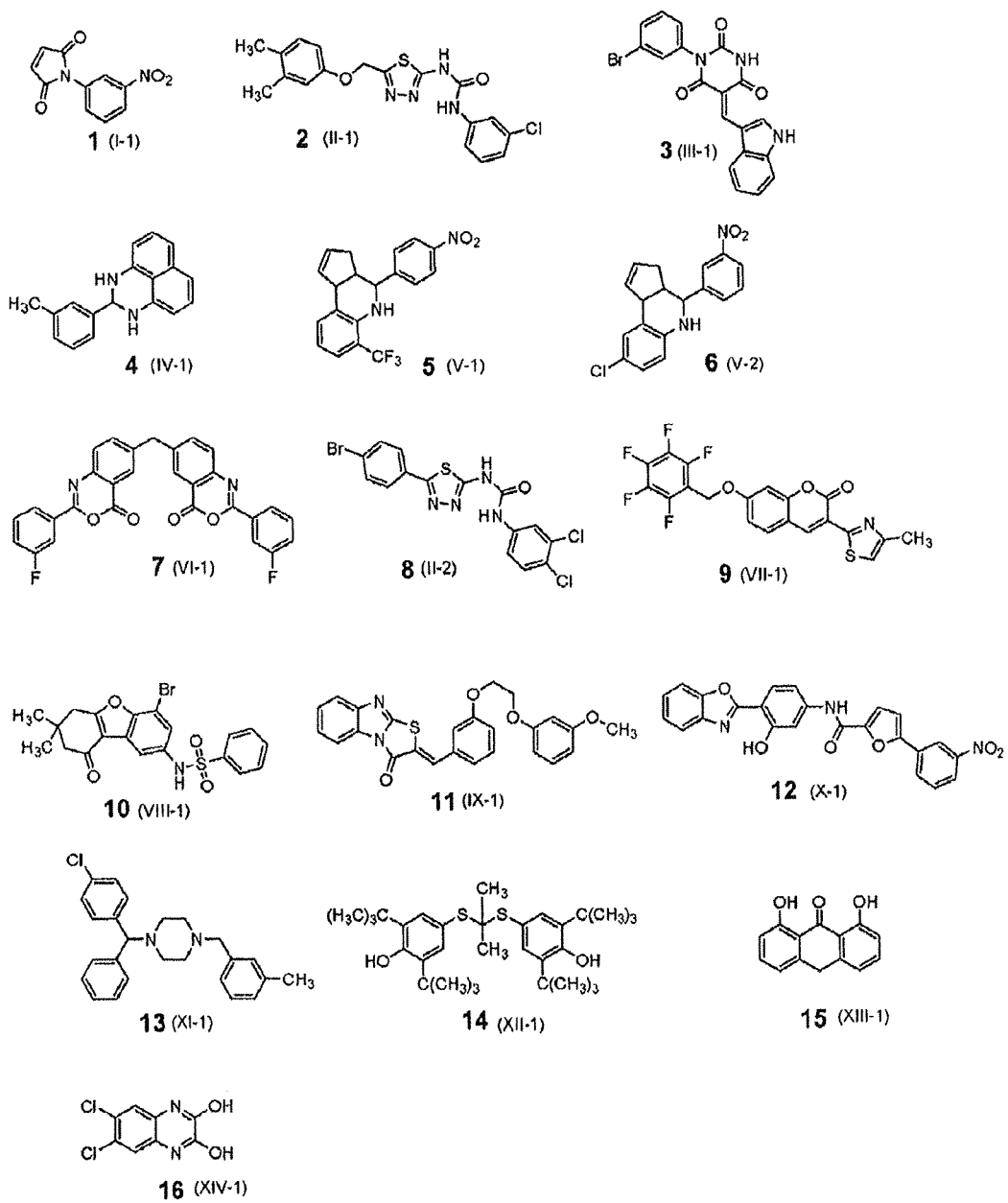
FIG. 2 shows chemical structures of identified hepsin inhibitors. Compounds 1-12 were identified from the ChemBridge DIVERSet™ library. Compounds 13-16 (meclizine, probucol, anthralin and 2,3-dihydroxy-6,7-dichloroquinoxaline) were identified from the NINDS II library of known drugs and bioactives.
Figure 3A:
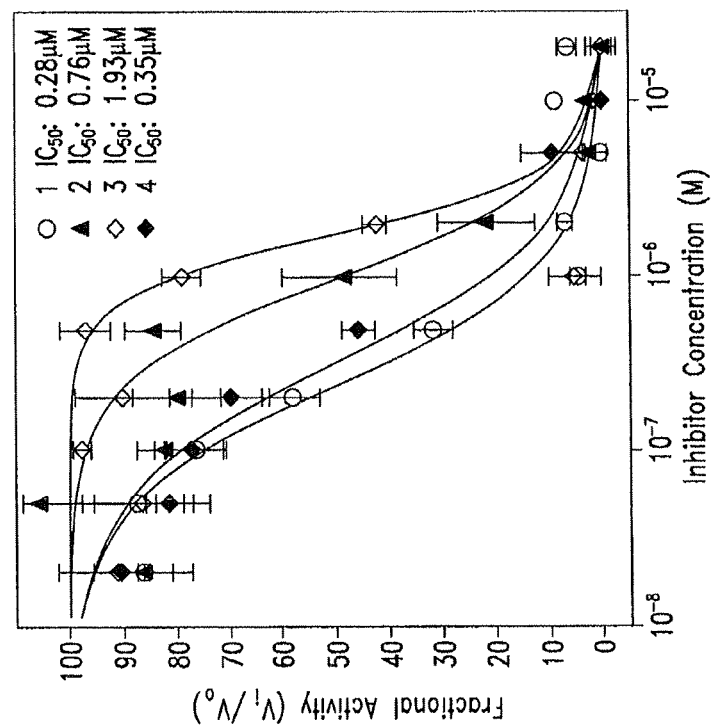
(FIG. 3A) Compounds 1-4.
Figure 3B:
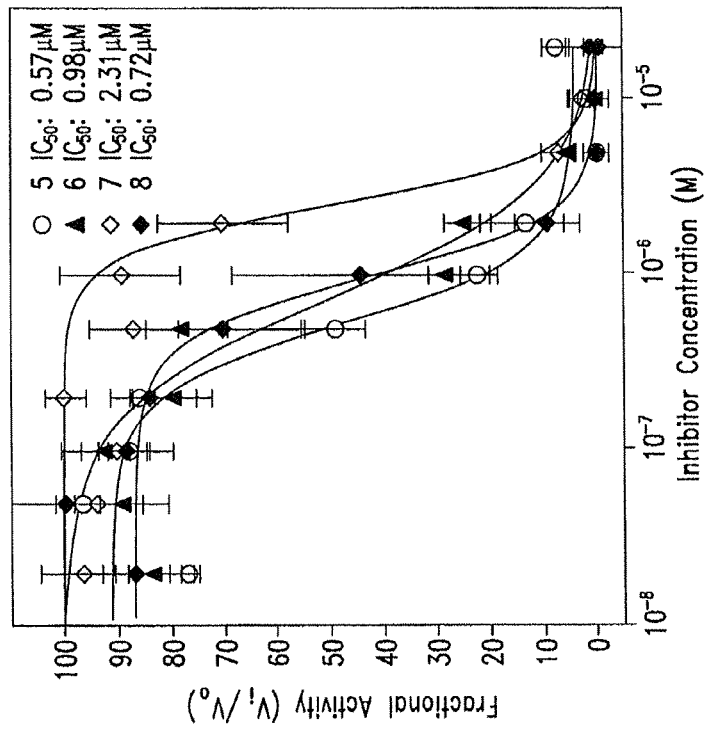
(FIG. 3B) Compounds 5-8.
Figures 3C, 3D:
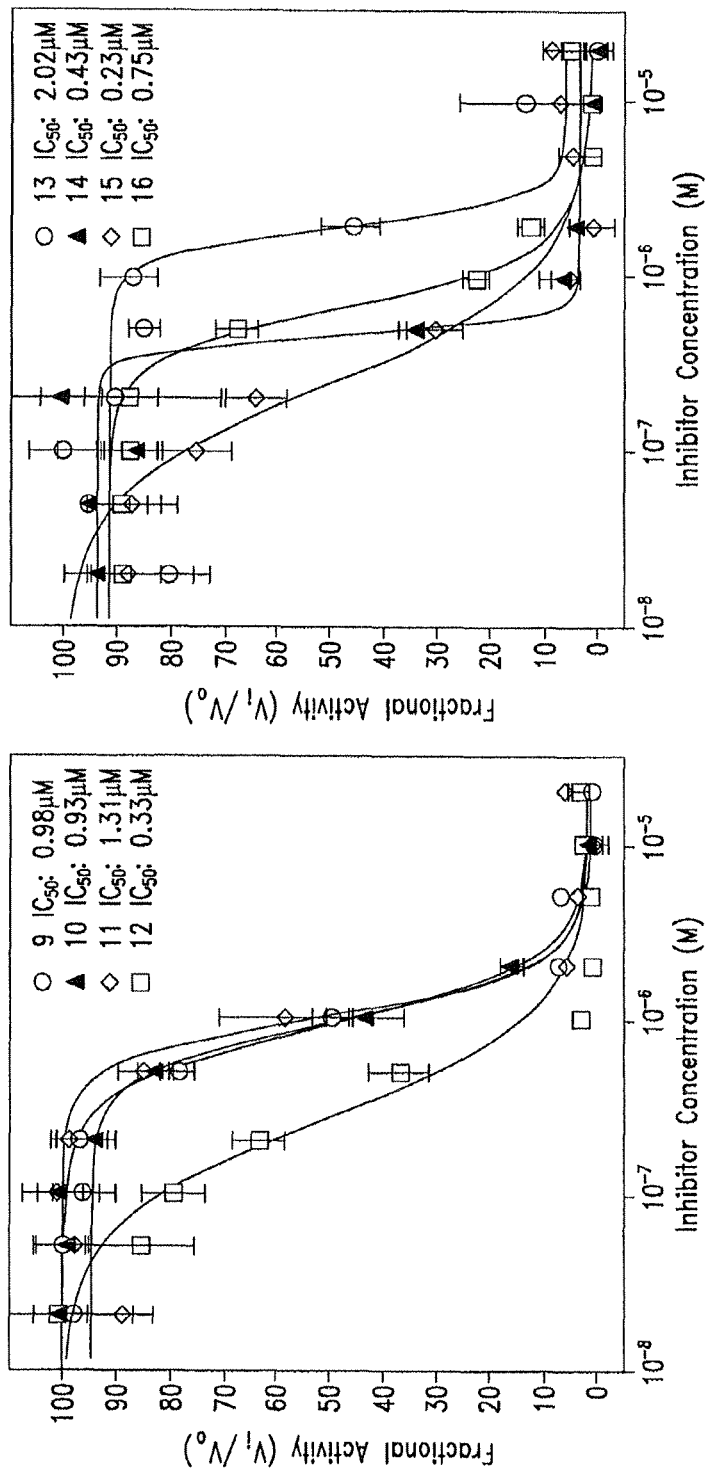
(FIG. 3C) Compounds 9-12.
(FIG. 3D) Compounds 13-16. Purified recombinant hepsin was preincubated with indicated compounds for 30 minutes at room temperature. The fractional activity of the enzyme toward the chromogenic substrate was then determined with a kinetic microplate reader at 405 nm. The data are the mean of three independent experiments. $IC_{50}$ was calculated by four-parameter non-linear regression curve fitting.

B. High-Throughput Screening and Characterization of Hit Compounds. To identify novel inhibitors of hepsin, the Chembridge DIVERSet™ 10,000 compound high-diversity library was screened using an assay based on the cleavage of the chromogenic peptide. In addition, the NINDS II library of 1040 compounds (MicroSource Discovery) was screened to identify hepsin inhibitors among established drugs and known bioactive molecules. Screens were performed in a 96-well format at a final compound concentration of 2 μM. To minimize false positives, positions 1 and 12 of each row contained DMSO/buffer controls. As a measure of reproducibility, the Z' score for this assay was 0.78 (Zhang et al., 1999 *J Biomol Screen* 4:67). Compounds that showed >90% inhibition were individually reproduced. Reproduced hits were reordered from the supplier and their inhibitory activity was confirmed (FIG. 2). The $IC_{50}$ values for these compounds were determined by titration of the compounds against kinetic hepsin activity (FIG. 3). Relative specificity was determined by titration against the serine proteases trypsin and thrombin (Table 1).

TABLE 1

| Compound | Library | ID | $IC_{50}$ hepsin (μM) | $IC_{50}$ trypsin (μM) | $IC_{50}$ thrombin (μM) |
|---|---|---|---|---|---|
| 1 (I-1) | Chembridge Diverset | 5133201 | 0.28 ± 0.07 | 3.88 ± 0.85 | * |
| 2 (II-1) | Chembridge Diverset | 6066621 | 0.76 ± 0.26 | >20 | >20 |
| 3 (III-1) | Chembridge Diverset | 6232890 | 1.93 ± 0.39 | 7.63 ± 1.51 | >20 |
| 4 (IV-1) | Chembridge Diverset | 6071655 | 0.35 ± 0.12 | 19.6 ± 2.7 | >20 |
| 5 (V-1) | Chembridge Diverset | 5655336 | 0.57 ± 0.19 | 31.2 ± 2.0 | >20 |
| 6 (V-2) | Chembridge Diverset | 5658856 | 0.98 ± 0.20 | 10.2 ± 1.5 | >20 |
| 7 (VI-1) | Chembridge Diverset | 5770901 | 2.31 ± 0.53 | 13.1 ± 3.0 | >20 |
| 8 (II-2) | Chembridge Diverset | 6066971 | 0.72 ± 0.20 | 1.71 ± 0.21 | >20 |
| 9 (VII-1) | Chembridge Diverset | 6238388 | 0.98 ± 0.12 | 20.9 ± 7.5 | >20 |
| 10 (VIII-1) | Chembridge Diverset | 6132801 | 0.93 ± 0.13 | 7.72 ± 1.10 | >20 |
| 11 (IX-1) | Chembridge Diverset | 6176059 | 1.31 ± 0.44 | 2.00 ± 0.33 | >20 |
| 12 (X-1) | Chembridge Diverset | 6011640 | 0.33 ± 0.07 | 3.50 ± 0.67 | >20 |
| 13 (XI-1) | NINDS II | meclizine | 2.02 ± 0.37 | >20 | >20 |
| 14 (XII-1) | NINDS II | probucol | 0.43 ± 0.05 | 33.5 ± 11.5 | >20 |
| 15 (XIII-1) | NINDS II | anthralin | 0.23 ± 0.05 | 1.26 ± 0.30 | >20 |
| 16 (XIV-1) | NINDS II | NMDA antagonist | 0.75 ± 0.09 | 2.42 ± 0.29 | >20 |

Table 1 shows potency and specificity of identified hepsin inhibitors. Purified recombinant hepsin was preincubated with indicated compounds for 30 minutes at room temperature. The fractional activity of the enzyme toward the chromogenic substrate was then determined with a kinetic microplate reader at 405 nm. $IC_{50}$ was calculated fitting the triplicate data to a four-parameter non-linear regression. (*Compound 1 activated thrombin activity, approximately 3-fold at 1 μM.)

The $IC_{50}$ values determined for these compounds against hepsin displayed a range of 0.28-2.31 μM. Compounds 1, 3, 7, 9 and 10 were subject to nucleophilic addition and they may have reacted with the serine protease active site serine γO. Analysis of the structures of compounds 2 and 8 revealed a common chlorophenyl substituted thiadiazolurea core, with compound 2 displaying higher specificity for hepsin. Compounds 5 and 6 shared a tetrahydro-3H-cyclopenta[c]quinoline core, with compound 5 displaying both higher potency and specificity. Compound 3 shared an indole moiety with LY178550 (Chirgadze et al., 1997 *Protein Sci.* 6:1412), the N—H of which forms a hydrogen bond to the γO of the catalytic serine of thrombin.

Four total hits were identified from the NINDS II library of drugs and bioactive molecules (compounds 13-16). Interestingly, compounds 13 and 14 (meclizine and probucol) were previously established as human-use drugs with oral dosing, and were identified herein as non-cytotoxic hepsin inhibitors. Meclizine is an anti-nausea drug that is available as an over-the-counter remedy for motion sickness. It displayed moderate potency, >10-fold specificity and was able, as shown in this Example, to attenuate hepsin-mediated pericellular proteolytic activity by 30% at 50 μM. Probucol is an antihyperlipidemic agent developed for use in coronary artery disease and was a potent and specific in vitro inhibitors of hepsin proteolytic activity, as shown in this Example. Without wishing to be bound by theory, probucol may not have shown an ability to reduce pericellular serine protease activity in the cell-based assay described in the present Examples due to its high hydrophobicity. This compound has an approximate logP value of 10, is known to be transported almost exclusively by lipoprotein vesicles in serum and to be delivered from these directly into the cell membrane (Satonin et al., 1986 *J. Chromatog.* 380:401; Wu et al., 2004 *J. Biol. Chem.* 279:30168). Water-soluble analogues of probucol, MDL 29311 and AGI-1067, have been synthesized (Sheetz et al., 1994 *Metabolism* 43:233; Tardif et al., 2003 *Circulation* 107:552), and as such the present inventors expressly contemplate these analogues as hepsin inhibitors for use according to certain herein described embodiments, including as lead compounds for further development of additional hepsin inhibitors.

Compound 15 (anthralin) was previously identified as a topically administered anti-psoratic agent. Compound 16 (2,3-dyhydroxy-6,7-dichloroquinoxaline, an NMDA receptor antagonist) shared a tetrasubstituted pyrazine with amiloride, a selective, moderately potent uPA inhibitor (Evans et al., 2000 *Am Surg* 66:460).

Trypsin is a broadspectrum serine protease with roles in digestion, defense, development and blood coagulation. Thrombin is a chymotrypsin-like serine protease that converts fibrinogen to fibrin and has other roles in blood coagulation. As shown in Table 1, several of the compounds had substantial selectivity for hepsin, with some displaying up to 78-fold selectivity toward hepsin versus trypsin, and >87-fold selectivity toward hepsin versus thrombin.

Figure 4:
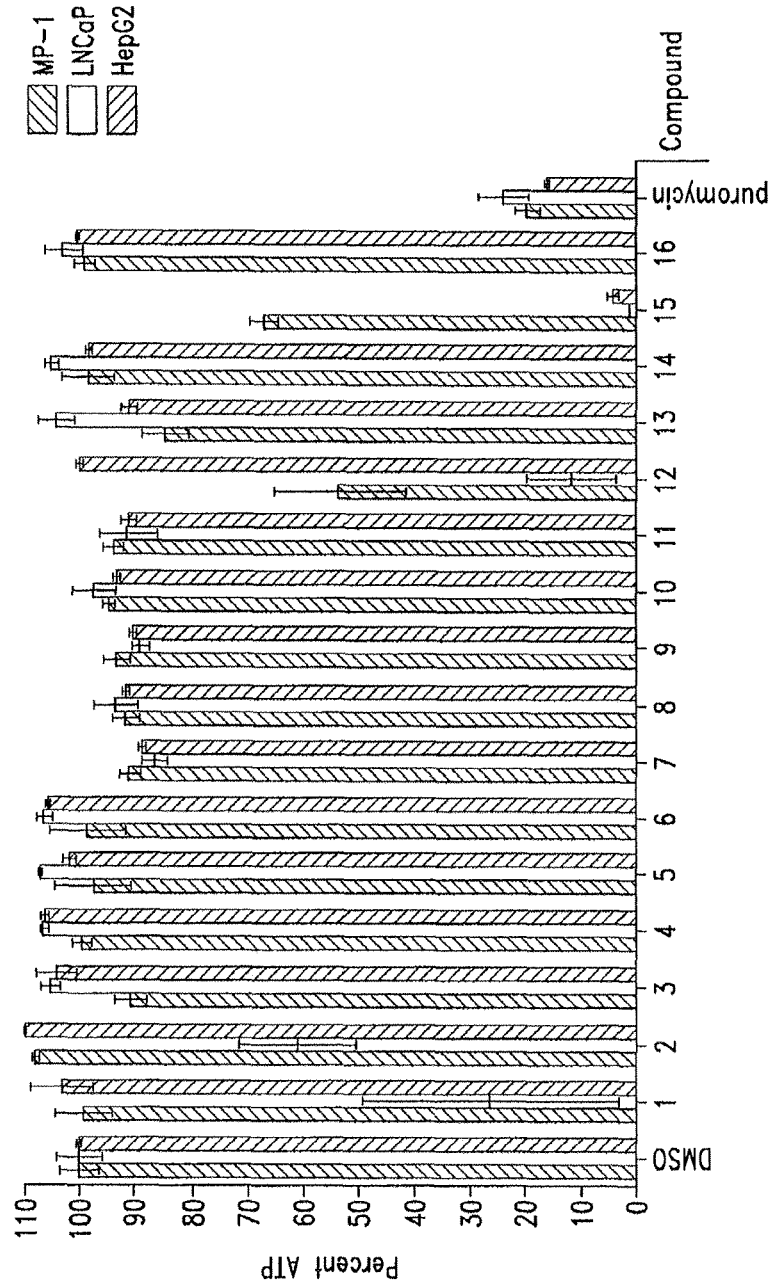
FIG. 4 shows cellular toxicity of identified hepsin inhibitors. The mouse prostate epithelial cell line MP-1 (white bars), human prostate cancer cell line LNCaP (grey bars) and human hepatoma cell line HepG2 (black bars) were incubated for 72 hours with 20 µM of the indicated compounds in media with 0.5% DMSO. Media and drugs were replaced every 24 hours. Cell viability was then determined by an ATP-luciferase coupled assay. Puromycin at 5 µg/mL and DMSO at 0.5% were used respectively as positive control and negative control.

C. General Cellular Toxicity. To provide an estimate of cellular toxicity and the usefulness of the identified inhibitors in cell-based systems, general cellular toxicity assays were performed. For this purpose, 20 µM compounds were incubated with a variety of cell types including the mouse prostate epithelial cell line MP-1, the human hepatoma cell line HepG2 and the human prostate cancer cell line LNCaP (FIG. 4). Compounds and media were replenished daily for three days. At the end of incubation, cell viability was measured using an ATP-luciferase coupled assay. Compounds 1 and 2 displayed substantial toxicity to LNCaP cells without affecting MP-1 or HepG2 cells. Compound 12 was substantially toxic to LNCaP and MP-1 cells without affecting HepG2 cells. Compound 15 (a known inhibitor of cellular respiration, metabolism and DNA synthesis (Schmidt et al., 1996 *J. Immunol.* 156:4514) was toxic to all cell types, particularly to LNCaP and HepG2 cells. Compounds 3, 4, 5, 6, 7, 8, 9, 10, 11, 13, 14 and 16 displayed limited or no cytotoxicity to these cells at this concentration.

Figures 5A, 5B:
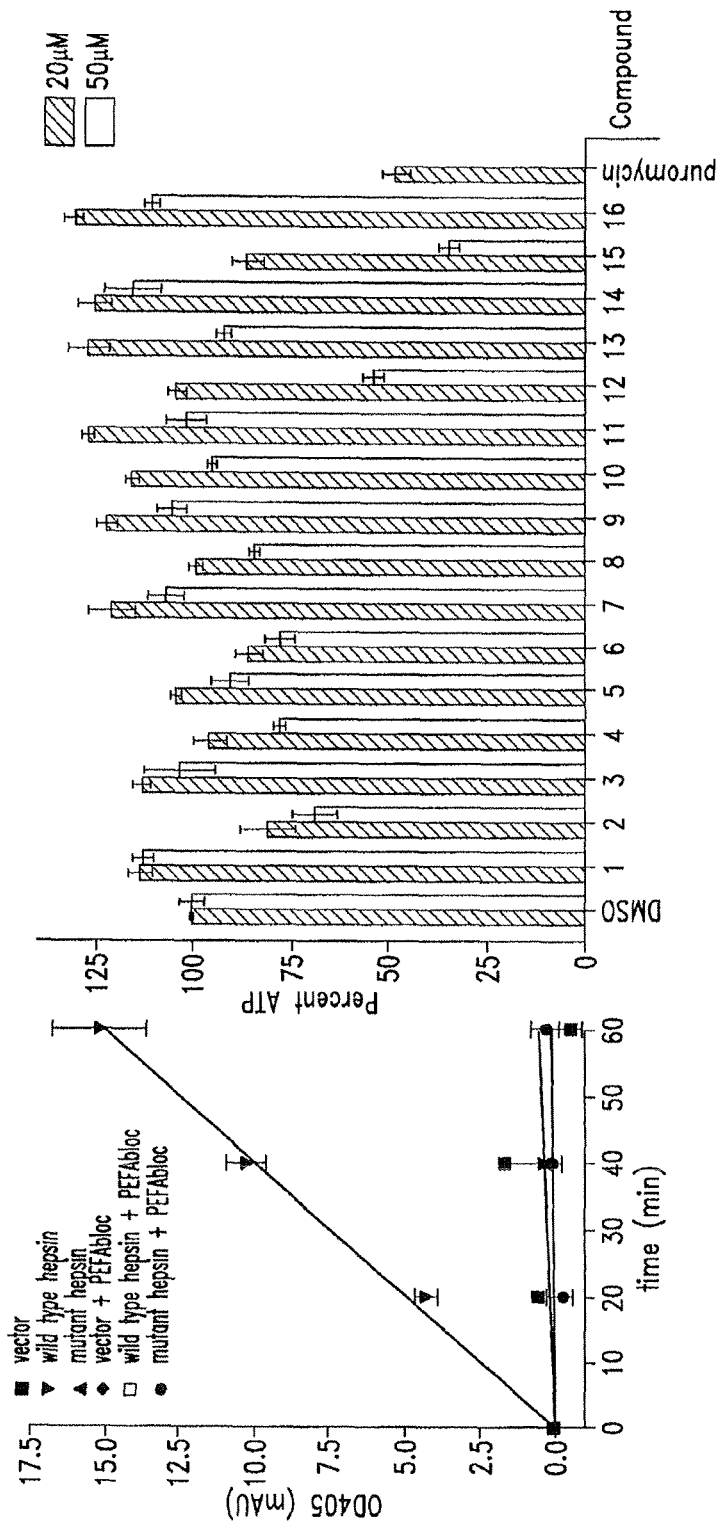
(FIG. 5A) 293FT cells expressing full-length wild-type murine hepsin (SEQ ID NO:9), a catalytically inactive murine hepsin (S352A) mutant (SEQ ID NO:12), or an empty vector control were incubated for 30 minutes in serum-free media containing vehicle alone or the broad spectrum serine protease inhibitor PEFAbloc. The chromogenic serine protease substrate pyroglutamyl-L-prolyl-L-argininne-p-nitroaniline hydrochloride (pyrGlu-Pro-Arg-pNA) was then added to the media. The media with cleaved substrate were collected at indicated times, quenched and pericellular proteolytic activity observed as absorbance at 405 nm. The cells expressing wild-type hepsin, but not the cells expressing inactive mutant hepsin, vector alone or wild-type hepsin in the presence of PEFAbloc, displayed pericellular proteolytic activity.
(FIG. 5B) Toxicity of the candidate hepsin inhibitor compounds over the course of the pericellular protease assay was evaluated by 24-hour treatment of cells with 20 µM (white bars) or 50 µM (black bars) compounds, relative to vehicle control. Cell viability was then determined by an ATP-luciferase coupled assay. Puromycin at 5 µg/mL was used as a positive control.

D. Inhibition of Hepsin-Dependent Pericellular Proteolytic Activity. To determine whether the identified compounds were able to inhibit cell-based hepsin activity, an assay was devised to measure hepsin-dependent pericellular serine proteolytic activity (FIG. 5A) (Raynaud et al., 1992 *J Cell Physiol* 151:378; Bauvois et al., 1990 *Eur. J. Immunol.* 20:459; Bauvois et al., 1992 *Eur. J. Immunol.* 22:923; Sameni et al., 2000 *Neoplasia* 2:496; McGowen et al., 2000 *Canc. Res.* 60:4771). For this purpose, HEK 293FT transfectant cells were used that expressed either full-length wild-type murine hepsin (SEQ ID NO:9) or catalytically inactive (S352A) mutant (SEQ ID NO:12) hepsin proteins, or that had been transfected with empty vector alone. Attached cell monolayers were incubated in assay buffer with peptide substrate and the reactions were allowed to proceed at 37° C. Samples were withdrawn at 20, 40 and 60 minutes, quenched into an equal volume of 7% acetic acid and absorbance at 405 nm measured with a microplate reader. Activity levels were adjusted by altering hepsin expression levels to within the linear range of detection. A positive linear rate of activity was observed only for wild-type hepsin-expressing cells and was abolished in the presence of the broad spectrum serine protease inhibitor PEFAbloc.

To determine the potential cytotoxicity of the previously identified hepsin inhibitors in this model system, HEK 293FT cells were incubated under identical conditions with 20 and 50 µM of the compounds and cytotoxicity was determined using the ATP-luciferase coupled assay as described above (FIG. 5B). Compounds 12 and 15 displayed substantial toxicity at 50 µM and were not further characterized. The remaining compounds at 20 and 50 µM final concentration were incubated overnight with hepsin expressing cells and pericellular proteolytic activity was determined as described above (FIG. 6).

As treatment with chemical compounds may alter hepsin expression level (and thereby impact pericellular proteolytic activity), hepsin levels in drug-treated cells were determined via immunoblotting (FIG. 6B). Data are displayed in FIG. 6A as pericellular proteolytic activity/expression level relative to vehicle treated wild-type hepsin expressing cells. Compounds 3, 4, 5 and 13 attenuated pericellular proteolytic activity in a dose dependent manner without substantially affecting hepsin expression levels or displaying overt toxicity. Of those tested, Compounds 4 and 5 offered the most potent inhibition, attenuating activity approximately 60% at 50 µM. Compounds 3 and 13 reduced activity approximately 50% and 25% (respectively) at 50 µM.

BIOLOGICAL EXAMPLE 3

In Vivo Attenuation by Hepsin Inhibitors of Metastatic Prostate Cancer

This Example describes effects of hepsin inhibitors that have been identified as described above, on prostate cancer progression and metastasis in vivo.

LPB-Tag/PB-Hepsin transgenic mice are prepared as described in Klezovitch et al. (2004 *Cancer Cell* 6:185); these animals exhibit early prostate cancer at about 10 weeks of age.

Regimen A. Groups of eight LPB-Tag/PB-Hepsin transgenic mice, aged 10 weeks, are orally administered either compound 13 (meclizine, 0.1% wt/wt) or compound 14 (probucol, 1% wt/wt) or vehicle control, each mixed with dry standard laboratory rodent chow. Meclizine and probucol are approved for oral administration to humans, and were identified herein as non-cytotoxic hepsin inhibitors as described above. Animals are maintained until aged 21 weeks, at which point about half of the animals in each group develop metastatic prostate cancer. The animals are terminated by $CO_2$ inhalation, dissected, and the primary prostate and distal organs are analyzed histologically according to the methodologies of Klezovitch et al. (2004). Scoring of histology tissues for metastatic lesions is performed to compare experimentally treated (meclizine or probucol) and control untreated animals.

Regimen B. Drug compounds are handled according to procedures found in the handbook of animal care practices (HAMM) of the Fred Hutchinson Cancer Research Center (Seattle, Wash.) Chapter III Sections 12.11.2 and 12.11.3. Groups of eight LPB-Tag/PB-Hepsin transgenic mice, aged 10 weeks, are intraperitoneally administered three times per week one of Compounds 3, 4, 5, 6, 7, 8, 9, 10, 11 and 16 or vehicle control, at a maximum tolerable dose as determined by an absence of signs of discomfort. These compounds were identified herein as non-cytotoxic hepsin inhibitors as described above. Animals are maintained until aged 21 weeks, at which point about half of the animals in each group develop metastatic prostate cancer. The animals are terminated by $CO_2$ inhalation, dissected, and the primary prostate and distal organs are analyzed histologically according to the methodologies of Klezovitch et al. (2004). Scoring of histology tissues for metastatic lesions is performed to compare experimentally treated (Compound 3, 4, 5, 6, 7, 8, 9, 10, 11 or 16) and control untreated animals.

Literature Cited 1. (2008). Cancer Facts and Figures, American Cancer Society.
2. (2007). The Prostate-Specific Antigen (PSA) Test: Questions and Answers, US National Institutes of Health.
3. (2007). Early Prostate Cancer: Questions and Answers, US National Institutes of Health.
4. Vasioukhin, V. (2004). Hepsin paradox reveals unexpected complexity of metastatic process. *Cell Cycle* 3, 1394-1397.
5. Bradford, T. J., Tomlins, S. A., Wang, X., and Chinnaiyan, A. M. (2006). Molecular markers of prostate cancer. *Urol Oncol* 24, 538-551.
6. Magee, J. A., Araki, T., Patil, S., Ehrig, T., True, L., Humphrey, P. A., Catalona, W. J., Watson, M. A., and Milbrandt, J. (2001). Expression profiling reveals hepsin overexpression in prostate cancer. *Cancer Res* 61, 5692-5696.
7. Dhanasekaran, S. M., Barrette, T. R., Ghosh, D., Shah, R., Varambally, S., Kurachi, K., Pienta, K. J., Rubin, M. A., and Chinnaiyan, A. M. (2001). Delineation of prognostic biomarkers in prostate cancer. *Nature* 412, 822-826.
8. Stamey, T. A., Warrington, J. A., Caldwell, M. C., Chen, Z., Fan, Z., Mahadevappa, M., McNeal, J. E., Nolley, R., and Zhang, Z. (2001). Molecular genetic profiling of Gleason grade 4/5 prostate cancers compared to benign prostatic hyperplasia. *J Urol* 166, 2171-2177.
9. Tanimoto, H., Yan, Y., Clarke, J., Korourian, S., Shigemasa, K., Parmley, T. H., Parham, G. P., and O'Brien, T. J. (1997). Hepsin, a cell surface serine protease identified in hepatoma cells, is overexpressed in ovarian cancer. *Cancer Res* 57, 2884-2887. 19
10. Zacharski, L. R., Ornstein, D. L., Memoli, V. A., Rousseau, S. M., and Kisiel, W. (1998). Expression of the factor VII activating protease, hepsin, in situ in renal cell carcinoma. *Thromb Haemost* 79, 876-877.
11. Klezovitch, O., Chevillet, J., Mirosevich, J., Roberts, R. L., Matusik, R. J., and Vasioukhin, V. (2004). Hepsin promotes prostate cancer progression and metastasis. *Cancer Cell* 6, 185-195.
12. Srikantan, V., Valladares, M., Rhim, J. S., Moul, J. W., and Srivastava, S. (2002). HEPSIN inhibits cell growth/invasion in prostate cancer cells. *Cancer Res* 62, 6812-6816.
13. Moran, P., Li, W., Fan, B., Vij, R., Eigenbrot, C., and Kirchhofer, D. (2006). Prourokinase-type plasminogen activator is a substrate for hepsin. *J Biol Chem* 281, 30439-30446.
14. Kirchhofer, D., Peek, M., Lipari, M. T., Billeci, K., Fan, B., and Moran, P. (2005). Hepsin activates pro-hepatocyte growth factor and is inhibited by hepatocyte growth factor activator inhibitor-1B (HAI-1B) and HAI-2. *FEBS Lett* 579, 1945-1950.
15. Fear, G., Komarnytsky, S., and Raskin, I. (2007). Protease inhibitors and their peptidomimetic derivatives as potential drugs. *Pharmacol Ther* 113, 354-368.
16. Abbenante, G., and Fairlie, D. P. (2005). Protease inhibitors in the clinic. *Med Chem* 1, 71-104.
17. Somoza, J. R., Ho, J. D., Luong, C., Ghate, M., Sprengeler, P. A., Mortara, K., Shrader, W. D., Sperandio, D., Chan, H., McGrath, M. E., and Katz, B. A. (2003). The structure of the extracellular region of human hepsin reveals a serine protease domain and a novel scavenger receptor cysteine-rich (SRCR) domain. *Structure* 11, 1123-1131.
18. Zhang, J. H., Chung, T. D., and Oldenburg, K. R. (1999). A Simple Statistical Parameter for Use in Evaluation and Validation of High Throughput Screening Assays. *J Biomol Screen* 4, 67-73.
19. Chirgadze, N. Y., Sall, D. J., Klimkowski, V. J., Clawson, D. K., Briggs, S. L., Hermann, R., Smith, G. F., Gifford-Moore, D. S., and Wary, J. P. (1997). The crystal structure of human alpha-thrombin complexed with LY178550, a non-peptidyl, active site-directed inhibitor. *Protein Sci* 6, 1412-1417.
20. Evans, D. M., and Sloan-Stakleff, K. (2000). Suppression of the invasive capacity of human breast cancer cells by inhibition of urokinase plasminogen activator via amiloride and B428. *Am Surg* 66, 460-464.
21. Schmidt, K. N., Podda, M., Packer, L., and Baeuerle, P. A. (1996). Anti-psoriatic drug anthralin activates transcription factor NF-kappa B in murine keratinocytes. *J Immunol* 156, 4514-4519.
22. Raynaud, F., Bauvois, B., Gerbaud, P., and Evain-Brion, D. (1992). Characterization of specific proteases associated with the surface of human skin fibroblasts, and their modulation in pathology. *J Cell Physiol* 151, 378-385.
23. Bauvois, B. (1990). Murine thymocytes possess specific cell surface-associated exoaminopeptidase activities: preferential expression by immature CD4-CD8-subpopulation. *Eur J Immunol* 20, 459-468.
24. Bauvois, B., Sanceau, J., and Wietzerbin, J. (1992). Human U937 cell surface peptidase activities: characterization and degradative effect on tumor necrosis factor-alpha. *Eur J Immunol* 22, 923-930.
25. Sameni, M., Moin, K., and Sloane, B. F. (2000). Imaging proteolysis by living human breast cancer cells. *Neoplasia* 2, 496-504.
26. McGowen, R., Biliran, H., Jr., Sager, R., and Sheng, S. (2000). The surface of prostate carcinoma DU145 cells mediates the inhibition of urokinase-type plasminogen activator by maspin. *Cancer Res* 60, 4771-4778.
27. Satonin, D. K., and Coutant, J. E. (1986). Comparison of gas chromatography and high-performance liquid chromatography for the analysis of probucol in plasma. *J Chromatogr* 380, 401-406.
28. Wu, C. A., Tsujita, M., Hayashi, M., and Yokoyama, S. (2004). Probucol inactivates ABCA1 in the plasma membrane with respect to its mediation of apolipoprotein binding and high density lipoprotein assembly and to its proteolytic degradation. *J Biol Chem* 279, 30168-30174.
29. Sheetz, M. J., Barnhart, R. L., Jackson, R. L., and Robinson, K. M. (1994). MDL 29311, an analog of probucol, decreases triglycerides in rats by increasing hepatic clearance of very-low-density lipoprotein. *Metabolism* 43, 233-240.
30. Tardif, J. C., Gregoire, J., Schwartz, L., Title, L., Laramee, L., Reeves, F., Lesperance, J., Bourassa, M. G., L'Allier, P. L., Glass, M., Lambert, J., and Guertin, M. C. (2003). Effects of AGI-1067 and probucol after percutaneous coronary interventions. *Circulation* 107, 552-558.

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A method for determining cancer progression or metastasis of a cancer that is characterized by cancer cells in which hepsin overexpression is present, comprising:
    (a) contacting (i) a hepsin inhibitor with (ii) a cancer cell that comprises a cell surface hepsin polypeptide, under conditions and for a time sufficient for the hepsin inhibitor to physically contact the cell surface hepsin polypeptide and thereby inhibit hepsin proteolytic activity on the cell surface, wherein the hepsin inhibitor is detectable by radiological imaging, fluorescence magnetic resonance imaging, immunofluorescence imaging, immunohistologic imaging, immunologic detection, biochemical detection or histochemical detection; and
    (b) detecting the hepsin inhibitor by radiological imaging, fluorescence magnetic resonance imaging, immunofluorescence imaging, immunohistologic imaging, immunologic detection, biochemical detection or histochemical detection, and thereby determining cancer progression or metastasis,
wherein the cell surface hepsin polypeptide is selected from the group consisting of:
    (i) a cell surface polypeptide comprising the amino acid sequence set forth in any one of SEQ ID NOS:1, 6 and 9,
    (ii) a cell surface polypeptide comprising an amino acid sequence that is at least 85%, 90% or 95% identical to the polypeptide of (i) and that is capable of specific enzymatic cleavage of a chromogenic serine protease substrate that comprises L-pyroglutamyl-L-prolyl-L-arginine-p-nitroaniline hydrochloride (Glu-Pro-Arg-pNA), and (iii) a cell surface polypeptide that comprises a hepsin catalytic domain or a functional fragment thereof, said hepsin catalytic domain or functional fragment thereof comprising an amino acid sequence that is at least 80%; 85%, 90% or 95% identical to the amino acid sequence set forth in any one of SEQ ID NOS:5, 8 and 11 and that is capable of specific enzymatic cleavage of a chromogenic serine protease substrate that comprises L-pyroglutamyl-L-prolyl-L-arginine-p-nitroaniline hydrochloride (pyroGlu-Pro-Arg-pNA), and wherein the hepsin inhibitor comprises at least one compound that is selected from a compound of formula (IV), a compound of formula (V) and a compound of formula (VIII):

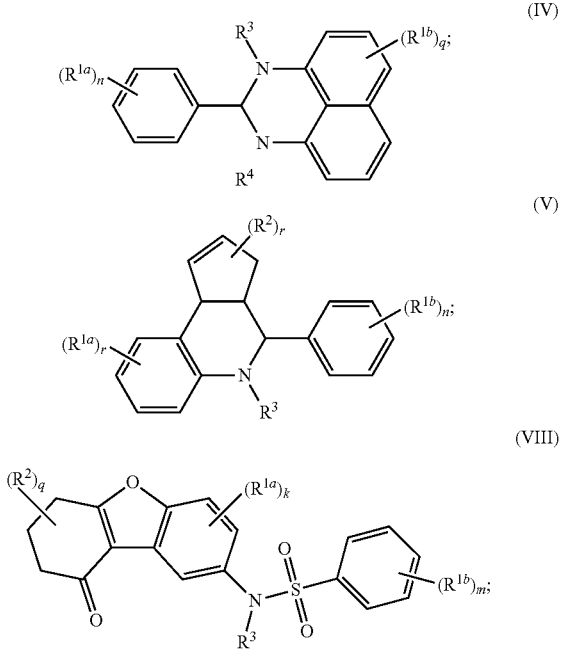

wherein:
each k is 1, 2 or 3;
each m is 1 or 2;
each n is 1, 2, 3, 4 or 5;
each r is 1, 2, 3 or 4;
q is 1, 2, 3, 4, 5 or 6;
each $R^{1a}$ and $R^{1b}$ is independently selected from the group consisting of hydrogen, alkyl, halo, haloalkyl, optionally substituted aryl, optionally substituted aralkyl, —$OR^7$, —CN, —$C(O)R^7$, —$C(O)OR^7$, —$C(O)N(R^7)R^8$, —$NO_2$, —$N(R^7)R^8$, —$N(R^7)C(O)R^8$, and —$N(R^7)C(O)OR^8$;
each $R^2$ is independently selected from the group consisting of hydrogen, alkyl, halo, haloalkyl, optionally substituted aryl and optionally substituted aralkyl;
each $R^3$ and $R^4$ is independently selected from the group consisting of hydrogen, alkyl, optionally substituted aryl and optionally substituted aralkyl; and
each $R^7$ and $R^8$ is independently selected from the group consisting of hydrogen, alkyl, optionally substituted aryl and optionally substituted aralkyl;
as a single stereoisomer or a mixture thereof;
or a pharmaceutically acceptable salt thereof.

2. The method of claim 1 which is selected from (1) the method wherein contacting takes place in vivo and (2) the method wherein contacting takes place in vitro.

3. The method of claim 1 wherein the hepsin inhibitor comprises detection means selected from an isotope label or radiolabel, a fluorescence magnetic resonance label, an immunofluorescence label, an immunohistologic label, an immunologic label, a biochemical label and a histochemical label.

4. The method of claim 3 wherein the isotope label or radiolabel is selected from the group consisting of $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$.

5. The method of claim 1 wherein the compound is a compound of formula (VIII):

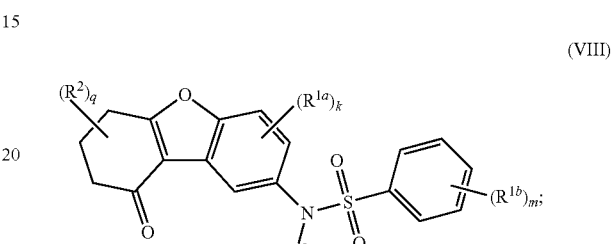

wherein:
k is 1, 2 or 3;
m is 1 or 2;
q is 1, 2, 3, 4, 5 or 6;
each $R^{1a}$ and $R^{1b}$ is independently selected from the group consisting of hydrogen, alkyl, halo, haloalkyl, optionally substituted aryl, optionally substituted aralkyl, —$OR^7$, —CN, —$C(O)R^7$, —$C(O)OR^7$, —$C(O)N(R^7)R^8$, —$NO_2$, —$N(R^7)R^8$, —$N(R^7)C(O)R^8$, and —$N(R^7)C(O)OR^8$;
each $R^2$ is independently selected from the group consisting of hydrogen, alkyl, halo, haloalkyl, optionally substituted aryl and optionally substituted aralkyl;
$R^3$ is selected from the group consisting of hydrogen, alkyl, optionally substituted aryl and optionally substituted aralkyl; and
each $R^7$ and $R^8$ is independently selected from the group consisting of hydrogen, alkyl, optionally substituted aryl and optionally substituted aralkyl;
as a single stereoisomer or a mixture thereof;
or a pharmaceutically acceptable salt thereof.

6. The method of claim 5 wherein the compound is a compound of formula (VIII) wherein:
k is 1;
m is 1;
q is 2;
$R^{1a}$ and $R^{1b}$ are each independently selected from the group consisting of hydrogen and halo;
each $R^2$ is alkyl; and
$R^3$ is selected from the group consisting of hydrogen and alkyl.

7. The method of claim 6 wherein the compound of formula (VIII) is N-(4-bromo-7,7-dimethyl-9-oxo-6,7,8,9-tetrahydrodibenzo[b,d]furan-2-yl)benzenesulfonamide.

8. The method of claim 1 wherein the compound is a compound of formula (IV):

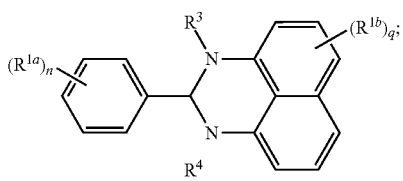

(IV)

wherein:

n is 1, 2, 3, 4 or 5;

q is 1, 2, 3, 4, 5 or 6;

each $R^{1a}$ and $R^{1b}$ is independently selected from the group consisting of hydrogen, alkyl, halo, haloalkyl, optionally substituted aryl, optionally substituted aralkyl, —$OR^7$, —CN, —C(O)$R^7$, —C(O)O$R^7$, —C(O)N($R^7$)$R^8$, —$NO_2$, —N($R^7$)$R^8$, —N($R^7$)C(O)$R^8$, and —N($R^7$)C(O)O$R^8$;

$R^3$ and $R^4$ are each independently selected from the group consisting of hydrogen, alkyl, optionally substituted aryl and optionally substituted aralkyl; and each $R^7$ and $R^8$ is independently selected from the group consisting of hydrogen, alkyl, optionally substituted aryl and optionally substituted aralkyl;

as a single stereoisomer or a mixture thereof;

or a pharmaceutically acceptable salt thereof.

9. The method of claim 8 wherein the compound is a compound of formula (IV) wherein:

n is 1;

q is 1;

$R^{1a}$ and $R^{1b}$ are each independently selected from the group consisting of hydrogen and alkyl; and $R^3$ and $R^4$ are each independently selected from the group consisting of hydrogen and alkyl.

10. The method of claim 9 wherein the compound of formula (IV) is 2-(3-methylphenyl)-2,3-dihydro-1H-perimidine.

11. The method of claim 1 wherein the compound is a compound of formula (V):

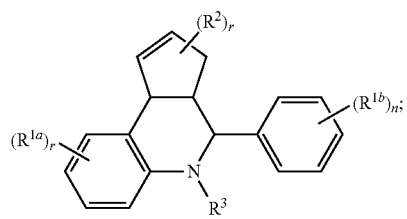

(V)

wherein:

n is 1, 2, 3, 4 or 5;

each r is 1, 2, 3 or 4;

each $R^{1a}$ and $R^{1b}$ is independently selected from the group consisting of hydrogen, alkyl, halo, haloalkyl, optionally substituted aryl, optionally substituted aralkyl, —$OR^7$, —CN, —C(O)$R^7$, —C(O)O$R^7$, —C(O)N($R^7$)$R^8$, —$NO_2$, —N($R^7$)$R^8$, —N($R^7$)C(O)$R^8$, and —N($R^7$)C(O)O$R^8$;

each $R^2$ is independently selected from the group consisting of hydrogen, alkyl, halo, haloalkyl, optionally substituted aryl and optionally substituted aralkyl;

$R^3$ is selected from the group consisting of hydrogen, alkyl, optionally substituted aryl and optionally substituted aralkyl; and each $R^7$ and $R^8$ is independently selected from the group consisting of hydrogen, alkyl, optionally substituted aryl and optionally substituted aralkyl;

as a single stereoisomer or a mixture thereof;

or a pharmaceutically acceptable salt thereof.

12. The method of claim 11 wherein the compound is a compound of formula (V) wherein:

n is 1;

each r is 1;

$R^{1a}$ and $R^{1b}$ are each independently selected from the group consisting of hydrogen, halo, haloalkyl and —$NO_2$;

$R^2$ is selected from the group consisting of hydrogen and alkyl; and $R^3$ is selected from the group consisting of hydrogen and alkyl.

13. The method of claim 12 wherein the compound of formula (V) is selected from the group consisting of:

4-(4-nitrophenyl)-6-(trifluoromethyl)-3a,4,5,9b-tetrahydro-3H-cyclopenta[c]quinoline; and 8-chloro-4-(3-nitrophenyl)-3a,4,5,9b-tetrahydro-3H-cyclopenta[c]quinoline.

14. The method of claim 1 wherein the cancer that is characterized by cancer cells in which hepsin overexpression is present is prostate cancer.

15. The method of claim 14 wherein the prostate cancer is prostatic intraepithelial neoplasia, prostate-confined non-invasive low grade cancer, prostate-confined invasive cancer, or metastatic prostate cancer.

16. The method of claim 1 wherein the cancer that is characterized by cancer cells in which hepsin overexpression is present is ovarian cancer.

17. The method of claim 16 wherein the ovarian cancer is stage I, stage II, stage III, stage IV or recurrent ovarian cancer.

18. The method of claim 1 wherein the cancer that is characterized by cancer cells in which hepsin overexpression is present is renal cell carcinoma.

19. The method of claim 18 wherein the renal cell carcinoma is stage I, stage II, stage III, or stage IV renal cell carcinoma.

20. The method of claim 1 wherein the cancer that is characterized by cancer cells in which hepsin overexpression is present is endometrial cancer.

21. The method of claim 20 wherein the endometrial cancer is stage I, stage II, stage III, or stage IV endometrial cancer.

22. The method of claim 1 wherein contacting comprises administering the hepsin inhibitor to a subject orally, parenterally, intraperitoneally, intravenously, intraarterially, transdermally, sublingually, subcutaneously, intramuscularly, rectally, transbuccally, intranasally, liposomally, via inhalation, intraocularly, via local delivery, subcutaneously, intraadiposally, intraarticularly or intrathecally.

* * * * *

SEQUENCE LISTING

<160> NUMBER OF SEQ ID NOS: 12

<210> SEQ ID NO 1
<211> LENGTH: 417
<212> TYPE: PRT
<213> ORGANISM: Homo sapiens

<400> SEQUENCE: 1

Met Ala Gln Lys Glu Gly Gly Arg Thr Val Pro Cys Cys Ser Arg Pro
 1               5                  10                  15

Lys Val Ala Ala Leu Thr Ala Gly Thr Leu Leu Leu Thr Ala Ile
            20                  25                  30

Gly Ala Ala Ser Trp Ala Ile Val Ala Val Leu Leu Arg Ser Asp Gln
            35                  40                  45

Glu Pro Leu Tyr Pro Val Gln Val Ser Ser Ala Asp Ala Arg Leu Met
        50                  55                  60

Val Phe Asp Lys Thr Glu Gly Thr Trp Arg Leu Leu Cys Ser Ser Arg
65                  70                  75                  80

Ser Asn Ala Arg Val Ala Gly Leu Ser Cys Glu Glu Met Gly Phe Leu
                85                  90                  95

Arg Ala Leu Thr His Ser Glu Leu Asp Val Arg Thr Ala Gly Ala Asn
            100                 105                 110

Gly Thr Ser Gly Phe Phe Cys Val Asp Glu Gly Arg Leu Pro His Thr
        115                 120                 125

Gln Arg Leu Leu Glu Val Ile Ser Val Cys Asp Cys Pro Arg Gly Arg
    130                 135                 140

Phe Leu Ala Ala Ile Cys Gln Asp Cys Gly Arg Arg Lys Leu Pro Val
145                 150                 155                 160

Asp Arg Ile Val Gly Gly Arg Asp Thr Ser Leu Gly Arg Trp Pro Trp
                165                 170                 175

Gln Val Ser Leu Arg Tyr Asp Gly Ala His Leu Cys Gly Gly Ser Leu
            180                 185                 190

Leu Ser Gly Asp Trp Val Leu Thr Ala Ala His Cys Phe Pro Glu Arg
        195                 200                 205

Asn Arg Val Leu Ser Arg Trp Arg Val Phe Ala Gly Ala Val Ala Gln
    210                 215                 220

Ala Ser Pro His Gly Leu Gln Leu Gly Val Gln Ala Val Val Tyr His
225                 230                 235                 240

Gly Gly Tyr Leu Pro Phe Arg Asp Pro Asn Ser Glu Glu Asn Ser Asn
                245                 250                 255

Asp Ile Ala Leu Val His Leu Ser Ser Pro Leu Pro Leu Thr Glu Tyr
            260                 265                 270

Ile Gln Pro Val Cys Leu Pro Ala Ala Gly Gln Ala Leu Val Asp Gly
        275                 280                 285

Lys Ile Cys Thr Val Thr Gly Trp Gly Asn Thr Gln Tyr Tyr Gly Gln
    290                 295                 300

Gln Ala Gly Val Leu Gln Glu Ala Arg Val Pro Ile Ile Ser Asn Asp
305                 310                 315                 320

Val Cys Asn Gly Ala Asp Phe Tyr Gly Asn Gln Ile Lys Pro Lys Met
                325                 330                 335

Phe Cys Ala Gly Tyr Pro Glu Gly Gly Ile Asp Ala Cys Gln Gly Asp
            340                 345                 350

Ser Gly Gly Pro Phe Val Cys Glu Asp Ser Ile Ser Arg Thr Pro Arg
        355                 360                 365

```
Trp Arg Leu Cys Gly Ile Val Ser Trp Gly Thr Gly Cys Ala Leu Ala
    370                 375                 380

Gln Lys Pro Gly Val Tyr Thr Lys Val Ser Asp Phe Arg Glu Trp Ile
385                 390                 395                 400

Phe Gln Ala Ile Lys Thr His Ser Glu Ala Ser Gly Met Val Thr Gln
                405                 410                 415

Leu

<210> SEQ ID NO 2
<211> LENGTH: 417
<212> TYPE: PRT
<213> ORGANISM: Homo sapiens

<400> SEQUENCE: 2

Met Ala Gln Lys Glu Gly Gly Arg Thr Val Pro Cys Cys Ser Arg Pro
1               5                   10                  15

Lys Val Ala Ala Leu Thr Ala Gly Thr Leu Leu Leu Leu Thr Ala Ile
                20                  25                  30

Gly Ala Ala Ser Trp Ala Ile Val Ala Val Leu Leu Arg Ser Asp Gln
            35                  40                  45

Glu Pro Leu Tyr Pro Val Gln Val Ser Ser Ala Asp Ala Arg Leu Met
    50                  55                  60

Val Phe Asp Lys Thr Glu Gly Thr Trp Arg Leu Leu Cys Ser Ser Arg
65                  70                  75                  80

Ser Asn Ala Arg Val Ala Gly Leu Ser Cys Glu Glu Met Gly Phe Leu
                85                  90                  95

Arg Ala Leu Thr His Ser Glu Leu Asp Val Arg Thr Ala Gly Ala Asn
                100                 105                 110

Gly Thr Ser Gly Phe Phe Cys Val Asp Glu Gly Arg Leu Pro His Thr
            115                 120                 125

Gln Arg Leu Leu Glu Val Ile Ser Val Cys Asp Cys Pro Arg Gly Arg
    130                 135                 140

Phe Leu Ala Ala Ile Cys Gln Asp Cys Gly Arg Arg Lys Leu Pro Val
145                 150                 155                 160

Asp Arg Ile Val Gly Gly Arg Asp Thr Ser Leu Gly Arg Trp Pro Trp
                165                 170                 175

Gln Val Ser Leu Arg Tyr Asp Gly Ala His Leu Cys Gly Gly Ser Leu
            180                 185                 190

Leu Ser Gly Asp Trp Val Leu Thr Ala Ala His Cys Phe Pro Glu Arg
    195                 200                 205

Asn Arg Val Leu Ser Arg Trp Arg Val Phe Ala Gly Ala Val Ala Gln
210                 215                 220

Ala Ser Pro His Gly Leu Gln Leu Gly Val Gln Ala Val Val Tyr His
225                 230                 235                 240

Gly Gly Tyr Leu Pro Phe Arg Asp Pro Asn Ser Glu Glu Asn Ser Asn
                245                 250                 255

Asp Ile Ala Leu Val His Leu Ser Ser Pro Leu Pro Leu Thr Glu Tyr
            260                 265                 270

Ile Gln Pro Val Cys Leu Pro Ala Ala Gly Gln Ala Leu Val Asp Gly
    275                 280                 285

Lys Ile Cys Thr Val Thr Gly Trp Gly Asn Thr Gln Tyr Tyr Gly Gln
290                 295                 300

Gln Ala Gly Val Leu Gln Glu Ala Arg Val Pro Ile Ile Ser Asn Asp
305                 310                 315                 320
```

```
Val Cys Asn Gly Ala Asp Phe Tyr Gly Asn Gln Ile Lys Pro Lys Met
            325                 330                 335

Phe Cys Ala Gly Tyr Pro Glu Gly Gly Ile Asp Ala Cys Gln Gly Asp
            340                 345                 350

Ser Gly Gly Pro Phe Val Cys Glu Asp Ser Ile Ser Arg Thr Pro Arg
            355                 360                 365

Trp Arg Leu Cys Gly Ile Val Ser Trp Gly Thr Gly Cys Ala Leu Ala
            370                 375                 380

Gln Lys Pro Gly Val Tyr Thr Lys Val Ser Asp Phe Arg Glu Trp Ile
385                 390                 395                 400

Phe Gln Ala Ile Lys Thr His Ser Glu Ala Ser Gly Met Val Thr Gln
            405                 410                 415

Leu

<210> SEQ ID NO 3
<211> LENGTH: 417
<212> TYPE: PRT
<213> ORGANISM: Homo sapiens

<400> SEQUENCE: 3

Met Ala Gln Lys Glu Gly Gly Arg Thr Val Pro Cys Cys Ser Arg Pro
1               5                   10                  15

Lys Val Ala Ala Leu Thr Ala Gly Thr Leu Leu Leu Thr Ala Ile
            20                  25                  30

Gly Ala Ala Ser Trp Ala Ile Val Ala Val Leu Leu Arg Ser Asp Gln
            35                  40                  45

Glu Pro Leu Tyr Pro Val Gln Val Ser Ser Ala Asp Ala Arg Leu Met
    50                  55                  60

Val Phe Asp Lys Thr Glu Gly Thr Trp Arg Leu Leu Cys Ser Ser Arg
65                  70                  75                  80

Ser Asn Ala Arg Val Ala Gly Leu Ser Cys Glu Glu Met Gly Phe Leu
            85                  90                  95

Arg Ala Leu Thr His Ser Glu Leu Asp Val Arg Thr Ala Gly Ala Asn
            100                 105                 110

Gly Thr Ser Gly Phe Phe Cys Val Asp Glu Gly Arg Leu Pro His Thr
            115                 120                 125

Gln Arg Leu Leu Glu Val Ile Ser Val Cys Asp Cys Pro Arg Gly Arg
130                 135                 140

Phe Leu Ala Ala Ile Cys Gln Asp Cys Gly Arg Arg Lys Leu Pro Val
145                 150                 155                 160

Asp Arg Ile Val Gly Gly Arg Asp Thr Ser Leu Gly Arg Trp Pro Trp
            165                 170                 175

Gln Val Ser Leu Arg Tyr Asp Gly Ala His Leu Cys Gly Gly Ser Leu
            180                 185                 190

Leu Ser Gly Asp Trp Val Leu Thr Ala Ala His Cys Phe Pro Glu Arg
            195                 200                 205

Asn Arg Val Leu Ser Arg Trp Arg Val Phe Ala Gly Ala Val Ala Gln
            210                 215                 220

Ala Ser Pro His Gly Leu Gln Leu Gly Val Gln Ala Val Val Tyr His
225                 230                 235                 240

Gly Gly Tyr Leu Pro Phe Arg Asp Pro Asn Ser Glu Glu Asn Ser Asn
            245                 250                 255

Asp Ile Ala Leu Val His Leu Ser Pro Leu Pro Leu Thr Glu Tyr
            260                 265                 270
```

```
Ile Gln Pro Val Cys Leu Pro Ala Ala Gly Gln Ala Leu Val Asp Gly
            275                 280                 285

Lys Ile Cys Thr Val Thr Gly Trp Gly Asn Thr Gln Tyr Tyr Gly Gln
            290                 295                 300

Gln Ala Gly Val Leu Gln Glu Ala Arg Val Pro Ile Ile Ser Asn Asp
305                 310                 315                 320

Val Cys Asn Gly Ala Asp Phe Tyr Gly Asn Gln Ile Lys Pro Lys Met
                325                 330                 335

Phe Cys Ala Gly Tyr Pro Glu Gly Gly Ile Asp Ala Cys Gln Gly Asp
                340                 345                 350

Ser Gly Gly Pro Phe Val Cys Glu Asp Ser Ile Ser Arg Thr Pro Arg
            355                 360                 365

Trp Arg Leu Cys Gly Ile Val Ser Trp Gly Thr Gly Cys Ala Leu Ala
            370                 375                 380

Gln Lys Pro Gly Val Tyr Thr Lys Val Ser Asp Phe Arg Glu Trp Ile
385                 390                 395                 400

Phe Gln Ala Ile Lys Thr His Ser Glu Ala Ser Gly Met Val Thr Gln
                405                 410                 415

Leu

<210> SEQ ID NO 4
<211> LENGTH: 372
<212> TYPE: PRT
<213> ORGANISM: Homo sapiens

<400> SEQUENCE: 4

Ser Asp Gln Glu Pro Leu Tyr Pro Val Gln Val Ser Ser Ala Asp Ala
1               5                   10                  15

Arg Leu Met Val Phe Asp Lys Thr Glu Gly Thr Trp Arg Leu Leu Cys
            20                  25                  30

Ser Ser Arg Ser Asn Ala Arg Val Ala Gly Leu Ser Cys Glu Glu Met
        35                  40                  45

Gly Phe Leu Arg Ala Leu Thr His Ser Glu Leu Asp Val Arg Thr Ala
50                  55                  60

Gly Ala Asn Gly Thr Ser Gly Phe Phe Cys Val Asp Glu Gly Arg Leu
65                  70                  75                  80

Pro His Thr Gln Arg Leu Leu Glu Val Ile Ser Val Cys Asp Cys Pro
                85                  90                  95

Arg Gly Arg Phe Leu Ala Ala Ile Cys Gln Asp Cys Gly Arg Arg Lys
            100                 105                 110

Leu Pro Val Asp Arg Ile Val Gly Gly Arg Asp Thr Ser Leu Gly Arg
        115                 120                 125

Trp Pro Trp Gln Val Ser Leu Arg Tyr Asp Gly Ala His Leu Cys Gly
130                 135                 140

Gly Ser Leu Leu Ser Gly Asp Trp Val Leu Thr Ala Ala His Cys Phe
145                 150                 155                 160

Pro Glu Arg Asn Arg Val Leu Ser Arg Trp Arg Val Phe Ala Gly Ala
                165                 170                 175

Val Ala Gln Ala Ser Pro His Gly Leu Gln Leu Gly Val Gln Ala Val
            180                 185                 190

Val Tyr His Gly Gly Tyr Leu Pro Phe Arg Asp Pro Asn Ser Glu Glu
        195                 200                 205

Asn Ser Asn Asp Ile Ala Leu Val His Leu Ser Ser Pro Leu Pro Leu
210                 215                 220
```

Thr Glu Tyr Ile Gln Pro Val Cys Leu Pro Ala Ala Gly Gln Ala Leu
225                 230                 235                 240

Val Asp Gly Lys Ile Cys Thr Val Thr Gly Trp Gly Asn Thr Gln Tyr
                245                 250                 255

Tyr Gly Gln Gln Ala Gly Val Leu Gln Glu Ala Arg Val Pro Ile Ile
            260                 265                 270

Ser Asn Asp Val Cys Asn Gly Ala Asp Phe Tyr Gly Asn Gln Ile Lys
        275                 280                 285

Pro Lys Met Phe Cys Ala Gly Tyr Pro Glu Gly Gly Ile Asp Ala Cys
    290                 295                 300

Gln Gly Asp Ser Gly Gly Pro Phe Val Cys Glu Asp Ser Ile Ser Arg
305                 310                 315                 320

Thr Pro Arg Trp Arg Leu Cys Gly Ile Val Ser Trp Gly Thr Gly Cys
                325                 330                 335

Ala Leu Ala Gln Lys Pro Gly Val Tyr Thr Lys Val Ser Asp Phe Arg
            340                 345                 350

Glu Trp Ile Phe Gln Ala Ile Lys Thr His Ser Glu Ala Ser Gly Met
        355                 360                 365

Val Thr Gln Leu
    370

<210> SEQ ID NO 5
<211> LENGTH: 239
<212> TYPE: PRT
<213> ORGANISM: Homo sapiens

<400> SEQUENCE: 5

Ile Val Gly Gly Arg Asp Thr Ser Leu Gly Arg Trp Pro Trp Gln Val
1               5                   10                  15

Ser Leu Arg Tyr Asp Gly Ala His Leu Cys Gly Gly Ser Leu Leu Ser
            20                  25                  30

Gly Asp Trp Val Leu Thr Ala Ala His Cys Phe Pro Glu Arg Asn Arg
        35                  40                  45

Val Leu Ser Arg Trp Arg Val Phe Ala Gly Ala Val Ala Gln Ala Ser
    50                  55                  60

Pro His Gly Leu Gln Leu Gly Val Gln Ala Val Val Tyr His Gly Gly
65                  70                  75                  80

Tyr Leu Pro Phe Arg Asp Pro Asn Ser Glu Glu Asn Ser Asn Asp Ile
                85                  90                  95

Ala Leu Val His Leu Ser Ser Pro Leu Pro Leu Thr Glu Tyr Ile Gln
            100                 105                 110

Pro Val Cys Leu Pro Ala Ala Gly Gln Ala Leu Val Asp Gly Lys Ile
        115                 120                 125

Cys Thr Val Thr Gly Trp Gly Asn Thr Gln Tyr Tyr Gly Gln Gln Ala
    130                 135                 140

Gly Val Leu Gln Glu Ala Arg Val Pro Ile Ile Ser Asn Asp Val Cys
145                 150                 155                 160

Asn Gly Ala Asp Phe Tyr Gly Asn Gln Ile Lys Pro Lys Met Phe Cys
                165                 170                 175

Ala Gly Tyr Pro Glu Gly Gly Ile Asp Ala Cys Gln Gly Asp Ser Gly
            180                 185                 190

Gly Pro Phe Val Cys Glu Asp Ser Ile Ser Arg Thr Pro Arg Trp Arg
        195                 200                 205

Leu Cys Gly Ile Val Ser Trp Gly Thr Gly Cys Ala Leu Ala Gln Lys
    210                 215                 220

Pro Gly Val Tyr Thr Lys Val Ser Asp Phe Arg Glu Trp Ile Phe
225                 230                 235

<210> SEQ ID NO 6
<211> LENGTH: 436
<212> TYPE: PRT
<213> ORGANISM: Mus musculus

<400> SEQUENCE: 6

Met Ala Lys Glu Asp Glu Pro Gly Ala His Arg Gly Gly Ser Thr
1               5                   10                  15

Cys Ser Arg Pro Gln Pro Gly Lys Gly Gly Arg Thr Ala Ala Cys Cys
            20                  25                  30

Ser Arg Pro Lys Val Ala Ala Leu Ile Val Gly Thr Leu Leu Phe Leu
        35                  40                  45

Thr Gly Ile Gly Ala Ala Ser Trp Ala Ile Val Thr Ile Leu Leu Gln
    50                  55                  60

Ser Asp Gln Glu Pro Leu Tyr Gln Val Gln Leu Ser Pro Gly Asp Ser
65                  70                  75                  80

Arg Leu Ala Val Phe Asp Lys Thr Glu Gly Thr Trp Arg Leu Leu Cys
                85                  90                  95

Ser Ser Arg Ser Asn Ala Arg Val Ala Gly Leu Gly Cys Glu Glu Met
            100                 105                 110

Gly Phe Leu Arg Ala Leu Ala His Ser Glu Leu Asp Val Arg Thr Ala
        115                 120                 125

Gly Ala Asn Gly Thr Ser Gly Phe Phe Cys Val Asp Glu Gly Gly Leu
    130                 135                 140

Pro Leu Ala Gln Arg Leu Leu Asp Val Ile Ser Val Cys Asp Cys Pro
145                 150                 155                 160

Arg Gly Arg Phe Leu Thr Ala Thr Cys Gln Asp Cys Gly Arg Arg Lys
                165                 170                 175

Leu Pro Val Asp Arg Ile Val Gly Gly Gln Asp Ser Ser Leu Gly Arg
            180                 185                 190

Trp Pro Trp Gln Val Ser Leu Arg Tyr Asp Gly Thr His Leu Cys Gly
        195                 200                 205

Gly Ser Leu Leu Ser Gly Asp Trp Val Leu Thr Ala Ala His Cys Phe
    210                 215                 220

Pro Glu Arg Asn Arg Val Leu Ser Arg Trp Arg Val Phe Ala Gly Ala
225                 230                 235                 240

Val Ala Arg Thr Ser Pro His Ala Val Gln Leu Gly Val Gln Ala Val
                245                 250                 255

Ile Tyr His Gly Gly Tyr Leu Pro Phe Arg Asp Pro Thr Ile Asp Glu
            260                 265                 270

Asn Ser Asn Asp Ile Ala Leu Val His Leu Ser Ser Ser Leu Pro Leu
        275                 280                 285

Thr Glu Tyr Ile Gln Pro Val Cys Leu Pro Ala Ala Gly Gln Ala Leu
    290                 295                 300

Val Asp Gly Lys Val Cys Thr Val Thr Gly Trp Gly Asn Thr Gln Phe
305                 310                 315                 320

Tyr Gly Gln Gln Ala Met Val Leu Gln Glu Ala Arg Val Pro Ile Ile
                325                 330                 335

Ser Asn Glu Val Cys Asn Ser Pro Asp Phe Tyr Gly Asn Gln Ile Lys
            340                 345                 350

Pro Lys Met Phe Cys Ala Gly Tyr Pro Glu Gly Gly Ile Asp Ala Cys

```
                355                 360                 365
Gln Gly Asp Ser Gly Gly Pro Phe Val Cys Glu Asp Ser Ile Ser Gly
            370                 375                 380

Thr Ser Arg Trp Arg Leu Cys Gly Ile Val Ser Trp Gly Thr Gly Cys
385                 390                 395                 400

Ala Leu Ala Arg Lys Pro Gly Val Tyr Thr Lys Val Thr Asp Phe Arg
                405                 410                 415

Glu Trp Ile Phe Lys Ala Ile Lys Thr His Ser Glu Ala Ser Gly Met
            420                 425                 430

Val Thr Gln Pro
        435

<210> SEQ ID NO 7
<211> LENGTH: 372
<212> TYPE: PRT
<213> ORGANISM: Mus musculus

<400> SEQUENCE: 7

Ser Asp Gln Glu Pro Leu Tyr Gln Val Gln Leu Ser Pro Gly Asp Ser
1               5                   10                  15

Arg Leu Ala Val Phe Asp Lys Thr Glu Gly Thr Trp Arg Leu Leu Cys
            20                  25                  30

Ser Ser Arg Ser Asn Ala Arg Val Ala Gly Leu Gly Cys Glu Glu Met
        35                  40                  45

Gly Phe Leu Arg Ala Leu Ala His Ser Glu Leu Asp Val Arg Thr Ala
    50                  55                  60

Gly Ala Asn Gly Thr Ser Gly Phe Phe Cys Val Asp Glu Gly Gly Leu
65                  70                  75                  80

Pro Leu Ala Gln Arg Leu Leu Asp Val Ile Ser Val Cys Asp Cys Pro
                85                  90                  95

Arg Gly Arg Phe Leu Thr Ala Thr Cys Gln Asp Cys Gly Arg Arg Lys
            100                 105                 110

Leu Pro Val Asp Arg Ile Val Gly Gly Gln Asp Ser Ser Leu Gly Arg
        115                 120                 125

Trp Pro Trp Gln Val Ser Leu Arg Tyr Asp Gly Thr His Leu Cys Gly
    130                 135                 140

Gly Ser Leu Leu Ser Gly Asp Trp Val Leu Thr Ala Ala His Cys Phe
145                 150                 155                 160

Pro Glu Arg Asn Arg Val Leu Ser Arg Trp Arg Val Phe Ala Gly Ala
                165                 170                 175

Val Ala Arg Thr Ser Pro His Ala Val Gln Leu Gly Val Gln Ala Val
            180                 185                 190

Ile Tyr His Gly Gly Tyr Leu Pro Phe Arg Asp Pro Thr Ile Asp Glu
        195                 200                 205

Asn Ser Asn Asp Ile Ala Leu Val His Leu Ser Ser Ser Leu Pro Leu
    210                 215                 220

Thr Glu Tyr Ile Gln Pro Val Cys Leu Pro Ala Ala Gly Gln Ala Leu
225                 230                 235                 240

Val Asp Gly Lys Val Cys Thr Val Thr Gly Trp Gly Asn Thr Gln Phe
                245                 250                 255

Tyr Gly Gln Gln Ala Met Val Leu Gln Glu Ala Arg Val Pro Ile Ile
            260                 265                 270

Ser Asn Glu Val Cys Asn Ser Pro Asp Phe Tyr Gly Asn Gln Ile Lys
        275                 280                 285
```

```
Pro Lys Met Phe Cys Ala Gly Tyr Pro Glu Gly Gly Ile Asp Ala Cys
    290                 295                 300
Gln Gly Asp Ser Gly Gly Pro Phe Val Cys Glu Asp Ser Ile Ser Gly
305                 310                 315                 320
Thr Ser Arg Trp Arg Leu Cys Gly Ile Val Ser Trp Gly Thr Gly Cys
                325                 330                 335
Ala Leu Ala Arg Lys Pro Gly Val Tyr Thr Lys Val Thr Asp Phe Arg
            340                 345                 350
Glu Trp Ile Phe Lys Ala Ile Lys Thr His Ser Glu Ala Ser Gly Met
        355                 360                 365
Val Thr Gln Pro
    370
```

<210> SEQ ID NO 8
<211> LENGTH: 239
<212> TYPE: PRT
<213> ORGANISM: Mus musculus

<400> SEQUENCE: 8

```
Ile Val Gly Gly Gln Asp Ser Ser Leu Gly Arg Trp Pro Trp Gln Val
1               5                   10                  15
Ser Leu Arg Tyr Asp Gly Thr His Leu Cys Gly Gly Ser Leu Leu Ser
                20                  25                  30
Gly Asp Trp Val Leu Thr Ala Ala His Cys Phe Pro Glu Arg Asn Arg
            35                  40                  45
Val Leu Ser Arg Trp Arg Val Phe Ala Gly Ala Val Ala Arg Thr Ser
        50                  55                  60
Pro His Ala Val Gln Leu Gly Val Gln Ala Val Ile Tyr His Gly Gly
65                  70                  75                  80
Tyr Leu Pro Phe Arg Asp Pro Thr Ile Asp Glu Asn Ser Asn Asp Ile
                85                  90                  95
Ala Leu Val His Leu Ser Ser Ser Leu Pro Leu Thr Glu Tyr Ile Gln
            100                 105                 110
Pro Val Cys Leu Pro Ala Ala Gly Gln Ala Leu Val Asp Gly Lys Val
        115                 120                 125
Cys Thr Val Thr Gly Trp Gly Asn Thr Gln Phe Tyr Gly Gln Gln Ala
130                 135                 140
Met Val Leu Gln Glu Ala Arg Val Pro Ile Ile Ser Asn Glu Val Cys
145                 150                 155                 160
Asn Ser Pro Asp Phe Tyr Gly Asn Gln Ile Lys Pro Lys Met Phe Cys
                165                 170                 175
Ala Gly Tyr Pro Glu Gly Gly Ile Asp Ala Cys Gln Gly Asp Ser Gly
            180                 185                 190
Gly Pro Phe Val Cys Glu Asp Ser Ile Ser Gly Thr Ser Arg Trp Arg
        195                 200                 205
Leu Cys Gly Ile Val Ser Trp Gly Thr Gly Cys Ala Leu Ala Arg Lys
210                 215                 220
Pro Gly Val Tyr Thr Lys Val Thr Asp Phe Arg Glu Trp Ile Phe
225                 230                 235
```

<210> SEQ ID NO 9
<211> LENGTH: 416
<212> TYPE: PRT
<213> ORGANISM: Mus musculus

<400> SEQUENCE: 9

```
Met Ala Lys Glu Gly Gly Arg Thr Ala Ala Cys Cys Ser Arg Pro Lys
 1               5                  10                  15

Val Ala Ala Leu Ile Val Gly Thr Leu Leu Phe Leu Thr Gly Ile Gly
             20                  25                  30

Ala Ala Ser Trp Ala Ile Val Thr Ile Leu Leu Gln Ser Asp Gln Glu
             35                  40                  45

Pro Leu Tyr Gln Val Gln Leu Ser Pro Gly Asp Ser Arg Leu Ala Val
             50                  55                  60

Leu Asp Lys Thr Glu Gly Thr Trp Arg Leu Leu Cys Ser Ser Arg Ser
 65                  70                  75                  80

Asn Ala Arg Val Ala Gly Leu Gly Cys Glu Glu Met Gly Phe Leu Arg
                 85                  90                  95

Ala Leu Ala His Ser Glu Leu Asp Val Arg Thr Ala Gly Ala Asn Gly
             100                 105                 110

Thr Ser Gly Phe Phe Cys Val Asp Glu Gly Gly Leu Pro Leu Ala Gln
             115                 120                 125

Arg Leu Leu Asp Val Ile Ser Val Cys Asp Cys Pro Arg Gly Arg Phe
             130                 135                 140

Leu Thr Ala Thr Cys Gln Asp Cys Gly Arg Arg Lys Leu Pro Val Asp
145                 150                 155                 160

Arg Ile Val Gly Gly Gln Asp Ser Ser Leu Gly Arg Trp Pro Trp Gln
                 165                 170                 175

Val Ser Leu Arg Tyr Asp Gly Thr His Leu Cys Gly Gly Ser Leu Leu
             180                 185                 190

Ser Gly Asp Trp Val Leu Thr Ala Ala His Cys Phe Pro Glu Arg Asn
             195                 200                 205

Arg Val Leu Ser Arg Trp Arg Val Phe Ala Gly Ala Val Ala Arg Thr
             210                 215                 220

Ser Pro His Ala Val Gln Leu Gly Val Gln Ala Val Ile Tyr His Gly
225                 230                 235                 240

Gly Tyr Leu Pro Phe Arg Asp Pro Thr Ile Asp Glu Asn Ser Asn Asp
                 245                 250                 255

Ile Ala Leu Val His Leu Ser Ser Ser Leu Pro Leu Thr Glu Tyr Ile
             260                 265                 270

Gln Pro Val Cys Leu Pro Ala Ala Gly Gln Ala Leu Val Asp Gly Lys
             275                 280                 285

Val Cys Thr Val Thr Gly Trp Gly Asn Thr Gln Phe Tyr Gly Gln Gln
             290                 295                 300

Ala Met Val Leu Gln Glu Ala Arg Val Pro Ile Ile Ser Asn Glu Val
305                 310                 315                 320

Cys Asn Ser Pro Asp Phe Tyr Gly Asn Gln Ile Lys Pro Lys Met Phe
                 325                 330                 335

Cys Ala Gly Tyr Pro Glu Gly Gly Ile Asp Ala Cys Gln Gly Asp Ser
             340                 345                 350

Gly Gly Pro Phe Val Cys Glu Asp Ser Ile Ser Gly Thr Ser Arg Trp
             355                 360                 365

Arg Leu Cys Gly Ile Val Ser Trp Gly Thr Gly Cys Ala Leu Ala Arg
             370                 375                 380

Lys Pro Gly Val Tyr Thr Lys Val Thr Asp Phe Arg Glu Trp Ile Phe
385                 390                 395                 400

Lys Ala Ile Lys Thr His Ser Glu Ala Ser Gly Met Val Thr Gln Pro
                 405                 410                 415
```

<210> SEQ ID NO 10
<211> LENGTH: 372
<212> TYPE: PRT
<213> ORGANISM: Mus musculus

<400> SEQUENCE: 10

```
Ser Asp Gln Glu Pro Leu Tyr Gln Val Gln Leu Ser Pro Gly Asp Ser
  1               5                  10                  15

Arg Leu Ala Val Leu Asp Lys Thr Glu Gly Thr Trp Arg Leu Leu Cys
             20                  25                  30

Ser Ser Arg Ser Asn Ala Arg Val Ala Gly Leu Gly Cys Glu Glu Met
         35                  40                  45

Gly Phe Leu Arg Ala Leu Ala His Ser Glu Leu Asp Val Arg Thr Ala
 50                  55                  60

Gly Ala Asn Gly Thr Ser Gly Phe Phe Cys Val Asp Glu Gly Gly Leu
 65                  70                  75                  80

Pro Leu Ala Gln Arg Leu Leu Asp Val Ile Ser Val Cys Asp Cys Pro
                 85                  90                  95

Arg Gly Arg Phe Leu Thr Ala Thr Cys Gln Asp Cys Gly Arg Arg Lys
            100                 105                 110

Leu Pro Val Asp Arg Ile Val Gly Gly Gln Asp Ser Ser Leu Gly Arg
            115                 120                 125

Trp Pro Trp Gln Val Ser Leu Arg Tyr Asp Gly Thr His Leu Cys Gly
130                 135                 140

Gly Ser Leu Leu Ser Gly Asp Trp Val Leu Thr Ala Ala His Cys Phe
145                 150                 155                 160

Pro Glu Arg Asn Arg Val Leu Ser Arg Trp Arg Val Phe Ala Gly Ala
                165                 170                 175

Val Ala Arg Thr Ser Pro His Ala Val Gln Leu Gly Val Gln Ala Val
            180                 185                 190

Ile Tyr His Gly Gly Tyr Leu Pro Phe Arg Asp Pro Thr Ile Asp Glu
        195                 200                 205

Asn Ser Asn Asp Ile Ala Leu Val His Leu Ser Ser Ser Leu Pro Leu
    210                 215                 220

Thr Glu Tyr Ile Gln Pro Val Cys Leu Pro Ala Ala Gly Gln Ala Leu
225                 230                 235                 240

Val Asp Gly Lys Val Cys Thr Val Thr Gly Trp Gly Asn Thr Gln Phe
                245                 250                 255

Tyr Gly Gln Gln Ala Met Val Leu Gln Glu Ala Arg Val Pro Ile Ile
            260                 265                 270

Ser Asn Glu Val Cys Asn Ser Pro Asp Phe Tyr Gly Asn Gln Ile Lys
        275                 280                 285

Pro Lys Met Phe Cys Ala Gly Tyr Pro Glu Gly Gly Ile Asp Ala Cys
    290                 295                 300

Gln Gly Asp Ser Gly Gly Pro Phe Val Cys Glu Asp Ser Ile Ser Gly
305                 310                 315                 320

Thr Ser Arg Trp Arg Leu Cys Gly Ile Val Ser Trp Gly Thr Gly Cys
                325                 330                 335

Ala Leu Ala Arg Lys Pro Gly Val Tyr Thr Lys Val Thr Asp Phe Arg
            340                 345                 350

Glu Trp Ile Phe Lys Ala Ile Lys Thr His Ser Glu Ala Ser Gly Met
        355                 360                 365

Val Thr Gln Pro
    370
```

<210> SEQ ID NO 11
<211> LENGTH: 239
<212> TYPE: PRT
<213> ORGANISM: Mus musculus

<400> SEQUENCE: 11

Ile Val Gly Gly Gln Asp Ser Ser Leu Gly Arg Trp Pro Trp Gln Val
1               5                   10                  15

Ser Leu Arg Tyr Asp Gly Thr His Leu Cys Gly Gly Ser Leu Leu Ser
            20                  25                  30

Gly Asp Trp Val Leu Thr Ala Ala His Cys Phe Pro Glu Arg Asn Arg
        35                  40                  45

Val Leu Ser Arg Trp Arg Val Phe Ala Gly Ala Val Ala Arg Thr Ser
    50                  55                  60

Pro His Ala Val Gln Leu Gly Val Gln Ala Val Ile Tyr His Gly Gly
65                  70                  75                  80

Tyr Leu Pro Phe Arg Asp Pro Thr Ile Asp Glu Asn Ser Asn Asp Ile
                85                  90                  95

Ala Leu Val His Leu Ser Ser Ser Leu Pro Leu Thr Glu Tyr Ile Gln
            100                 105                 110

Pro Val Cys Leu Pro Ala Ala Gly Gln Ala Leu Val Asp Gly Lys Val
        115                 120                 125

Cys Thr Val Thr Gly Trp Gly Asn Thr Gln Phe Tyr Gly Gln Gln Ala
130                 135                 140

Met Val Leu Gln Glu Ala Arg Val Pro Ile Ile Ser Asn Glu Val Cys
145                 150                 155                 160

Asn Ser Pro Asp Phe Tyr Gly Asn Gln Ile Lys Pro Lys Met Phe Cys
                165                 170                 175

Ala Gly Tyr Pro Glu Gly Gly Ile Asp Ala Cys Gln Gly Asp Ser Gly
            180                 185                 190

Gly Pro Phe Val Cys Glu Asp Ser Ile Ser Gly Thr Ser Arg Trp Arg
        195                 200                 205

Leu Cys Gly Ile Val Ser Trp Gly Thr Gly Cys Ala Leu Ala Arg Lys
    210                 215                 220

Pro Gly Val Tyr Thr Lys Val Thr Asp Phe Arg Glu Trp Ile Phe
225                 230                 235

<210> SEQ ID NO 12
<211> LENGTH: 416
<212> TYPE: PRT
<213> ORGANISM: Mus musculus

<400> SEQUENCE: 12

Met Ala Lys Glu Gly Gly Arg Thr Ala Ala Cys Cys Ser Arg Pro Lys
1               5                   10                  15

Val Ala Ala Leu Ile Val Gly Thr Leu Leu Phe Leu Thr Gly Ile Gly
            20                  25                  30

Ala Ala Ser Trp Ala Ile Val Thr Ile Leu Leu Gln Ser Asp Gln Glu
        35                  40                  45

Pro Leu Tyr Gln Val Gln Leu Ser Pro Gly Asp Ser Arg Leu Ala Val
    50                  55                  60

Leu Asp Lys Thr Glu Gly Thr Trp Arg Leu Leu Cys Ser Ser Arg Ser
65                  70                  75                  80

Asn Ala Arg Val Ala Gly Leu Gly Cys Glu Glu Met Gly Phe Leu Arg
                85                  90                  95

```
Ala Leu Ala His Ser Glu Leu Asp Val Arg Thr Ala Gly Ala Asn Gly
            100             105             110

Thr Ser Gly Phe Phe Cys Val Asp Glu Gly Gly Leu Pro Leu Ala Gln
            115             120             125

Arg Leu Leu Asp Val Ile Ser Val Cys Asp Cys Pro Arg Gly Arg Phe
            130             135             140

Leu Thr Ala Thr Cys Gln Asp Cys Gly Arg Arg Lys Leu Pro Val Asp
145             150             155             160

Arg Ile Val Gly Gly Gln Asp Ser Ser Leu Gly Arg Trp Pro Trp Gln
                165             170             175

Val Ser Leu Arg Tyr Asp Gly Thr His Leu Cys Gly Gly Ser Leu Leu
            180             185             190

Ser Gly Asp Trp Val Leu Thr Ala Ala His Cys Phe Pro Glu Arg Asn
            195             200             205

Arg Val Leu Ser Arg Trp Arg Val Phe Ala Gly Ala Val Ala Arg Thr
            210             215             220

Ser Pro His Ala Val Gln Leu Gly Val Gln Ala Val Ile Tyr His Gly
225             230             235             240

Gly Tyr Leu Pro Phe Arg Asp Pro Thr Ile Asp Glu Asn Ser Asn Asp
                245             250             255

Ile Ala Leu Val His Leu Ser Ser Ser Leu Pro Leu Thr Glu Tyr Ile
            260             265             270

Gln Pro Val Cys Leu Pro Ala Ala Gly Gln Ala Leu Val Asp Gly Lys
            275             280             285

Val Cys Thr Val Thr Gly Trp Gly Asn Thr Gln Phe Tyr Gly Gln Gln
290             295             300

Ala Met Val Leu Gln Glu Ala Arg Val Pro Ile Ile Ser Asn Glu Val
305             310             315             320

Cys Asn Ser Pro Asp Phe Tyr Gly Asn Gln Ile Lys Pro Lys Met Phe
                325             330             335

Cys Ala Gly Tyr Pro Glu Gly Gly Ile Asp Ala Cys Gln Gly Asp Ala
            340             345             350

Gly Gly Pro Phe Val Cys Glu Asp Ser Ile Ser Gly Thr Ser Arg Trp
            355             360             365

Arg Leu Cys Gly Ile Val Ser Trp Gly Thr Gly Cys Ala Leu Ala Arg
370             375             380

Lys Pro Gly Val Tyr Thr Lys Val Thr Asp Phe Arg Glu Trp Ile Phe
385             390             395             400

Lys Ala Ile Lys Thr His Ser Glu Ala Ser Gly Met Val Thr Gln Pro
            405             410             415
```